(12) United States Patent  (10) Patent No.: US 8,034,968 B2
Annis (45) Date of Patent: Oct. 11, 2011

(54) PROCESS FOR PREPARING 2-AMINO-5-CYANOBENZOIC ACID DERIVATIVES

(75) Inventor: Gary David Annis, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 103 days.

(21) Appl. No.: 12/596,556

(22) PCT Filed: Jun. 23, 2008

(86) PCT No.: PCT/US2008/067826
§ 371 (c)(1),
(2), (4) Date: Oct. 19, 2009

(87) PCT Pub. No.: WO2009/006061
PCT Pub. Date: Jan. 8, 2009

(65) Prior Publication Data
US 2010/0063287 A1      Mar. 11, 2010

Related U.S. Application Data

(60) Provisional application No. 60/937,815, filed on Jun. 29, 2007.

(51) Int. Cl.
*C07C 255/50* (2006.01)
(52) U.S. Cl. ......... 558/415; 558/303; 558/411; 558/416
(58) Field of Classification Search .............. 558/303, 558/411, 415, 416
See application file for complete search history.

(56) References Cited

U.S. PATENT DOCUMENTS
7,528,260 B2 * 5/2009 Shapiro et al. ............. 548/374.1

FOREIGN PATENT DOCUMENTS
| EP | 0384392 A1 | 8/1990 |
| WO | 2004/067528 A1 | 8/2004 |
| WO | 2006/023783 A1 | 3/2006 |
| WO | 2006/062978 A1 | 6/2006 |
| WO | 2006/068669 A1 | 6/2006 |

OTHER PUBLICATIONS

Y. Sakakibara et al., "The Cyanation of Aromatic Halides Catalyzed by Nickel(0) Complexes Generated In Situ III", *Bull. Chem. Soc. JP.* 2004, vol. 77, pp. 1013-1019.
Y. Sakakibara et al., "The Cyanation of Aromatic Halides Catalyzed by Nickel(0) Complexes Generated In Situ I", *Bull. Chem. Soc. JP.* 1988, vol. 61, pp. 1985-1990.
J. Van Soolingen et al., "Nickel-Catalyzed Cyanation of 2- and 3-Bromothiophene", *Synthetic Communications*, 1990, vol. 20, pp. 3153-3156.
L. Cassar et al., "Nickel-Catalyzed Cyanation of Aromatic Halides", *Advances in Chemistry*, 1974, vol. 132, pp. 252-273.
R. K. Arvela et al., Rapid Easy Cyanation of Aryl Bromides and Chlorides Using Nickel Salts in Conjunction with Microwave Applications:, *J. Org. Chem.* 2003, vol. 68, pp. 9122-9125.

* cited by examiner

*Primary Examiner* — Golam M M Shameem
(74) *Attorney, Agent, or Firm* — Renee M. Lett

(57) ABSTRACT

Disclosed is a method for preparing a compound of Formula 1 comprising (1) contacting a compound of Formula 2, with (2) at least one alkali metal cyanide and (3) at least one compound of Formula 4

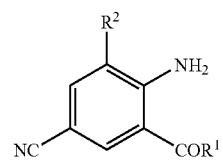

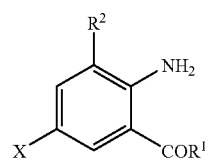

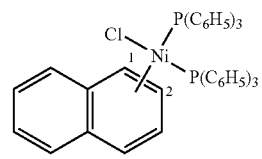

wherein $R^1$ is $NHR^3$ or $OR^4$; $R^2$ is $CH_3$ or Cl; $R^3$ is H, $C_1$-$C_4$ alkyl, cyclopropyl, cyclopropylcyclopropyl, cyclopropylmethyl or methylcyclopropyl; $R^4$ is H or $C_1$-$C_4$ alkyl; and X is Br, Cl or I.

Also disclosed is a method for preparing a compound of Formula 4 comprising contacting a mixture of (i) at least one compound of Formula 9 and (ii) at least one metal reducing agent with (iii) dichlorobis(triphenylphosphine)nickel, and further disclosed is a method for removing nickel impurities from a mixture thereof with compounds of Formula 1 comprising contacting the mixture with oxygen in the presence of an aqueous cyanide solution, and additionally disclosed is a method for preparing a compound of Formula 5

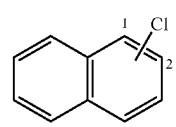

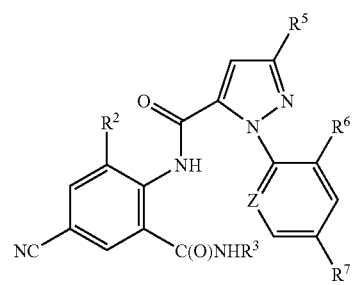

wherein $R^5$, $R^6$, $R^7$ and Z are as defined in the disclosure, using a compound of Formula 1, characterized by preparing the compound of Formula 1 by the method disclosed above.

13 Claims, No Drawings

PROCESS FOR PREPARING 2-AMINO-5-CYANOBENZOIC ACID DERIVATIVES

FIELD OF THE INVENTION

The present invention pertains to a method for the preparation of 3-substituted 2-amino-5-cyanobenzoic acid derivatives.

BACKGROUND OF THE INVENTION

Preparation of certain 2-amino-5-cyanobenzoic acid derivatives and their utility as intermediates for preparing corresponding insecticidal cyanoanthranilic diamides has been disclosed (see e.g., Scheme 9 in PCT Patent Publication WO 2004/067528; Scheme 9 and Example 2, Step A in PCT Patent Publication WO 2006/068669; and Scheme 15 and Example 6, Step B in PCT Patent Publication WO 2006/062978).

However, the need continues for new or improved methods suitable for rapidly providing 2-amino-5-cyanobenzoic acid derivatives.

SUMMARY OF THE INVENTION

The present invention is directed to a method for preparing a compound of Formula 1

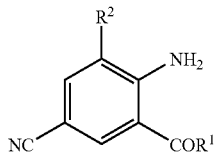

wherein
  $R^1$ is $NHR^3$ or $OR^4$;
  $R^2$ is $CH_3$ or Cl;
  $R^3$ is H, $C_1$-$C_4$ alkyl, cyclopropyl, cyclopropylcyclopropyl, cyclopropylmethyl or methylcyclopropyl; and
  $R^4$ is H or $C_1$-$C_4$ alkyl;
comprising contacting (1) a compound of Formula 2

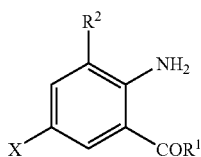

wherein X is Br, Cl or I;
with (2) at least one compound of Formula 3

$$M^1CN \qquad 3$$

wherein $M^1$ is an alkali metal;

and (3) at least one compound of Formula 4

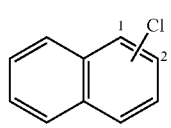

provided that when X is Cl, then $R^2$ is methyl.

This invention also provides a method for preparing a compound of Formula 4 comprising contacting a mixture of (i) at least one compound of Formula 9

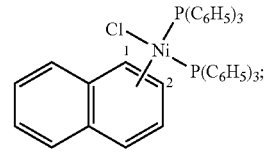

and (ii) at least one metal reducing agent with (iii) dichlorobis(triphenylphosphine)nickel.

This invention also provides a method for removing nickel impurities from a mixture thereof with compounds of Formula 1 comprising contacting the mixture with oxygen in the presence of an aqueous cyanide solution.

This invention also provides a method for preparing a compound of Formula 5

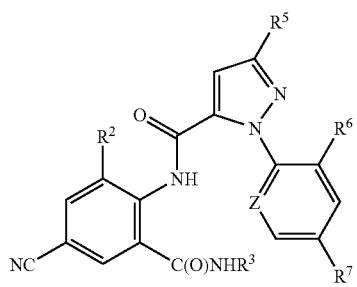

wherein
  $R^2$ is $CH_3$ or Cl;
  $R^3$ is H, $C_1$-$C_4$ alkyl, cyclopropyl, cyclopropylcyclopropyl, cyclopropylmethyl, or methylcyclopropyl;
  Z is $CR^8$ or N;
  $R^5$ is Cl, Br, $CF_3$, $OCF_2H$ or $OCH_2CF_3$;
  $R^6$ is F, Cl or Br;
  $R^7$ is H, F or Cl; and
  $R^8$ is H, F, Cl or Br;
using a compound of Formula 1. The method is characterized by (a) preparing the compound of Formula 1 from the compounds of Formulae 2, 3 and 4 by the method disclosed above, or (b) using as said compound of Formula 1a compound of Formula 1 prepared by the method disclosed above.

Further related aspects of the present invention pertain to combinations of the aforedescribed methods, including a method for preparing a compound of Formula 5 comprising preparing a compound of Formula 4 as described above, then preparing a compound of Formula 1 from the compounds of Formulae 2, 3 and 4 as described above, then optionally removing nickel impurities from a mixture thereof with compounds of Formula 1 as described above, and then preparing the compound of Formula 5 using the compound of Formula 1.

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

Ratios are generally recited herein as single numbers, which are relative to the number 1; for example, a ratio of 2 means 2:1.

Molar percentage of a first compound relative to a second compound is calculated by dividing the number of moles of the first compound by the number of moles of the second compound and multiplying the quotient by 100.

In the above recitations, the term "alkyl" includes straight-chain or branched alkyl, such as, methyl, ethyl, butyl, n-propyl, i-propyl, or the different butyl isomers.

In the context of the present invention the term "metal reducing agent" refers to any elemental metal which is more electropositive than nickel, and is in powder form. Examples of such a metal include, but are not limited to, zinc and manganese, including alloys comprising them (e.g., manganese-iron alloy).

The term "cyclopropylcyclopropyl" denotes cyclopropyl substitution on a cyclopropyl moiety and includes, for example, 1,1'-bicyclopropyl-1-yl, 1,1'-bicyclopropyl-2-yl and the different isomers such as (1R,2S)-1,1'-bicyclopropyl-2-yl and (1R,2R)-1,1'-bicyclopropyl-2-yl.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and 0 to 3 heteroatoms. Of note are carbon-based radicals selected from $C_1$-$C_4$ alkyl, $C_1$-$C_2$ haloalkyl, and phenyl optionally substituted with 1-3 substituents selected from $C_1$-$C_3$ alkyl, halogen and nitro.

As referred to in the present disclosure, the term "carboxylic acid" means an organic chemical compound comprising at least one carboxylic acid functional group (i.e. —C(O)OH). The term "carboxylic acid" does not include the compound carbonic acid (i.e. HOC(O)OH). Carboxylic acids include, for example, formic acid, acetic acid, propionic acid, chloroacetic acid, benzoic acid, maleic acid, and citric acid. The term "effective $pK_a$" refers to the $pK_a$ of the carboxylic acid functional group, or if the compound has more than one carboxylic acid functional group, "effective $pK_a$" refers to the $pK_a$ of the most acidic carboxylic acid functional group. As referred to herein, the "effective pH" of a nonaqueous substance or mixture, such as a reaction mixture, is determined by mixing an aliquot of the substance or mixture with about 5 to 20 volumes of water and then measuring the pH of the resulting aqueous mixture (e.g., with a pH meter). As referred to herein, a "substantially anhydrous" substance means the substance contains no more than about 1% water by weight. The chemical name "isatoic anhydride" is another name corresponding to the current Chemical Abstracts name "2H-3,1-benzoxazine-2,4(1H)-dione".

Embodiments of the present invention include:

Embodiment A1

The method described in the Summary of the Invention for preparing a compound of Formula 1 comprising contacting reagent (1) (i.e. a compound of Formula 2) with reagent (2) (i.e. at least one compound of Formula 3) and reagent (3) (i.e. at least one compound of Formula 4).

Embodiment A2

The method of Embodiment A1 wherein $R^1$ is $NHR^3$.

Embodiment A3

The method of Embodiment A1 or A2 wherein $R^3$ is $C_1$-$C_4$ alkyl, cyclopropyl, cyclopropylcyclopropyl, cyclopropylmethyl or methylcyclopropyl.

Embodiment A4

The method of Embodiment A3 wherein $R^3$ is $C_1$-$C_4$ alkyl or cyclopropylmethyl.

Embodiment A5

The method of Embodiment A4 wherein $R^3$ is $CH_3$.

Embodiment A6

The method of anyone of Embodiments A1 through A5 wherein $R^2$ is $CH_3$.

Embodiment A7

The method of anyone of Embodiments A1 through A6 wherein $M^1$ is selected from the group consisting of sodium, potassium, rubidium and cesium.

Embodiment A8

The method of Embodiment A7 wherein $M^1$ is selected from the group consisting of sodium and potassium.

Embodiment A9

The method of Embodiment A8 wherein $M^1$ is potassium.

Embodiment A10

The method of anyone of Embodiments A1 through A9 wherein X is Br or Cl.

Embodiment A11

The method of anyone of Embodiments A1 through A10 wherein reagent (3) contains at least about 80 percent chloro-1-naphthalenylbis(triphenylphosphine)nickel.

Embodiment A12

The method of Embodiment A11 wherein reagent (3) contains at least about 90 percent chloro-1-naphthalenylbis(triphenylphosphine)nickel.

Embodiment A13

The method of anyone of Embodiments A1 through A12 wherein the ratio of the number of moles of reagent (2) (i.e. the number of moles of CN) to the sum of the number of moles of reagent (1) and reagent (3) is at least about 1.

Embodiment A14

The method of anyone of Embodiments A1 through A13 wherein the mole ratio of reagent (2) to reagent (1) is at least about 1.07.

Embodiment A15

The method of Embodiment A14 wherein the mole ratio of reagent (2) to reagent (1) is at least about 1.5.

Embodiment A15A

The method of Embodiment A15 wherein the mole ratio of reagent (2) to reagent (1) is at least about 2.

Embodiment A16

The method of anyone of Embodiments A1 through A15A wherein the mole ratio of reagent (2) to reagent (1) is not larger than about 6.

Embodiment A17

The method of Embodiment A16 wherein the mole ratio of reagent (2) to reagent (1) is not larger than about 2.5.

Embodiment A18

The method of anyone of Embodiments A1 through A11 wherein the mole percentage of reagent (3) relative to reagent (1) is at least about 1%.

Embodiment A19

The method of Embodiment A18 wherein the mole percentage of reagent (3) relative to reagent (1) is at least about 5%.

Embodiment A20

The method of Embodiment A19 wherein the mole percentage of reagent (3) relative to reagent (1) is at least about 7%.

Embodiment A21

The method of anyone of Embodiments A1 through A20 wherein the mole percentage of reagent (3) relative to reagent (1) is not larger than about 15%.

Embodiment A22

The method of Embodiment A21 wherein the mole percentage of reagent (3) relative to reagent (1) is not larger than about 12%.

Embodiment A23

The method of Embodiment A22 wherein the mole percentage of reagent (3) relative to reagent (1) is not larger than about 10%.

Embodiment A24

The method of anyone of Embodiments A1 through A23 wherein reagent (1), reagent (2) and reagent (3) are contacted in the presence of a suitable organic solvent.

Embodiment A25

The method of Embodiment A24 wherein reagent (1) and reagent (2) are contacted with the suitable organic solvent to form a mixture, and then reagent (3) is added to the mixture.

Embodiment A26

The method of Embodiment A24 wherein reagent (1) and reagent (2) are contacted with the suitable organic solvent to form a mixture, and then a slurry of reagent (3) in the suitable organic solvent is added to the mixture.

Embodiment A27

The method of any one of Embodiments A24, A25 and A26 wherein the suitable organic solvent comprises one or more solvents selected from the group consisting of alcohols, amides, and halogenated and nonhalogenated aliphatic and aromatic hydrocarbons.

Embodiment A28

The method of Embodiment A27 wherein the suitable organic solvent comprises one or more solvents selected from ethanol, N,N'-dimethylformamide, xylenes and toluene.

Embodiment A29

The method of Embodiment A27 or A28 wherein the suitable organic solvent comprises ethanol.

Embodiment A30

The method of Embodiment A29 wherein the suitable organic solvent comprises at least about 50% ethanol by weight.

Embodiment A31

The method of Embodiment A30 wherein the suitable organic solvent comprises at least about 70% ethanol by weight.

Embodiment A32

The method of Embodiment A31 wherein the suitable organic solvent comprises at least about 80% ethanol by weight.

Embodiment A33

The method of any one of Embodiments A24 through A32 wherein the ratio of the total volume of the suitable organic solvent to the weight of reagent (1) is at least about 6 mL/g.

Embodiment A34

The method of Embodiment A33 wherein the ratio of the total volume of the suitable organic solvent to the weight of reagent (1) is at least about 8 mL/g.

Embodiment A35

The method of any one of Embodiments A24 through A34 wherein the ratio of the total volume of the suitable organic solvent to the weight of reagent (1) is not larger than about 15 mL/g.

Embodiment A36

The method of Embodiment A35 wherein the ratio of the total volume of the suitable organic solvent to the weight of reagent (1) is not larger than about 10 mL/g.

Embodiment A37

The method of any one of Embodiments A24 through A36 wherein reagent (1), reagent (2) and reagent (3) are contacted in the presence of a suitable organic solvent at a temperature not greater than about 100° C.

Embodiment A38

The method of Embodiment A37 wherein reagent (1), reagent (2) and reagent (3) are contacted in the presence of a suitable organic solvent at a temperature not greater than about 75° C.

Embodiment A39

The method of Embodiment A38 wherein reagent (1), reagent (2) and reagent (3) are contacted in the presence of a suitable organic solvent at a temperature not greater than about 45° C.

Embodiment A40

The method of any one of Embodiments A24 through A39 wherein reagent (1), reagent (2) and reagent (3) are contacted in the presence of a suitable organic solvent at a temperature greater than about 10° C.

Embodiment A41

The method of Embodiment A40 wherein reagent (1), reagent (2) and reagent (3) are contacted in the presence of a suitable organic solvent at a temperature greater than about 25° C.

Embodiment A42

The method of Embodiment A41 wherein reagent (1), reagent (2) and reagent (3) are contacted in the presence of a suitable organic solvent at a temperature greater than about 35° C.

Embodiment B1

The method described in the Summary of the Invention for preparing a compound of Formula 4 comprising contacting a mixture of reagent (i) (i.e. at least one compound of Formula 9) and reagent (ii) (i.e. at least one metal reducing agent) with reagent (iii) (i.e. dichlorobis(triphenylphosphine)nickel).

Embodiment B2

The method of Embodiment B1 wherein reagent (i) and reagent (ii) are contacted in the presence of a suitable organic solvent (iv) to form a mixture, and then reagent (iii) is added to the mixture.

Embodiment B3

The method of anyone of Embodiments B1 or B2 wherein reagent (i) and reagent (ii) are contacted with the suitable organic solvent to form a mixture, and then a slurry of reagent (iii) in the suitable organic solvent (iv) is added to the mixture.

Embodiment B3A

The method of Embodiment B2 wherein reagent (iii) is added as a slurry in the suitable organic solvent (iv) to the mixture formed from reagent (i), reagent (ii) and the suitable organic solvent (iv).

Embodiment B4

The method of any one of Embodiments B1 through B3 wherein reagent (iii) is prepared by contacting triphenylphosphine and nickel(II) chloride hexahydrate in the presence of a suitable organic solvent (v).

Embodiment B5

The method of Embodiment B4 wherein the mole ratio of the triphenylphosphine to the nickel(II) chloride hexahydrate is at least about 2.

Embodiment B6

The method of Embodiment B5 wherein the mole ratio of the triphenylphosphine to the nickel(II) chloride hexahydrate is at least about 2.5.

Embodiment B7

The method of any one of Embodiments B1 through B6 wherein the mole ratio of the triphenylphosphine to the nickel (II) chloride hexahydrate is not larger than about 4.

Embodiment B8

The method of Embodiment B7 wherein the mole ratio of the triphenylphosphine to the nickel(II) chloride hexahydrate is not larger than about 3.

Embodiment B9

The method of any one of any one of Embodiments B4 through B8 wherein the suitable organic solvent (v) is ethanol.

Embodiment B10

The method of any one of any one of Embodiments B1 through B9 wherein reagent (i) contains at least about 80 percent 1-chloronaphthalene.

Embodiment B11

The method of Embodiment B10 wherein reagent (i) contains at least about 90 percent 1-chloronaphthalene.

Embodiment B12

The method of any one of Embodiments B1 through B11 wherein the mole ratio of reagent (iii) to reagent (i) is at least about 0.3.

Embodiment B12A

The method of Embodiment B1 wherein the mole ratio of reagent (iii) to reagent (i) is at least about 0.4.

Embodiment B13

The method of Embodiment B12 wherein the mole ratio of reagent (iii) to reagent (i) is at least about 0.5.

Embodiment B14

The method of any one of any one of Embodiments B1 through B13 wherein the mole ratio of reagent (iii) to reagent (i) is not larger than about 1.

Embodiment B15

The method of Embodiment B14 wherein the mole ratio of reagent (iii) to reagent (i) is not larger than about 0.8.

Embodiment B16

The method of any one of Embodiments B1 through B15 wherein reagent (ii) comprises zinc.

Embodiment B17

The method of Embodiment B16 wherein the mole ratio of the zinc to reagent (i) is at least about 1.

Embodiment B18

The method of Embodiment B17 wherein the mole ratio of the zinc to reagent (i) is at least about 1.5.

Embodiment B19

The method of any one of Embodiments B16 through B18 wherein the mole ratio of the zinc to reagent (i) is not larger than about 5.

Embodiment B20

The method of Embodiment B19 wherein the mole ratio of the zinc to reagent (i) is not larger than about 3.

Embodiment B21

The method of any one of Embodiments B1 through B20 wherein the mole ratio of reagent (i) to reagent (iii) is at least about 1.

Embodiment B22

The method of Embodiment B21 wherein the mole ratio of reagent (i) to reagent (iii) is at least about 2.

Embodiment B23

The method of any one of Embodiments B1 through B22 wherein the mole ratio of reagent (i) to reagent (iii) is not larger than about 3.

Embodiment B24

The method of Embodiment B23 wherein the mole ratio of reagent (i) to the dichlorobis(triphenylphosphine)nickel is not larger than about 2.5.

Embodiment C1

The method described in the Summary of the Invention for removing nickel impurities from a mixture thereof with compounds of Formula 1 comprising contacting the mixture with oxygen in the presence of an aqueous cyanide solution.

Embodiment C2

The method of Embodiment C1 wherein the aqueous cyanide solution comprises potassium cyanide or sodium cyanide.

Embodiment C3

The method of Embodiment C1 or C2 wherein the mixture of nickel impurities and the compound Formula 1 is contacted with oxygen by sparging the mixture with air, or by exposing the mixture to air.

Embodiment C4

The method of any one of Embodiments C1 through C3 wherein the mixture of nickel impurities and the compound of Formula 1 is contacted with oxygen and the aqueous cyanide solution at a temperature not greater than about 100° C.

Embodiment C5

The method of Embodiment C4 wherein the mixture of nickel impurities and the compound of Formula 1 is contacted with oxygen and the aqueous cyanide solution at a temperature not greater than about 70° C.

Embodiment C6

The method of Embodiment C5 wherein the mixture of nickel impurities and the compound of Formula 1 is contacted with oxygen and the aqueous cyanide solution at a temperature not greater than about 50° C.

Embodiment C7

The method of any one of Embodiments C1 through C6 wherein the mixture of nickel impurities and the compound of Formula 1 is contacted with oxygen and the aqueous cyanide solution at a temperature greater than about 25° C.

Embodiment C8

The method of Embodiment C7 wherein the mixture of nickel impurities and the compound of Formula 1 is contacted with oxygen and the aqueous cyanide solution at a temperature greater than about 45° C.

Embodiment D1

The method described in the Summary of the Invention for preparing a compound of Formula 5 using the compound of Formula 1 prepared from the compound of Formula 2.

Embodiment D2

The method of Embodiment D1 wherein Z is N.

Embodiment D3

The method of Embodiment D1 wherein Z is CH.

Embodiment D4

The method of any one of Embodiments D1 through D3 wherein $R^3$ is H, $C_1$-$C_4$ alkyl, cyclopropyl, cyclopropylmethyl or methylcyclopropyl.

Embodiment D5

The method of Embodiment D4 wherein $R^3$ is $C_1$-$C_4$ alkyl or cyclopropylmethyl.

Embodiment D6

The method of Embodiment D5 wherein $R^3$ is $CH_3$.

Embodiment D7

The method of any one of Embodiments D1 through D6 wherein $R^2$ is $CH_3$.

Embodiment D8

The method of any one of Embodiments D1 through D8 wherein $R^5$ is Br.

Embodiment D9

The method of any one of Embodiments D1 through D8 wherein $R^6$ is Cl.

Embodiment D10

The method of any one of Embodiments D1 through D9 wherein $R^7$ is H.

Embodiments of this invention can be combined in any manner.

In the following Schemes 1-8 the definitions of $R^1$, $R^2$, $R^3$, $R^4$, $R^5$, $R^6$, $R^7$, $R^8$, $M^1$, X, and Z in the compounds of Formulae 1 through 12 are as defined above in the Summary of the Invention and description of Embodiments unless otherwise indicated. Formulae 1a, 1b and 1c are subsets of Formula 1. Formula 2a is a subset of Formula 2.

As shown in Scheme 1, in a method of the present invention a compound of Formula 1 is prepared by contacting a compound of Formula 2 with at least one alkali metal cyanide of Formula 3 and at least one compound of Formula 4.

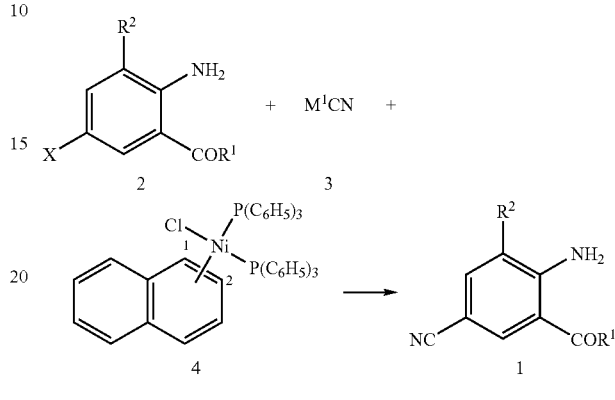

Scheme 1

In the method of Scheme 1, compounds of Formula 3 comprise $M^1$, which is an alkali metal, preferably K, Na, Cs or Rb, more preferably K or Na, and most preferably K. As cyanide provided by the compound of Formula 3 is believed to first react with a compound of Formula 4 and then a compound of Formula 2, the stoichiometry of the reaction requires at least one molar equivalent of Formula 3 relative to the sum of the number of moles of the compounds of Formulae 2 and 4. Typically the molar ratio of the compound or compounds of Formula 3 (i.e. the number of moles of CN) relative to the compound of Formula 2 is from about 1.07 to about 6. Although higher levels of Formula 3 compounds can be used there is no particular advantage in doing so and higher levels increase raw material and waste processing costs. The highest product yields are usually achieved with molar ratios of Formula 3 from about 1.5 to about 2 relative to the compound of Formula 2. In some cases the optimal molar ratio of Formula 3 compounds to the compounds of Formula 2 varies depending on the particle size (although the molar ratios are still within ranges described above). For example, commercially obtained alkali metal cyanides can consist of irregularly shaped particles with varying particle size distribution; thus the optimal molar ratio is sometimes greater when using commercially obtained alkali metal cyanides instead of using smaller particle size material. Grinding or milling alkali metal cyanides prior to use can provide smaller particle size material.

In the present method the compound or compounds of Formula 4 act as a source of a chemical species which catalyzes the conversion of compounds of Formula 2 to compounds of Formula 1. In the method of Scheme 1, Formula 4 is chloro-1-naphthalenylbis-(triphenylphosphine)nickel (also known as trans-chloro(1-naphthyl)bis(triphenylphosphine)-nickel), or Formula 4 is a mixture of 1- and 2-isomers of chloronaphthalenylbis-(triphenylphosphine)nickel. If a mixture of isomers is used preferably the mixture contains at least about 80 percent and more preferably at least about 90 percent of chloro-1-naphthalenylbis(triphenylphosphine) nickel. The total molar percentage of the compound or compounds of Formula 4 relative to the compound of Formula 2 is preferably from about 1% to about 15%. As molar percentages greater than 1% can often accelerate the reaction while percentages above 15% generally offer little additional benefit while increasing cost, the molar percentage is more preferably from about 7% to about 10%. When X attached to the compound of Formula 2 is Br, most preferred are molar percentages from about 6% to about 7%; and when X is Cl, most preferred are molar percentages from about 9.5% to about 10%. In some cases it may be beneficial to carry out the process of Scheme 1 in the presence of a suitable ligand in addition to the ligands bonded in Formula 4. Suitable ligands are ligands capable of coordinating to nickel including, for example, substituted phosphines (e.g., triphenylphosphine) or cycloalkadienes (e.g., 1,5-cyclooctadiene). Often reaction rates and yields are enhanced by the addition of about 1 to 2 molar percent of triphenylphosphine or about 10 molar percent of 1,5-cyclooctadiene relative to the compound of Formula 2 and increasing the reaction temperature. The addition of a suitable ligand in the present process can also influence the optimal reaction temperature, relative to when the process is conducted without a ligand (other then the ligands bonded in Formula 4). For example, when about 5-10 molar percent of triphenylphosphine relative to the compound of Formula 2 is added the most favorable reaction rates, providing the highest yields of compounds of Formula 1 are typically obtained with reaction temperatures in the range of about 45 to 75° C., as compared to about 40 to 45° C. without added triphenylphosphine. However, the usefulness of a ligand, other than the ligands bonded in Formula 4, in some cases diminishes with larger amounts. In particular, reaction rates typically show little improvement with amounts of triphenylphosphine greater than about 10 molar percent.

The method of Scheme 1 is typically conducted in a suitable organic solvent. A variety of organic solvents can be used to form the suitable organic solvent for this method. Typically, the method is most satisfactorily conducted using solvents in which compounds of Formula 2 are preferably completely or at least substantially soluble and, in contrast, the compounds of Formula 3 and 4 have a low solubility in the volume of solvents used. Solvents that provide optimal product yields are those in which compounds of Formula 3 have a solubility in the range of about 20-100 mmol/L at ordinary ambient temperature (e.g., 25° C.). Examples of suitable solvents include alcohols, particularly lower alkanols, such as methanol and ethanol, amides such as N,N'-dimethylformamide, and halogenated and nonhalogenated aromatic hydrocarbons such as xylenes, toluene and chlorobenzene, and mixtures thereof. Solvents in which ethanol is the major component (e.g., at least 50%, 70% or 80% by weight) often provide superior results. Of particular note as a suitable organic solvent is ethanol or mixtures of ethanol with toluene or xylenes, or a combination thereof. If mixtures of ethanol and xylenes and/or toluene are used the ratio of the volume of ethanol to the volume of xylenes and/or toluene is typically in the range of about 5:1 to about 2:1. The total volume of the organic solvent used in the method of Scheme 1 is preferably between about 6 mL/g and about 15 mL/g relative to the weight of the compound of Formula 2 and more preferably between about 6 mL/g and about 10 mL/g to provide high concentration of reactants while maintaining stirrability.

The solvent can be added in various ways and times during the course of the reaction, such as, in one batch at the start of the reaction sequence, portionwise during the reaction sequence or intermittently during the course of adding one or more reagents. For example, one or more reagents can be dispersed, dissolved or partially dissolved in the suitable organic solvent and then added to the reaction mixture, which comprises one or more reagents and the suitable organic solvent. A preferred mode of addition involves adding the compound or compounds of Formula 4 as a slurry dispersed in the suitable organic solvent to a mixture comprising the compound of Formula 2, the compound or compounds of Formula 3, and the suitable organic solvent. The method of Scheme 1 is preferably conducted using oxygen-free solvent, because oxygen dissolved in the solvent can cause compounds of Formula 4 to oxidize, particularly when heated. Standard techniques can be used to obtain oxygen-free solvents including, for example, refluxing/distilling the solvents in an inert atmosphere (e.g., nitrogen or argon) (optionally in the presence of a drying agent such as sodium and benzophenone, potassium carbonate, magnesium sulfate), sparging the solvents with an inert gas (e.g., nitrogen or argon) or by freezing the solvents (using liquid nitrogen), applying a vacuum and then allowing the solvents to warm to room temperature. Additionally, the method of Scheme 1 is preferably conducted in an oxygen-free environment. Typically reducing the presence of atmospheric oxygen in the reaction vessel after all the reagents have been added is particularly advantageous. Standard techniques for obtaining an oxygen-free environment can be used including, for example, evacuating the reaction vessel using a vacuum pump and then repressurizing to atmospheric pressure with an inert gas (e.g., nitrogen or argon). This method can be repeated two or more times to further reduce the oxygen present in the reaction vessel. Repeating the evacuation/repressurization cycle three times using an applied vacuum of about 2-3 kPa typically effectively removes oxygen from the reaction vessel.

The reagents can be combined in a variety of orders, such as combining the compound of Formula 2, the compound or compounds of Formula 4, the compound or compounds of Formula 3, and then adding the suitable organic solvent. However, for preparing a compound of Formula 1 the most preferred order of addition has been found to comprise combining the compound of Formula 2, and the compound or compounds of Formula 3 with the suitable organic solvent to form a mixture, and then adding the compound or compounds of Formula 4 to the mixture. If a ligand such as triphenylphosphine or 1,5-cyclooctadiene is used in the method of Scheme 1, the order typically comprises combining the compound of Formula 2, the compound or compounds of Formula 3 and the ligand with the suitable organic solvent to form a mixture, and then adding the compound or compounds of Formula 4 to the mixture. The manner in which the components are added can influence the in situ mole ratios between the components present in the reaction mixture and affect product yield and purity. Thus, when preparing compounds of Formula 1, typically the optimal, in situ molar ratio of the compound or compounds of Formula 4 relative to the other components is achieved when Formula 4 is added to the reaction vessel in a controlled portionwise manner. The portionwise addition can be performed in several ways, but preferred is a method which comprises dispersing the compound or compounds of Formula 4 in the suitable organic solvent to form a slurry and then adding the slurry to the reaction vessel in portions. A convenient method for such portionwise addition involves adding over about 15 minutes a slurry of a Formula 4 compound or compounds in the reaction solvent (e.g., ethanol) in an amount providing a molar ratio of Formula 4 compounds to the alkali metal cyanide of Formula 3 of between about 0.005 to 1 and about 0.01 to 1. About 45 minutes to 2 h after completion of the first addition, a second equal portion of the slurry of Formula 4 compounds is similarly added. Further equal portions of the slurry are subsequently similarly added until the total desired amount of Formula 4 compounds has been added to the reaction mixture. Regardless of the mode of addition, the total amount of Formula 4 compounds added during the course of the reaction is as described above and in the Embodiments.

The present method is typically conducted at a temperature between about 10 and 100° C. and more typically between about 35 and 75° C. In the absence of added ligand, the most favorable reaction rates providing rapid conversion to compounds of Formula 1 in the highest yields and purity of are typically obtained with reaction temperatures ranging between about 40 and 45° C. To achieve reaction of the components in this temperature range, the components can be combined followed by warming to between about 40 and 45° C., or one or more of the components can be added to the reaction mixture at a temperature between about 40 and 45° C. For example, the compound or compounds of Formula 4 can be added portionwise as a slurry in the suitable organic solvent to the reaction mixture which is maintained at a temperature between about 40 and 45° C.

Compounds of Formula 1 can be isolated by standard techniques known in the art, including filtration, extraction, evaporation, and crystallization. As the compounds of Formula 1 are typically solids at ambient temperature, they are often most easily isolated by filtration, optionally followed by washing with water and/or an organic solvent (e.g., xylenes, toluene, ethanol). Additional product can be isolated by concentrating the filtrate under reduced pressure, slurrying the resulting residue in an organic solvent (e.g., xylenes, toluene, ethanol), filtering and optionally washing with water and/or an organic solvent (e.g., xylenes, toluene, ethanol). The solid product can be further purified by recrystallization from an appropriate organic solvent (e.g., ethanol, methanol, acetonitrile).

Depending on the reaction conditions and subsequent purification procedures, undesired nickel impurities including nickel(0) complexes may be present in the final products. The present invention provides a method for removing nickel impurities from a mixture thereof with compounds of Formula 1. The method comprises contacting the mixture with oxygen in the presence of an aqueous cyanide solution, thus forming water-soluble nickel complexes, which can most easily be separated from compounds of Formula 1 by filtration, and then washing the collected solid with water. In the present method, mixtures comprising nickel and a compound of Formula 1 can be contacted with oxygen in several ways, but the most convenient is by sparging the mixture comprising nickel, a compound of Formula 1 and an aqueous cyanide solution with air, or by simply exposing the mixture to air. A wide range of reagents serving as sources of a cyanide can be used to prepare the aqueous cyanide solution, but for reasons of availability and economy, the aqueous cyanide solution is preferably a mixture of water and KCN and/or NaCN. Typically, if a sufficient excess of an alkali metal cyanide of Formula 3 is used in the method of Scheme 1 no additional alkali metal cyanide is needed. For example, if the number of moles of the compound or compounds of Formula 3 used in the method of Scheme 1 is greater than the sum of the moles of compounds of Formulae 2 and 4, then nickel impurities can be removed from the crude reaction product simply by adding water to the crude solid mixture in an amount sufficient to suspend the solid, and then contacting the mixture with air while stirring. The nickel-free products then can be isolated by filtering the aqueous mixture and rinsing the collected solid with water. If the number of moles of the compound or compounds of Formula 3 used in the method of Scheme 1 is less than the sum of the moles of compounds of Formulae 2 and 4, then nickel impurities can be removed from the reaction products by adding an aqueous cyanide solution (e.g., aqueous solutions of KCN and/or NaCN) to the crude solid mixtures while exposing the mixtures to air, and then filtering the aqueous mixtures and rinsing the collected solid with water to isolate nickel-free products. The reaction temperature for this method is preferably between about 25 and 100° C., and usually the best results are obtained at about 45° C. The reaction is typically complete in about 1 to 2 h, although this time can vary depending on the rate of transfer of the oxidant (i.e. oxygen) into the reaction mixture. Oxygen transfer can be facilitated by stirring and agitation of the mixture. In some cases a change in color of the reaction mixture (e.g., from gray to white) indicates the reaction is complete.

The present method provides an efficient means to produce compounds of Formula 1 in typically high yields (e.g., about 80-85%), in about 10 to about 24 h. Of particular note is that the present method can be used to provide remarkably high yields of compounds of Formula 1 in excellent purity even though these compounds as well as the starting compounds of Formula 2 contain amino substituents and in some cases amide substituents that can potentially participate in side reactions. The method of Scheme 1 is illustrated in Examples 2 through 4 below.

As shown in Scheme 2, compounds of Formula 2 can be prepared by halogenation of compounds of Formula 6. Typically halogenation is achieved using a variety of halogenating reagents known in the art such as elemental halogen (e.g., $Cl_2$, $Br_2$, $I_2$), sulfuryl chloride, a N-halosuccinimide (e.g., N-chlorosuccinimide (NCS), N-bromosuccinimide (NBS), N-iodosuccinimide (NIS)) or halogenating reagents such as mixtures comprising hydrogen peroxide and a hydrogen halide. For leading references describing these methods, see PCT Patent Publications WO 2006/068669 (Scheme 11 and Example 1, Step E), WO 2003/015519 (Scheme 4 and Example 1, Step A), WO 2006/062978 (Scheme 15; Example 2, Step A; Example 4, Step B and Example 5, Step B), and WO 2004/067528 (Scheme 11 and Example 1, Step A).

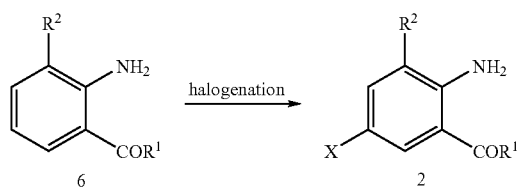

Scheme 2

Another method for preparing compounds of Formula 2 (wherein X is Br and $R^1$ is $NHR^3$) involves bromination of compounds of Formula 6 by treatment with a gas containing bromine, as described in PCT application PCT/US07/25800 and illustrated by the procedure of Reference Example 1.

Compounds of Formula 2 (wherein $R^1$ is $NHR^3$) can also be prepared by contacting an isatoic anhydride of Formula 7 with an alkyl amine of Formula 8 in the presence of a carboxylic acid as illustrated in Scheme 3.

Scheme 3

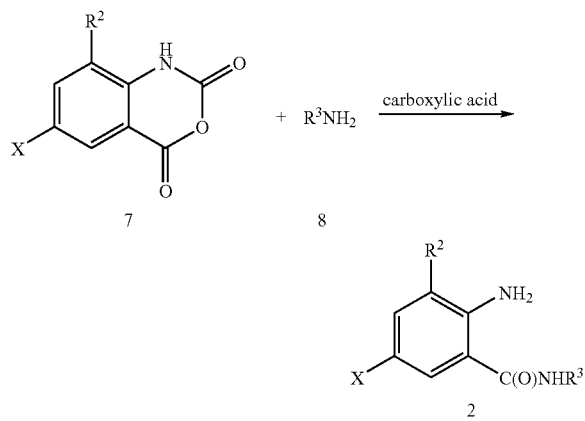

As amines such as the compound of Formula 8 are bases, in the absence of the carboxylic acid the mixture of the compounds of Formulae 7 and 8 would be basic (e.g., effective pH above 7). The carboxylic acid acts as a buffer to reduce the effective pH of the reaction mixture. A wide variety of carboxylic acids are useful, as the only requirement is for at least one carboxylic acid group to impart acidity. Other functional groups can be present, and more than one carboxylic acid group can be present on the carboxylic acid molecule. Typically the carboxylic acid has an effective $pK_a$ in the range of about 2 to about 5. Carboxylic acids include, for example, formic acid, propionic acid, chloroacetic acid, benzoic acid, phthalic acid, maleic acid, tartaric acid and citric acid. For reason of cost, inexpensive carboxylic acids such as formic acid, acetic acid, propionic acid and benzoic acid are preferred. Acetic acid, which is commercially available at low cost in its anhydrous form (known as "glacial acetic acid"), is particularly preferred.

The combination of the carboxylic acid with the basic amine of Formula 8 forms an amine salt of the carboxylic acid. This amine salt can be preformed before addition of the isatoic anhydride compound of Formula 7, or the amine salt can be generated in situ by metering the amine of Formula 8 into a mixture of the compound of Formula 7 and the carboxylic acid. For either mode of addition, maintaining the effective pH of the mixture during the reaction between about 3 and about 7 is generally best.

As the effective pH of the mixture results from the buffering effect of the carboxylic acid in combination with the amine of Formula 8, the effective pH can be adjusted according to the effective $pK_a$ of the carboxylic acid by adjusting the molar ratio of carboxylic acid to the amine of Formula 8. Typically the molar amounts of the amine of Formula 8 to carboxylic acid are in the range from about 0.8 to about 3. More particularly, when the mode of combination involves metering the amine of Formula 8 into a mixture of the isatoic anhydride compound of Formula 7 and carboxylic acid, the molar ratio of Formula 8 amine to carboxylic acid is preferably from about 0.95 to about 3. When the mode of combination involves forming the amine salt before addition of the compound of Formula 7 the molar ratio of Formula 8 amine to carboxylic acid is preferably from about 0.8 to about 1.05; as long as a nearly equimolar ratio (e.g., about 0.95 to about 1.05) of the Formula 8 amine to the carboxylic acid is used, the amine salt thus formed is typically used in a ratio of about 1.1 to about 5 molar equivalents relative to the compound of Formula 7. For optimal conversions, the molar ratio of amine of Formula 8 to isatoic anhydride compound of Formula 7 should be at least 1.0, although the molar ratio is preferred to be from about 1.1 to about 1.5 for reasons of efficiency and of economy, regardless of how the components are mixed. The molar amount of amine of Formula 8 relative to compound of Formula 7 can be substantially greater than 1.5, particularly when a nearly equimolar ratio (e.g., about 0.95 to about 1.05) of amine to acid is used.

Highest product yield and purity is achieved when the reaction medium is substantially anhydrous. The reaction medium is thus typically formed from substantially anhydrous compounds of Formula 7 and 8 and carboxylic acid. Preferably the reaction medium and forming materials contain about 5% or less, more preferably about 1% or less, and most preferably about 0.1% water or less (by weight). If the carboxylic acid is acetic acid, it is preferably in the form of glacial acetic acid.

The reaction of Scheme 3 is typically conducted in a liquid phase. In many cases the reaction can be carried out without solvent other than the compounds of Formulae 2, 7 and 8 and the carboxylic acid. But a preferred procedure involves use of a solvent that can suspend and at least partially dissolve the reactants. Preferred solvents are those which are non-reactive with the reaction components and have a dielectric constant of about 5 or greater, such as alkyl nitriles, esters, ethers, or ketones. Preferably the solvent should be substantially anhydrous to facilitate achieving a substantially anhydrous reaction medium. The weight ratio of solvent to the compound of Formula 7 is typically from about 1 to about 20, and preferably about 5 for reasons of efficiency and economy.

Carbon dioxide forms as a byproduct of the reaction of Scheme 3. Most of the carbon dioxide formed evolves from the reaction medium as a gas. The addition of the compound of Formula 7 into reaction medium containing the amine of Formula 8 or the addition of the amine of Formula 8 into the reaction medium containing the compound of Formula 7 is preferably conducted at such a rate and temperature as to facilitate controlling the evolution of carbon dioxide. The temperature of the reaction medium is typically between about 5 and 75° C., more typically between about 35 and 55° C.

The product of Formula 2 can be isolated by standard techniques known in the art, including pH adjustment, extraction, evaporation, crystallization, and chromatography. For example, the reaction medium can be diluted with about 3 to 15 parts by weight of water relative to the starting compound of Formula 8, the pH can be optionally adjusted with either acid or base to optimize the removal of either acidic or basic impurities, the water phase can be optionally separated, and most of the organic solvent can be removed by distillation or evaporation at reduced pressure. As the compounds of Formula 2 are typically crystalline solids at ambient temperature, they are generally most easily isolated by filtration, optionally followed by washing with water and then drying. The method of Scheme 3 is illustrated by Reference Example 2 for X being chlorine.

As shown in Scheme 4, isatoic anhydrides of Formula 7 can be prepared from anthranilic acids of Formula 2a (Formula 2 wherein $R^1$ is $OR^4$ and $R^4$ is H) via a cyclization reaction involving treatment of the anthranilic acids with phosgene or a phosgene equivalent such as triphosgene or an alkyl chloroformate (e.g., methyl chloroformate) in a suitable solvent such as toluene or tetrahydrofuran. The method is described in PCT Patent Publication WO 2006/068669, including a specific example relevant to Scheme 4. Also see Coppola, *Synthesis* 1980, (7), 505-536 and Fabis et al., *Tetrahedron* 1998, 54(36), 10789-10800.

Scheme 4

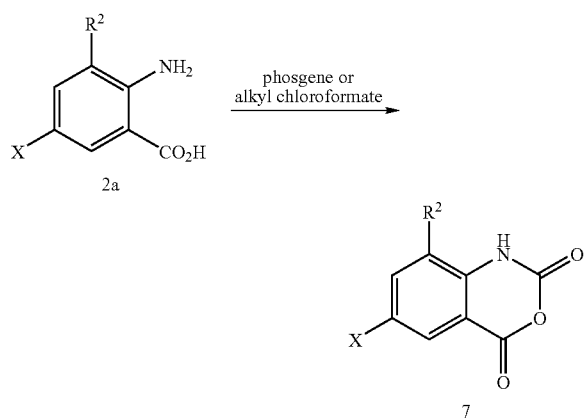

In another aspect of the present invention a compound of Formula 4 is prepared by the method comprising contacting at least one compound of the Formula 9, at least one metal reducing agent and dichlorobis(triphenylphosphine)nickel (Formula 10) as shown in Scheme 5.

Scheme 5

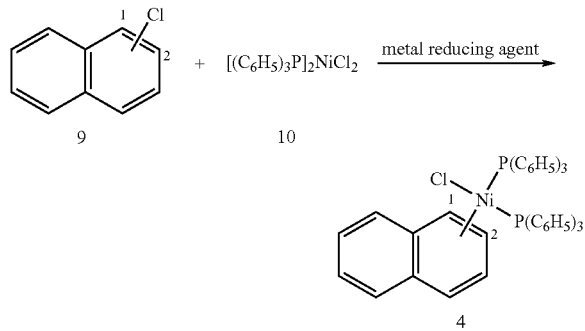

In the method of Scheme 5, Formula 9 can be 1-chloronaphthalene or a mixture of 1-chloro- and 2-chloronaphthalene. The compound or compounds of Formula 9 are most conveniently obtained from a commercial source. A variety of commercial suppliers offer 1-chloronaphthalene, although it is often available only as an isomeric mixture of 1-chloro- and 2-chloronaphthalene. For example, Fisher Scientific (Pittsburgh, Pa.) and Aldrich Chemical (Milwaukee, Wis.) supply technical grade 1-chloronaphthalene as a 90:10 mixture of the 1- and 2-isomers. One skilled in the art will recognize that mixtures of 1-chloro- and 2-chloronaphthalene can be separated to isolate the 1-chloro isomer. However, in the method of Scheme 5 it is most convenient to use 1-chloronaphthalene obtained from a commercial source without separation of the isomers. If a mixture of 1-chloro- and 2-chloronaphthalene is used preferably the mixture contains at least about 80 percent 1-chloronaphthalene, and more preferably at least about 90 percent. Regardless of whether a single isomer (i.e. 1-chloronaphthalene) or a mixture of isomers is used, the total molar ratio of Formula 9 with respect to the compound of Formula 10 is typically from about 1 to about 3, and preferably from about 2 to about 2.5, and most preferably from about 2 to about 2.1.

Dichlorobis(triphenylphosphine)nickel (Formula 10) is commercially available and can also be made from commercially available starting materials such as nickel(II) chloride hexahydrate and triphenylphosphine; see, for example, Brandsma et al., *Synthetic Communications* 1990, 20(20), 3153-3156. Regardless of whether the dichlorobis-(triphenylphosphine)nickel (Formula 10) is obtained from a commercial source or synthesized, its molar ratio used in the present method relative to Formula 9 is typically from about 0.3 to about 1, and preferably from about 0.4 to about 0.5.

The metal reducing agent in the present method is, for example, zinc or manganese, and preferably zinc. If elemental zinc is used as the metal reducing agent most preferred are molar ratios from about 1 to about 5 relative to the compound or compounds of Formula 9, and more preferred are ratios from about 1 to about 2.

The method of Scheme 5 is typically conducted in a suitable organic solvent. Suitable organic solvents include a variety of polar organic solvents which are inert to the metal reducing agent. The term polar organic solvent in the context of the present method means an organic solvent very soluble or miscible in water. Polar organic solvents include alcohols, particularly lower alkanols, such as methanol and ethanol, ethers such as tetrahydrofuran and p-dioxane, amides such as N,N-dimethylformamide and N,N-dimethylacetamide, and nitriles such as acetonitrile. Of particular note as a solvent is ethanol, which provides high yields of Formula 4 compounds. Typically oxygen-free solvents are used, because the compounds of Formula 4 can react with atmospheric oxygen present in the reaction solvent. Techniques for obtaining oxygen-free solvents include those already discussed for the method of Scheme 1.

For preparing a compound of Formula 4 the preferred order of addition comprises adding the compound of Formula 10 to a mixture of at least one metal reducing agent, at least one compound of Formula 9, and the suitable organic solvent. Further preferred as a mode of addition is adding a slurry of the compound of Formula 10 in the suitable organic solvent to a mixture of at least one metal reducing agent, at least one compound of Formula 9, and the suitable organic solvent. As the addition of the compound of Formula 10 to the reaction mixture causes an exothermic reaction, for either mode of addition described above, the rate of addition is preferably such that the temperature of the reaction mixture is maintained between about 25 and 80° C., and more preferably between about 50 and 70° C. Depending on the rate of addition of the compound of Formula 10, the reaction mixture can become very thick with solids; a rate of addition such that the reaction temperature is maintained as described above alleviates this problem and provides a stirrable mixture (i.e. stirrable by conventional means), which maximizes product yield and the purity. The reaction times vary depending on temperature, but typically when the temperature of the reaction mixture is between about 50 and 80° C. the reaction is complete in 1 h.

In the reaction of Scheme 5 the product obtained is chloro-1-naphthalenylbis-(triphenylphosphine)nickel or a mixture of 1- and 2-isomers of chloronaphthalenylbis-(triphenylphosphine)nickel depending on the starting material of Formula 9. Regardless of the isomeric composition, Formula 4 products can be isolated by standard techniques known in the art, including filtration, extraction, evaporation, and crystallization. For example, as the compounds of Formula 4 are crystalline at ambient temperature, after cooling the reaction mixture the products can be collected by filtration. Optionally the collected solid products can be washed with water, a dilute aqueous acid solution and an organic solvent, and dried.

The present method provides a means of efficiently producing compounds of Formula 4 in typically high yields (e.g., about 90-95%), in about 1 to about 2 h. A notable feature of this method is that the order of addition of reagents can be used to provide better control of reaction exothermicity than previously known processes for the production of these compounds. Furthermore, the preferred order of addition of the compound of Formula 10 allows for convenient control of the reaction temperature and provides reaction mixtures that are easily stirred by conventional means. These features make this method especially suitable for large-scale commercial manufacturing. The method of Scheme 5 is illustrated in Example 1 below.

In another aspect of the present invention compounds of the Formula 1 prepared by the method of Scheme 1 are useful as intermediates for preparing compounds of Formula 5. Compounds of Formula 5 are useful as insecticides, as described, for example, in PCT Patent Publications WO 2003/015518 and WO 2006/055922.

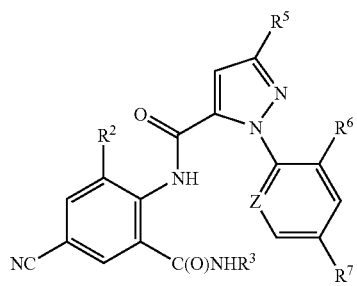

wherein
R² is CH₃ or Cl;
R³ is H, C₁-C₄ alkyl, cyclopropyl, cyclopropylcyclopropyl, cyclopropylmethyl or methylcyclopropyl;
Z is CR⁸ or N;
R⁵ is Cl, Br, CF₃, OCF₂H or OCH₂CF₃;
R⁶ is F, Cl or Br;
R⁷ is H, F or Cl; and
R⁸ is H, F, Cl or Br.

A variety of routes are possible for the preparation of a compound of Formula 5 from a compound of Formula 1. As outlined in Scheme 6, one such method involves the coupling of a compound of Formula 1a (Formula 1 wherein R¹ is OR⁴ and R⁴ is H) with a pyrazole-5-carboxylic acid of Formula 11, resulting in a cyanobenzoxazinone of Formula 12. Subsequent reaction of the cyanobenzoxazinone with an amine of Formula 8 provides a compound of Formula 5. Conditions for the first step involve sequential addition of methanesulfonyl chloride in the presence of a tertiary amine such as triethylamine or pyridine to a pyrazole of Formula 11, followed by the addition of a compound of Formula 1a, followed by a second addition of tertiary amine and methanesulfonyl chloride. The reaction can be run neat or in a variety of suitable solvents including tetrahydrofuran, diethyl ether, dioxane, toluene, dichloromethane or chloroform with optimum temperatures ranging from room temperature to the reflux temperature of the solvent. The second step, reaction of benzoxazinones with amines to produce anthranilamides, is well documented in the chemical literature. For a general review of benzoxazinone chemistry see Jakobsen et al., *Biorganic and Medicinal Chemistry* 2000, 8, 2095-2103 and references cited within. Also see G. M. Coppola, *J. Heterocyclic Chemistry* 1999, 36, 563-588. Further, see PCT Patent Publication WO 2004/067528, which teaches the general method shown in Scheme 6, including experimental examples relevant to Scheme 6.

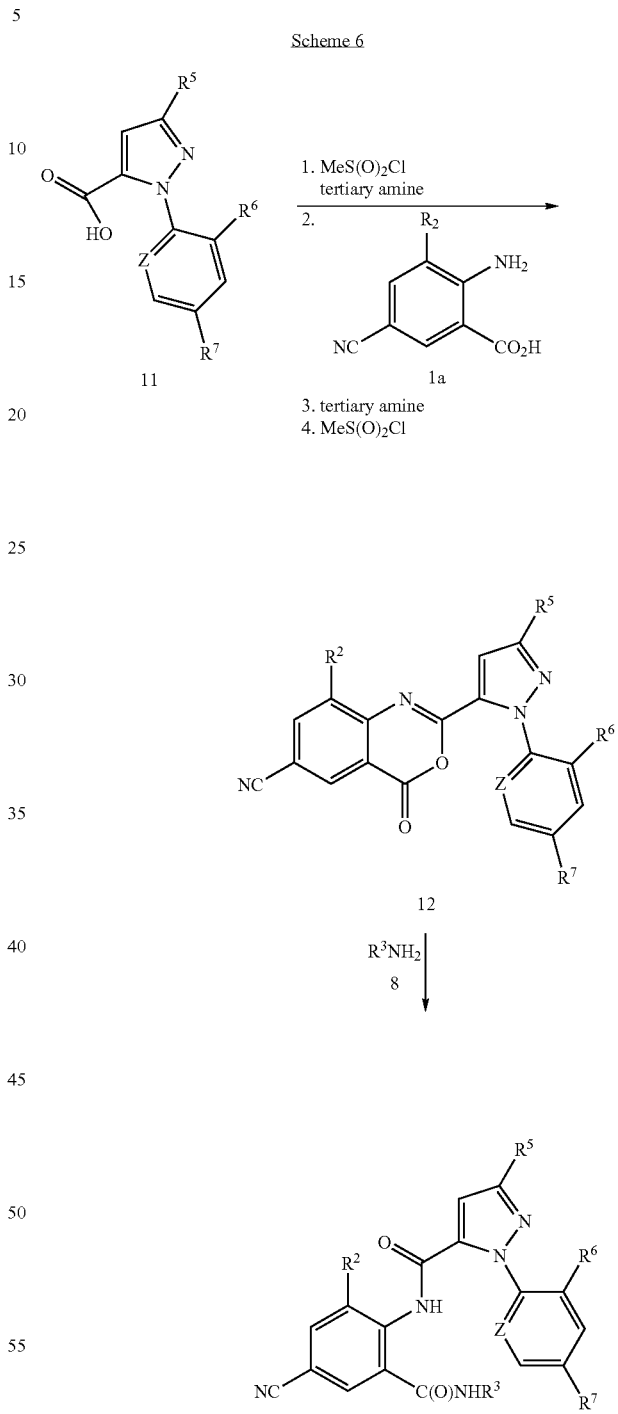

Another method of preparing compounds of Formula 5 is shown in Scheme 7. In this method a compound of Formula 5 is prepared by combining a compound of Formula 1b (Formula 1 wherein R¹ is NHR³), a pyrazole of Formula 11 and sulfonyl chloride according to the general method taught in PCT Patent Publication WO 2006/062978, which is hereby incorporated herein in its entirety by reference.

Scheme 7

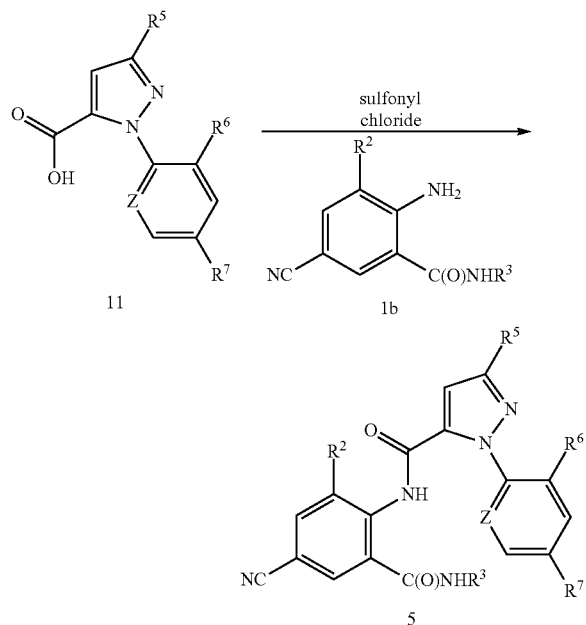

As described in WO 2006/062978 a variety of reaction conditions are possible for this transformation. Typically a sulfonyl chloride is added to a mixture of the compounds of Formulae 1b and 11 in the presence of a solvent and a base. Sulfonyl chlorides are generally of the formula $RS(O)_2Cl$ wherein R is a carbon-based radical. Typically for this method R is $C_1$-$C_4$ alkyl, $C_1$-$C_2$ haloalkyl, or phenyl optionally substituted with 1-3 substituents independently selected from the group consisting of halogen, $C_1$-$C_3$ alkyl, and nitro. Commercially available sulfonyl chlorides include methanesulfonyl chloride (R is $CH_3$), propanesulfonyl chloride (R is $(CH_2)_2CH_3$), benzenesulfonyl chloride (R is phenyl), and p-toluenesulfonyl chloride (R is 4-methylphenyl). Methanesulfonyl chloride is of note for reasons of lower cost, ease of addition and/or less waste. At least one molar equivalent of the sulfonyl chloride per mole of the compound of Formula 11 is stoichiometrically needed for complete conversion. Typically the molar ratio of sulfonyl chloride to the compound of Formula 11 is no more than about 2.5, more typically no more than about 1.4.

The compound of Formula 5 is formed when the starting compounds of Formulae 1b, 11 and the sulfonyl chloride are contacted with each other in a combined liquid phase, in which each is at least partially soluble. Since the starting materials of Formulae 1b and 11 are typically solids at ordinary ambient temperatures, the method is most satisfactorily conducted using a solvent in which the starting compounds have significant solubility. Thus typically the method is conducted in a liquid phase comprising a solvent. In some cases the carboxylic acid of Formula 11 may have only slight solubility, but its salt with added base may have more solubility in the solvent. Suitable solvents for this method include nitriles such as acetonitrile and propionitrile; esters such as methyl acetate, ethyl acetate and butyl acetate; ketones such as acetone, methyl ethyl ketone (MEK) and methyl butyl ketone; haloalkanes such as dichloromethane and trichloromethane; ethers such as ethyl ether, methyl tent-butyl ether, tetrahydrofuran (THF) and p-dioxane; aromatic hydrocarbons such as benzene, toluene, chlorobenzene and dichlorobenzene; tertiary amines such as trialkylamines, dialkylanilines and optionally substituted pyridines; and mixtures of the foregoing. Solvents of note include acetonitrile, propionitrile, ethyl acetate, acetone, MEK, dichloromethane, methyl tent-butyl ether, THF, p-dioxane, toluene and chlorobenzene. Of particular note as the solvent is acetonitrile, as it often provides products in superior yield and/or purity.

As the reaction of the present method generates hydrogen chloride as a byproduct, which would otherwise bind to basic centers on the compounds of Formulae 1b, 5 and 11, the method is most satisfactorily conducted in the presence of at least one added base. The base can also facilitate constructive interaction of the carboxylic acid with the sulfonyl chloride compound and the anthranilamide. Reaction of an added base with the carboxylic acid of Formula 11 forms a salt, which may have greater solubility than the carboxylic acid in the reaction medium. Although the base may be added at the same time, in alternation, or even after the addition of the sulfonyl chloride, the base is typically added before the addition of the sulfonyl chloride. Some solvents such as tertiary amines also serve as bases, and when these are used as solvents they will be in large stoichiometric excess as bases. When the base is not used as the solvent the nominal mole ratio of the base to the sulfonyl chloride is typically from about 2 to about 2.2, and is preferably from about 2.1 to about 2.2. Preferred bases are tertiary amines, including substituted pyridines. More preferred bases include 2-picoline, 3-picoline, 2,6-lutidine and pyridine. Of particular note as the base is 3-picoline, as its salts with carboxylic acids of Formula 11 are often highly soluble in solvents such as acetonitrile.

The compounds of Formula 5 can be isolated from the reaction mixtures by methods known to those skilled in the art, including crystallization, filtration, and extraction. PCT Patent Publication WO 2006/062978 discloses specific examples relevant to the method of Scheme 7. Also, the method of Scheme 7 is illustrated in Example 5 below.

Pyrazole-5-carboxylic acids of Formula 11 wherein $R^5$ is halogen (e.g., Cl or Br) can be prepared from 5-oxo-3-pyrazolidinecarboxylates by treatment with a halogenating agent to give 3-halo-4,5-dihydro-1H-pyrazole-5-carboxylates, which can subsequently be treated with an oxidizing agent to provide esters of the acids of Formula 11. The esters can then be converted to the corresponding acids. Halogenating agents that can be used include, for example, phosphorous oxyhalides, phosphorous trihalides, phosphorous pentahalides, thionyl chloride, dihalotrialkylphosphoranes, dihalodiphenylphosphoranes, oxalyl chloride and phosgene. Oxidizing agents which can be used include, for example, hydrogen peroxide, organic peroxides, potassium persulfate, sodium persulfate, ammonium persulfate, potassium monopersulfate (e.g., Oxone®) and potassium permanganate. See PCT Patent Publications WO 2003/016283, WO 2004/087689, and WO 2004/011453 for a description of the halogenation and oxidation methods, and a procedure for preparing the starting 5-oxo-3-pyrazolidinecarboxylates. To convert the esters to carboxylic acids a variety of useful methods reported in the chemical literature can be used, including nucleophilic cleavage under anhydrous conditions or hydrolysis involving the use of either acids or bases (see T. W. Greene and P. G. M. Wuts, *Protective Groups in Organic Synthesis*, 2nd ed., John Wiley & Sons, Inc., New York, 1991, pp. 224-269 for a review of methods). Base-catalyzed hydrolytic methods are preferred to prepare the carboxylic acids of Formula 11 from the corresponding esters. Suitable bases include alkali metal hydroxides (comprising lithium, sodium or potassium metals). For example, the ester can be dissolved in a mixture of water and alcohol such as methanol. Upon treatment with sodium hydroxide or potassium hydroxide, the ester saponifies to provide the sodium or potassium salt of the carboxylic acid. Acidification with a strong acid, such as hydrochloric acid or sulfuric acid, gives the carboxylic acids. PCT Patent Publication WO 2003/016283 provides a relevant experimental example for the conversion of an ester to an acid illustrating the base-catalyzed hydrolysis method.

Alternatively, pyrazole-5-carboxylic acids of Formula 11 can be prepared from 4,5-di-hydro-5-hydroxy-1H-pyrazole-5-carboxylates via an acid-catalyzed dehydration reaction to give esters, which can then be converted to the acids of Formula 11. Typical reaction conditions involve treatment of 4,5-dihydro-5-hydroxy-1H-pyrazole-5-carboxylates with an acid, for example, sulfuric acid, in an organic solvent, such as acetic acid, at temperatures between 0 and 100° C. The method is described PCT Publication WO 2003/016282. Conversion of the esters to acids can be done using the methods described above. Also, WO 2003/016282 provides a relevant experimental example for the conversion of an ester to an acid.

Anthranilic amides of Formula 1b can also be prepared from the corresponding acids or esters of Formula 1c (Formula 1 wherein $R^1$ is $OR^4$ and $R^4$ is H or $C_1$-$C_4$ alkyl) as shown below in Scheme 8. Forming amides from carboxylic acids typically involves addition of a coupling agent (e.g., silicon tetrachloride, or alternatively dicyclohexylcarbodiimide or 1-ethyl-3-(3-dimethylaminopropyl)carbodiimide often in the presence of 1-hydroxy-benzotriazole). Preparation of anthranilic amides from anthranilic acids is disclosed in M. J. Kornet, *Journal of Heterocyclic Chemistry* 1992, 29(1), 103-5; PCT Patent Publication WO 2001/66519-A2; T. Asano et al., *Bioorganic & Medicinal Chemistry Letters* 2004, 14(9), 2299-2302; H. L. Birch et al., *Bioorganic & Medicinal Chemistry Letters* 2005, 15(23), 5335-5339; and D. Kim et al., *Bioorganic & Medicinal Chemistry Letters* 2005, 15(8), 2129-2134. Also T. Asano et al. reports preparation of an anthranilic amide from an anthranilic acid through an N-protected aniline intermediate or through a 4H-3,1-benzoxazine-2,4(1H)-dione (isatoic anhydride) intermediate. Forming amides from esters often involves heating the ester with the appropriate amine in a polar solvent such as ethylene glycol. A procedure useful for conversion of anthranilic esters to anthranilic amides is described in PCT Patent Publication WO 2006/062978. Also, E. B. Skibo et al., *Journal of Medicinal Chemistry* 2002, 45(25), 5543-5555 discloses the preparation of an anthranilic amide from the corresponding anthranilic ester using sodium cyanide catalyst.

Scheme 8

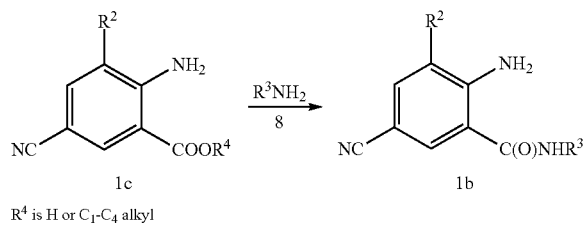

$R^4$ is H or $C_1$-$C_4$ alkyl

The methods of Schemes 6 and 7 are illustrative of just two of many methods for converting a compound of Formula 1 to a carboxamide of Formula 5. A wide variety of general methods are known in the art for preparing carboxamides from carboxylic acids and amines. For a general review, see M. North, *Contemporary Org. Synth.* 1995, 2, 269-287. Particular methods include contacting a compound of Formula 1b with a compound of Formula 11 in the presence of a dehydrating coupling agent such as 1,1'-carbonyldiimidazole, bis (2-oxo-3-oxazolidinyl)phosphinic chloride or benzotriazol-1-yloxy-tris(dimethylamino)phosphonium hexafluorophosphate, or a polymer-bound analogous reagent such as polymer-bound dicyclohexylcarbodiimide, typically in an inert solvent such as dichloromethane or N,N-dimethylformamide, as is generally disclosed in PCT Patent Publication WO 2003/15518. Also disclosed in WO 2003/15518 is a method for preparing an acyl chloride derivative of the compound of Formula 11 by contacting the Formula 11 compound with thionyl chloride or oxalyl chloride in the presence of a catalytic amount of N,N-dimethylformamide, and then contacting the derived acyl chloride with the compound of Formula 1b in the presence of an acid scavenger, such as an amine base (e.g., triethylamine, N,N-diisopropylethylamine, pyridine, and polymer-supported analogs) or a hydroxide or carbonate (e.g., NaOH, KOH, $Na_2CO_3$, $K_2CO_3$), typically in an inert solvent such as tetrahydrofuran, 1,4-dioxane, ethyl ether or dichloromethane. The product, a compound of Formula 5, can be isolated from the reaction mixtures by methods known to those skilled in the art, including crystallization, filtration and extraction.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. In the following Examples, the term "oxygen-free" when used in connection with a solvent refers to a solvent in which atmospheric oxygen was removed before use by a technique involving heating the solvent at reflux while applying a moderate vacuum, and then pressurizing the flask containing the solvent with nitrogen. In Examples 1-4, after all the reagents had been added, the reaction vessels were evacuated of oxygen using a vacuum pump and then the vessels were repressurized to atmospheric pressure using nitrogen gas. Typically the evacuation/repressurization cycle was repeated three times with an applied vacuum. $^1$H NMR spectra are reported in ppm downfield from tetramethylsilane; means singlet, d means doublet, m means multiplet and br s means broad singlet.

Reference Example 1

Preparation of 2-amino-5-bromo-N,3-dimethylbenzamide (a compound of Formula 2)

A 1000-mL flask equipped with a mechanical stirrer, thermocouple, condenser and Teflon® fluoropolymer tubing (0.16 cm I.D.×0.32 cm O.D. or 1/16" I.D.×1/8" O.D.) (positioned such that the end of the tubing was submerged below the surface of the reaction mixture) was charged with acetic acid (226 mL). A solution of aqueous sodium hydroxide (50%, 25 g) in water (85 g) was added over 15 minutes, and then 2-amino-N,3-dimethylbenzamide (50 g, 0.305 mol) (see PCT Publication WO 2006/062978 for a method of preparation) was added and the mixture was heated at 55° C. A two-necked 200-mL flask fitted on one neck with a dip tube was charged with liquid bromine (50.1 g), and the other neck was connected to the Teflon® tubing on the 1000-mL flask. Nitrogen gas was then flowed through the dip tube below the surface of the liquid bromine at a rate of about 0.012 m$^3$ (0.4 cu ft) per h for 2.5 h, during which time bromine vapor entrained in the nitrogen gas flowed out of the two-necked 200-mL flask and entered the reaction mixture through the Teflon® tubing. Then the reaction temperature was held at about 55° C. during the bromine vapor addition and for 30 minutes thereafter, and then cooled to 45° C. and stirred overnight. A solution of aqueous sodium hydroxide (50%, 52 g) in water (88 mL) was added to the reaction mixture at a rate of 0.8 mL/minute. After about 10% of the total volume of the sodium hydroxide solution had been added, the addition was stopped and the reaction mixture was stirred for 1 h at 45° C. After 1 h the remaining sodium hydroxide solution was added at a rate of 0.8 mL/minute. After the addition was complete, the reaction mixture was stirred for 30 minutes at 45° C., and then cooled to 10° C. and stirred for 1 h. The mixture was filtered and the solid collected was washed with methanol (130 mL) and water (260 mL), and then dried to a constant weight in a vacuum-oven at 45° C. to give the title compound as a solid (67 g, 99.4 area % purity by HPLC, 89.7% yield) melting at 133-135° C.

$^1$H NMR (DMSO-d$_6$) δ 8.30 (m, 1H), 7.49 (d, 1H), 7.22 (d, 1H), 6.35 (br s, 2H), 2.70 (d, 3H), 2.06 (s, 3H).

Reference Example 2

Preparation of
2-amino-5-chloro-N,3-dimethylbenzamide (a
compound of Formula 2)

A 300-mL flask equipped with a thermometer and nitrogen bubbler was charged with ethyl acetate (100 mL) and acetic acid (12.6 g, 0.21 mol). Anhydrous methylamine (6.3 g, 0.20 mol) was added below the surface of the liquid mixture, which was cooled to maintain the temperature below 35° C., and then 6-chloro-8-methyl-2H-3,1-benzoxazine-2,4(1H)-dione (21 g, 0.10 mol) (see Scheme 4 for a method of preparation) was added in portions while maintaining the reaction mixture at 35-40° C. After completion of the addition of the 6-chloro-8-methyl-2H-3,1-benzoxazine-2,4(1H)-dione the temperature was maintained at 40-45° C., and the progress of the reaction was monitored by HPLC analysis. When analysis of the reaction mixture indicated no more than 0.5% of the 6-chloro-8-methyl-2H-3,1-benzoxazine-2,4(1H)-dione remained (about 20 minutes), water (50 mL) was added to the reaction mixture. A distillation head was attached, moderate vacuum was applied, and ethyl acetate was distilled out at an internal temperature of about 46-60° C. and pressure of about 30 to 50 kPa. To replace the ethyl acetate removed by distillation, water was added to maintain the original liquid volume in the reactor. When a significant amount of water began to distill, the aqueous slurry was cooled to 10° C. The solid was collected by filtration and dried at 60° C. and 13.3 kPa to afford the title compound as a white crystalline solid (19 g, ca. 95% yield, above 98% purity by peak area in HPLC analysis).

Example 1

Preparation of a mixture of chloro-1-naphthalenylbis
(triphenylphosphine)nickel and chloro-2-naphthalenylbis(triphenylphosphine)nickel (compounds of
Formula 4)

To a stirred mixture of zinc (325 mesh, 12 g, 0.185 mol) in oxygen-free ethanol (136 mL) at 70° C. was added 1-chloronaphthalene (Fisher Scientific, approximately a 90:10 mixture of 1- and 2-isomers 30 g, 0.185 mol). A slurry of dichlorobis-(triphenylphosphine)nickel (60 g, 0.091 mol) in oxygen-free ethanol (136 mL) was added over 30 minutes to the reaction mixture maintained at 65° C. After the addition was complete, the stirred reaction mixture was maintained at 65° C. for 1 h. The reaction mixture was cooled to 20° C., and hydrochloric acid (30%, 72 mL) was added dropwise at such a rate that the temperature of the mixture remained between 20 and 30° C. After the addition was complete the reaction mixture was stirred at 25° C. for 1 h, after which time hydrogen evolution ceased. The reaction mixture was filtered, and the solid collected was washed successively with ethanol (180 mL), hydrochloric acid (1N, 2×180 mL), ethanol (2×180 mL), and hexanes (180 mL). The solid was dried in a vacuum-oven at 50° C. overnight to give the mixture of title compounds as a dark-yellow solid (62.1 g, 90.8% yield) melting at 147° C. with apparent decomposition.

IR (nujol): 1481, 1434, 1306, 1243, 1186, 1095, 1027, 999 cm$^{-1}$.

Example 2

Preparation of
2-amino-5-cyano-N,3-dimethylbenzamide (a
compound of Formula 1)

A stirred mixture of 2-amino-5-bromo-N,3-dimethylbenzamide (prepared by the method of Reference Example 1) (20.0 g, 0.082 mol), potassium cyanide (10.4 g, 0.159 mol) and oxygen-free ethanol (60 mL) was heated at 45° C. A slurry of chloronaphthalenylbis(triphenylphosphine)nickel (i.e. the product of Example 1, a mixture of 1- and 2-isomers) (4.01 g, 5.36 mmol) in oxygen-free ethanol (60 mL) was added in four portions to the reaction mixture. Each addition was completed in about 18 minutes, and after the first addition subsequent additions were begun approximately 50, 75, and 105 minutes after the previous addition was complete. Oxygen-free ethanol (15 mL) was added to the reaction mixture after the second addition to facilitate stirring. After the fourth addition was complete, the reaction mixture was stirred for 5.7 h at 45° C., and then more chloro-naphthalenylbis(triphenylphosphine)nickel (0.5 g, 0.67 mmol) in oxygen-free ethanol (10 mL) was added over 10 minutes. After stirring overnight at 45° C., toluene (100 mL) was added, and the solvent was evaporated under reduced pressure. More toluene (150 mL) was added, and the solvent was again evaporated under reduced pressure. The resulting solid was slurried in toluene (120 mL), filtered, and washed with toluene (100 mL) and water (2×70 mL). The solid was dried overnight in a vacuum-oven at 50° C. to give the title compound as a white solid (12.68 g, 81.8% yield). A portion of the product was recrystallized from acetonitrile to give an analytical sample melting at 204.0-204.5° C.

$^1$H NMR (DMSO-d$_6$) δ 8.44 (s, 1H), 7.81 (s, 1H), 7.43 (s, 1H), 7.17 (s, 2H), 2.73 (d, 3H), 2.09 (s, 3H).

Example 3

A Second Preparation of
2-amino-5-cyano-N,3-dimethylbenzamide

A stirred mixture of 2-amino-5-bromo-N,3-dimethylbenzamide (prepared by the method of Reference Example 1) (20.0 g, 0.082 mol), potassium cyanide (10.4 g, 0.159 mol), triphenylphosphine (0.28 g, 1.07 mmol) and oxygen-free ethanol (60 mL) was heated at 45° C. A slurry of chloronaphthalenylbis(triphenylphosphine)nickel (i.e. the product of Example 1, a mixture of 1- and 2-isomers) (4.0 g, 5.35 mmol) in oxygen-free ethanol (60 mL) was added in four portions to the reaction mixture. Each addition was completed in about 15 minutes. After the first addition subsequent additions were begun approximately 75 minutes after the previous addition was complete. Oxygen-free ethanol (15 mL) was added to the reaction mixture prior to the third addition to facilitate stirring. After the fourth addition was complete, the reaction mixture was stirred for 1.25 h at 45° C., and then more chloronaphthalenylbis(triphenylphosphine)nickel (0.5 g, 0.67 mmol) in oxygen-free ethanol (10 mL) was added over 10 minutes. After stirring for another 1.5 h at 45° C., gas chromatography analysis of the reaction mixture indicated about 96% conversion of the 2-amino-5-bromo-N,3-dimethylbenzamide with 2-amino-5-cyano-N,3-dimethyl-benzamide being the major product. After stirring at 45° C. overnight, xylenes (50 mL) were added and the mixture was heated at 75° C. After 1 h the mixture was cooled to 25° C. and filtered (forming a wet cake). The filtrate was evaporated under reduced pressure, and the residue was slurried in xylenes (40 mL) and then filtered through the previously obtained wet cake. The wet cake was rinsed with xylenes (2×30 mL) and then suspended in water (120 ml) and heated for 1 h at 45° C. while exposed to air. After cooling to 25° C., the mixture was filtered, and the solid was washed with water (2×30 mL) and then dried in a vacuum-oven overnight at 50° C. to give the title compound as a white solid (13.7 g, 88% yield).

$^1$H NMR spectrum was the same as reported for the product of Example 2.

Example 4

A Third Preparation of 2-amino-5-cyano-N,3-dimethylbenzamide

A stirred mixture of 2-amino-5-chloro-N,3-dimethylbenzamide (prepared by the method of Reference Example 2) (32.6 g, 0.164 mol), potassium cyanide (ground prior to use, 16 g, 0.246 mol), triphenylphosphine (0.56 g, 2.13 mmol), oxygen-free ethanol (100 mL) and xylenes (40 mL) was heated at 45° C. A slurry of chloronaphthalenylbis(triphenylphosphine)nickel (i.e. the product of Example 1, a mixture of 1- and 2-isomers) (12 g, 16 mmol) in oxygen-free ethanol (100 mL) was added in six portions to the reaction mixture. Each addition was completed in about 15 minutes. The second addition was begun about 45 minutes after the first addition was complete, and all subsequent additions were added about 105 minutes after the previous addition was complete. After the reaction mixture was stirred overnight at 45° C., gas chromatography analysis indicated about 95.3% conversion of the 2-amino-5-chloro-N,3-dimethylbenzamide with 2-amino-5-cyano-N,3-dimethylbenz-amide being the major product. Oxygen-free ethanol (40 mL) was added to the reaction mixture, and the mixture was heated at 75° C. After 1 h the mixture was cooled to 25° C. and filtered to form a wet cake, which was washed with xylenes (30 mL). The filtrate was evaporated under reduced pressure, and xylenes (30 mL) heated to 50° C. were added to the residue. After cooling to 25° C., the mixture was filtered through the previously obtained wet cake, which was rinsed with xylenes (2×40 mL). The wet cake was suspended in water (240 mL), and the suspension heated for 1 h at 45° C. while being exposed to air. After cooling to 25° C., the mixture was filtered, and the solid was dried in a vacuum-oven overnight at 50° C. to give the title compound as a white solid (25.6 g, 82.5% yield, above 95% purity by HPLC analysis).

$^1$H NMR spectrum was the same as reported for the product of Example 2.

Example 5

Preparation of 3-bromo-1-(3-chloro-2-pyridinyl)-N-[4-cyano-2-methyl-6-[(methylamino)carbonyl]phenyl]-1H-pyrazole-5-carboxamide (a compound of Formula 5)

To a mixture of 3-bromo-1-(3-chloro-2-pyridinyl)-1H-pyrazole-5-carboxylic acid (see PCT Patent Publication WO 2003/015519 for a method of preparation) (99.0% purity, 3.03 g, 0.01 mol) and 2-amino-5-cyano-N,3-dimethylbenzamide (prepared by the method of Example 2) (1.99 g, 0.01 mol) in acetonitrile (16 mL) was added 3-picoline (2.92 mL, 0.03 mol). Methanesulfonyl chloride (1.08 mL, 0.014 mol) was added dropwise to the reaction mixture at 20 to 25° C. After stirring for 3 h, water (7.5 mL) was added dropwise to the reaction mixture while maintaining the temperature between 20 to 25° C. After 15 minutes, concentrated hydrochloric acid (0.5 mL) was added and the reaction mixture was stirred for 1 h at 20 to 25° C. The mixture was filtered and the solids collected were washed with acetonitrile-water (87:13 mixture by volume, 2×2 mL) and then with water (2×2 mL), and then dried under nitrogen to afford the title compound (4.80 g, 92.6% corrected yield based on a water-free assay of 96.6%) as an off-white solid melting at 206-208° C.

$^1$H NMR (DMSO-d$_6$) δ 10.52 (br s, 1H) 8.50 (dd, 1H), 8.36 (m, 1H), 8.17 (dd, 1H), 7.88 (d, 1H), 7.76 (d, 1H), 7.62 (m, 1H), 7.41 (s, 1H), 2.66 (d, 3H), 2.21 (s, 3H).

Table 1 illustrates the particular transformations to prepare compounds of Formula 1 according to the method of the present invention. In Table 1 and the following tables: t means tertiary, s means secondary, n means normal, i means iso, c means cyclo, Me means methyl, Et means ethyl, Pr means propyl, and Bu means butyl. Concatenations of groups are abbreviated similarly; for example, "c-PrCH$_2$" means cyclopropylmethyl.

TABLE 1

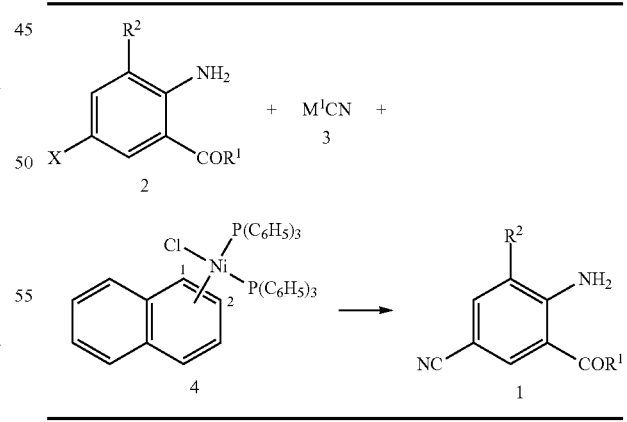

| R$^1$ is NHR$^3$, X is Br amd M$^1$ is K. | |
|---|---|
| R$^2$ | R$^3$ |
| Me | H |
| Me | Me |
| Me | Et |
| Me | n-Pr |

TABLE 1-continued

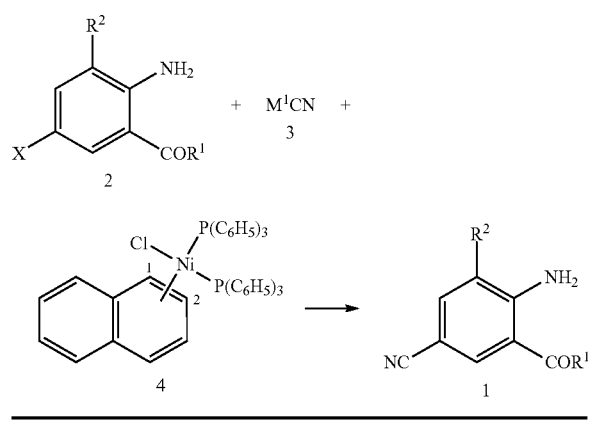

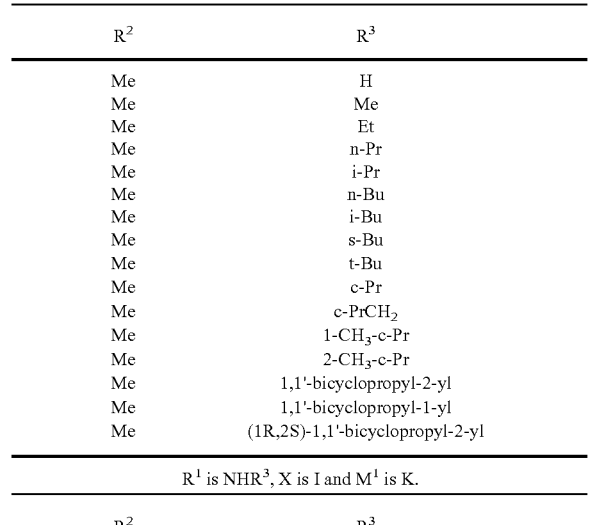

| R² | R³ |
|---|---|
| Me | i-Pr |
| Me | n-Bu |
| Me | i-Bu |
| Me | s-Bu |
| Me | t-Bu |
| Me | c-Pr |
| Me | c-PrCH₂ |
| Me | 1-CH₃-c-Pr |
| Me | 2-CH₃-c-Pr |
| Me | 1,1'-bicyclopropyl-2-yl |
| Me | 1,1'-bicyclopropyl-1-yl |
| Me | (1R,2S)-1,1'-bicyclopropyl-2-yl |

R¹ is NHR³, X is Cl and M¹ is K.

| R² | R³ |
|---|---|
| Me | H |
| Me | Me |
| Me | Et |
| Me | n-Pr |
| Me | i-Pr |
| Me | n-Bu |
| Me | i-Bu |
| Me | s-Bu |
| Me | t-Bu |
| Me | c-Pr |
| Me | c-PrCH₂ |
| Me | 1-CH₃-c-Pr |
| Me | 2-CH₃-c-Pr |
| Me | 1,1'-bicyclopropyl-2-yl |
| Me | 1,1'-bicyclopropyl-1-yl |
| Me | (1R,2S)-1,1'-bicyclopropyl-2-yl |

R¹ is NHR³, X is I and M¹ is K.

| R² | R³ |
|---|---|
| Me | H |
| Me | Me |
| Me | Et |
| Me | n-Pr |
| Me | i-Pr |
| Me | n-Bu |
| Me | i-Bu |
| Me | s-Bu |
| Me | t-Bu |
| Me | c-Pr |
| Me | c-PrCH₂ |
| Me | 1-CH₃-c-Pr |
| Me | 2-CH₃-c-Pr |
| Me | 1,1'-bicyclopropyl-2-yl |
| Me | 1,1'-bicyclopropyl-1-yl |
| Me | (1R,2S)-1,1'-bicyclopropyl-2-yl |

TABLE 1-continued

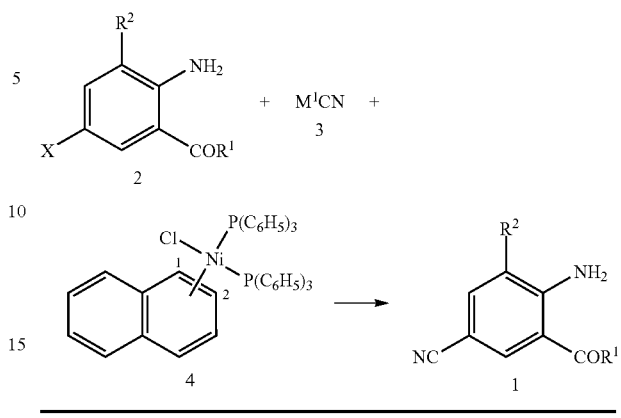

R¹ is NHR³, X is Br and M¹ Na.

| R² | R³ |
|---|---|
| Me | H |
| Me | Me |
| Me | Et |
| Me | n-Pr |
| Me | i-Pr |
| Me | n-Bu |
| Me | i-Bu |
| Me | s-Bu |
| Me | t-Bu |
| Me | c-Pr |
| Me | c-PrCH₂ |
| Me | 1-CH₃-c-Pr |
| Me | 2-CH₃-c-Pr |
| Me | 1,1'-bicyclopropyl-2-yl |
| Me | 1,1'-bicyclopropyl-1-yl |
| Me | (1R,2S)-1,1'-bicyclopropyl-2-yl |

R¹ is NHR³, X is Cl and M¹ is Na.

| R² | R³ |
|---|---|
| Me | H |
| Me | Me |
| Me | Et |
| Me | n-Pr |
| Me | i-Pr |
| Me | n-Bu |
| Me | i-Bu |
| Me | s-Bu |
| Me | t-Bu |
| Me | c-Pr |
| Me | c-PrCH₂ |
| Me | 1-CH₃-c-Pr |
| Me | 2-CH₃-c-Pr |
| Me | 1,1'-bicyclopropyl-2-yl |
| Me | 1,1'-bicyclopropyl-1-yl |
| Me | (1R,2S)-1,1'-bicyclopropyl-2-yl |

R¹ is NHR³, X is I and M¹ is Na.

| R² | R³ |
|---|---|
| Me | H |
| Me | Me |
| Me | Et |
| Me | n-Pr |
| Me | i-Pr |
| Me | n-Bu |
| Me | i-Bu |
| Me | s-Bu |
| Me | t-Bu |
| Me | c-Pr |
| Me | c-PrCH₂ |
| Me | 1-CH₃-c-Pr |
| Me | 2-CH₃-c-Pr |
| Me | 1,1'-bicyclopropyl-2-yl |

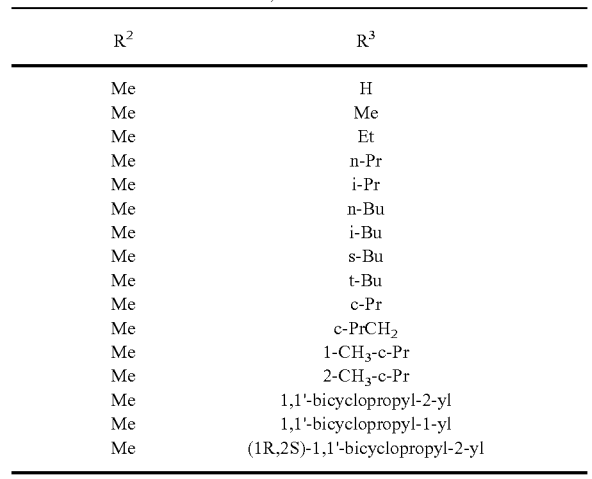

TABLE 1-continued

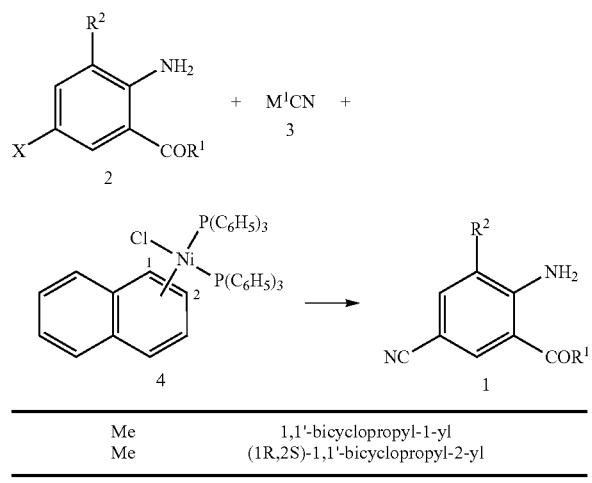
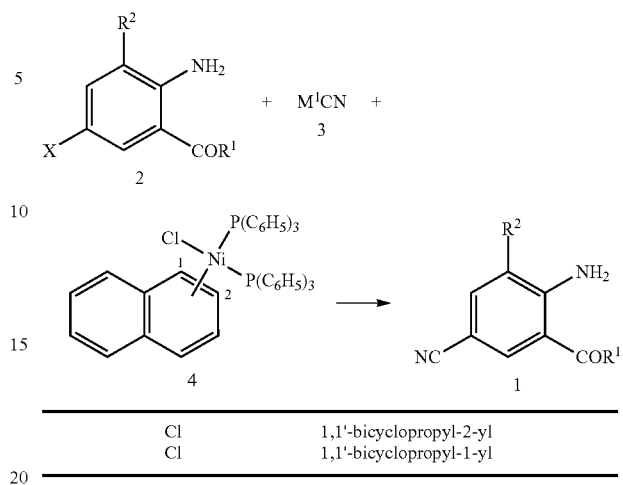

| $R^2$ | $R^3$ |
|---|---|
| Me | 1,1'-bicyclopropyl-1-yl |
| Me | (1R,2S)-1,1'-bicyclopropyl-2-yl |

$R^1$ is $NHR^3$, X is Br and $M^1$ is K.

| $R^2$ | $R^3$ |
|---|---|
| Cl | H |
| Cl | Me |
| Cl | Et |
| Cl | n-Pr |
| Cl | i-Pr |
| Cl | n-Bu |
| Cl | i-Bu |
| Cl | s-Bu |
| Cl | t-Bu |
| Cl | c-Pr |
| Cl | c-PrCH$_2$ |
| Cl | 1-CH$_3$-c-Pr |
| Cl | 2-CH$_3$-c-Pr |
| Cl | 1,1'-bicyclopropyl-2-yl |
| Cl | 1,1'-bicyclopropyl-1-yl |

$R^1$ is $NHR^3$, X is I and $M^1$ is K.

| $R^2$ | $R^3$ |
|---|---|
| Cl | H |
| Cl | Me |
| Cl | Et |
| Cl | n-Pr |
| Cl | i-Pr |
| Cl | n-Bu |
| Cl | i-Bu |
| Cl | s-Bu |
| Cl | t-Bu |
| Cl | c-Pr |
| Cl | c-PrCH$_2$ |
| Cl | 1-CH$_3$-c-Pr |
| Cl | 2-CH$_3$-c-Pr |
| Cl | 1,1'-bicyclopropyl-2-yl |
| Cl | 1,1'-bicyclopropyl-1-yl |

$R^1$ is $NHR^3$, X is Br and $M^1$ is Na.

| $R^2$ | $R^3$ |
|---|---|
| Cl | H |
| Cl | Me |
| Cl | Et |
| Cl | n-Pr |
| Cl | i-Pr |
| Cl | n-Bu |
| Cl | i-Bu |
| Cl | s-Bu |
| Cl | t-Bu |
| Cl | c-Pr |
| Cl | c-PrCH$_2$ |
| Cl | 1-CH$_3$-c-Pr |
| Cl | 2-CH$_3$-c-Pr |

| | |
|---|---|
| Cl | 1,1'-bicyclopropyl-2-yl |
| Cl | 1,1'-bicyclopropyl-1-yl |

$R^1$ is $NHR^3$, X is I and $M^1$ is Na.

| $R^2$ | $R^3$ |
|---|---|
| Cl | H |
| Cl | Me |
| Cl | Et |
| Cl | n-Pr |
| Cl | i-Pr |
| Cl | n-Bu |
| Cl | i-Bu |
| Cl | s-Bu |
| Cl | t-Bu |
| Cl | c-Pr |
| Cl | c-PrCH$_2$ |
| Cl | 1-CH$_3$-c-Pr |
| Cl | 2-CH$_3$-c-Pr |
| Cl | 1,1'-bicyclopropyl-2-yl |
| Cl | 1,1'-bicyclopropyl-1-yl |

$R^1$ is $OR^4$, X is Br and $M^1$ is K.

| $R^2$ | $R^4$ |
|---|---|
| Me | H |
| Me | Me |
| Me | Et |
| Me | n-Pr |
| Me | i-Pr |
| Me | n-Bu |
| Me | i-Bu |
| Me | s-Bu |
| Me | t-Bu |

$R^1$ is $OR^4$, X is Cl and $M^1$ is K.

| $R^2$ | $R^4$ |
|---|---|
| Me | H |
| Me | Me |
| Me | Et |
| Me | n-Pr |
| Me | i-Pr |
| Me | n-Bu |
| Me | i-Bu |
| Me | s-Bu |
| Me | t-Bu |

$R^1$ is $OR^4$, X is I and $M^1$ is K.

| $R^2$ | $R^4$ |
|---|---|
| Me | H |
| Me | Me |
| Me | Et |
| Me | n-Pr |
| Me | i-Pr |

TABLE 1-continued

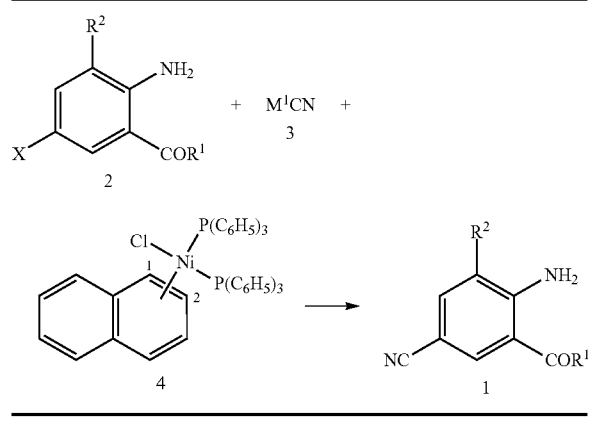

| R² | R⁴ |
|---|---|
| Me | n-Bu |
| Me | i-Bu |
| Me | s-Bu |
| Me | t-Bu |

| R¹ is OR⁴, X is Br and M¹ is Na. | |
|---|---|
| R² | R⁴ |
| Me | H |
| Me | Me |
| Me | Et |
| Me | n-Pr |
| Me | i-Pr |
| Me | n-Bu |
| Me | i-Bu |
| Me | s-Bu |
| Me | t-Bu |

| R¹ is OR⁴, X is Cl and M¹ is Na. | |
|---|---|
| R² | R⁴ |
| Me | H |
| Me | Me |
| Me | Et |
| Me | n-Pr |
| Me | i-Pr |
| Me | n-Bu |
| Me | i-Bu |
| Me | s-Bu |
| Me | t-Bu |

| R¹ is OR⁴, X is I and and M¹ is Na. | |
|---|---|
| R² | R⁴ |
| Me | H |
| Me | Me |
| Me | Et |
| Me | n-Pr |
| Me | i-Pr |
| Me | n-Bu |
| Me | i-Bu |
| Me | s-Bu |
| Me | t-Bu |

| R¹ is OR⁴, X is Br and M¹ is K. | |
|---|---|
| R² | R⁴ |
| Cl | H |
| Cl | Me |
| Cl | Et |
| Cl | n-Pr |
| Cl | i-Pr |
| Cl | n-Bu |
| Cl | i-Bu |

TABLE 1-continued

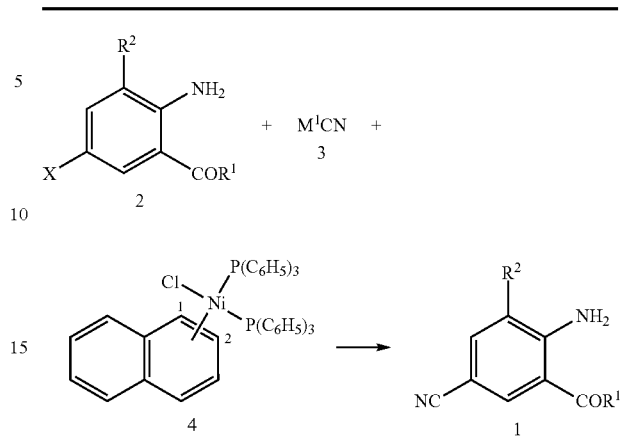

| | |
|---|---|
| Cl | s-Bu |
| Cl | t-Bu |

| R¹ is OR⁴, X is I and M¹ is K. | |
|---|---|
| R² | R⁴ |
| Cl | H |
| Cl | Me |
| Cl | Et |
| Cl | n-Pr |
| Cl | i-Pr |
| Cl | n-Bu |
| Cl | i-Bu |
| Cl | s-Bu |
| Cl | t-Bu |

| R¹ is OR⁴, X is Br and M¹ is Na. | |
|---|---|
| R² | R⁴ |
| Cl | H |
| Cl | Me |
| Cl | Et |
| Cl | n-Pr |
| Cl | i-Pr |
| Cl | n-Bu |
| Cl | i-Bu |
| Cl | s-Bu |
| Cl | t-Bu |

Table 2 illustrates particular transformations to prepare compounds of Formula 5 from compounds of Formula 2 according to a method of the present invention. Conversion of compounds of Formula 1 to compounds of Formula 5 can, for example, be accomplished according to the method of Scheme 7 using a sulfonyl chloride such as methanesulfonyl chloride in the presence of a solvent such as acetonitrile and a base such as 3-picoline. For these particular transformations $M^1$ is K.

TABLE 2

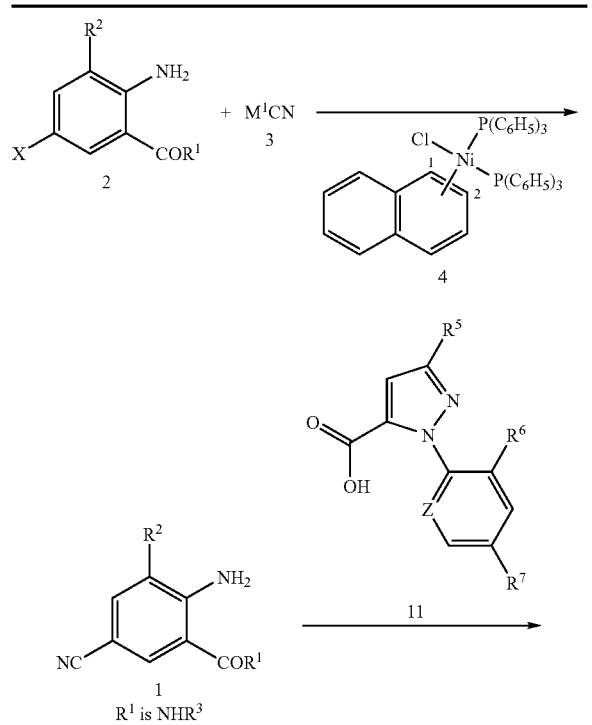

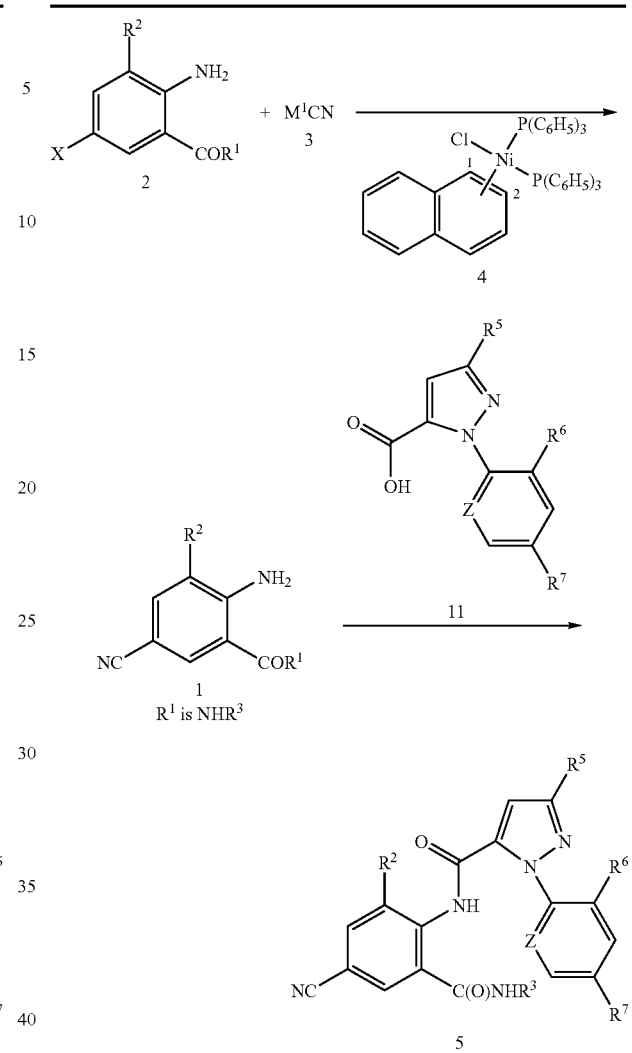

| R³ | R⁵ | R⁶ |
|---|---|---|
| R² is Me, X is Br, R⁷ is H and Z is N. | | |
| H | Br | F |
| Me | Br | F |
| Et | Br | F |
| n-Pr | Br | F |
| i-Pr | Br | F |
| n-Bu | Br | F |
| i-Bu | Br | F |
| s-Bu | Br | F |
| t-Bu | Br | F |
| c-Pr | Br | F |
| c-PrCH₂ | Br | F |
| 1-CH₃-c-Pr | Br | F |
| 2-CH₃-c-Pr | Br | F |
| 1-1'-bicyclopropyl-2-yl | Br | F |
| 1-1'-bicyclopropyl-1-yl | Br | F |
| H | Cl | F |
| Me | Cl | F |
| Et | Cl | F |
| n-Pr | Cl | F |
| i-Pr | Cl | F |
| n-Bu | Cl | F |
| i-Bu | Cl | F |
| s-Bu | Cl | F |
| t-Bu | Cl | F |
| c-Pr | Cl | F |
| c-PrCH₂ | Cl | F |
| 1-CH₃-c-Pr | Cl | F |
| 2-CH₃-c-Pr | Cl | F |
| 1-1'-bicyclopropyl-2-yl | Cl | F |
| 1-1'-bicyclopropyl-1-yl | Cl | F |
| H | OCH₂CF₃ | F |
| Me | OCH₂CF₃ | F |
| t-Bu | OCH₂CF₃ | F |
| 1-1'-bicyclopropyl-1-yl | OCH₂CF₃ | F |
| H | OCH₂CF₃ | Cl |
| Me | OCH₂CF₃ | Cl |
| t-Bu | OCH₂CF₃ | Cl |
| 1-1'-bicyclopropyl-1-yl | OCH₂CF₃ | Cl |
| H | OCH₂CF₃ | Br |
| Me | OCH₂CF₃ | Br |
| t-Bu | OCH₂CF₃ | Br |
| 1-1'-bicyclopropyl-1-yl | OCH₂CF₃ | Br |
| H | CF₃ | F |
| Me | CF₃ | F |
| t-Bu | CF₃ | F |
| H | Br | Cl |
| Me | Br | Cl |
| Et | Br | Cl |
| n-Pr | Br | Cl |
| i-Pr | Br | Cl |
| n-Bu | Br | Cl |
| i-Bu | Br | Cl |
| s-Bu | Br | Cl |
| t-Bu | Br | Cl |

TABLE 2-continued

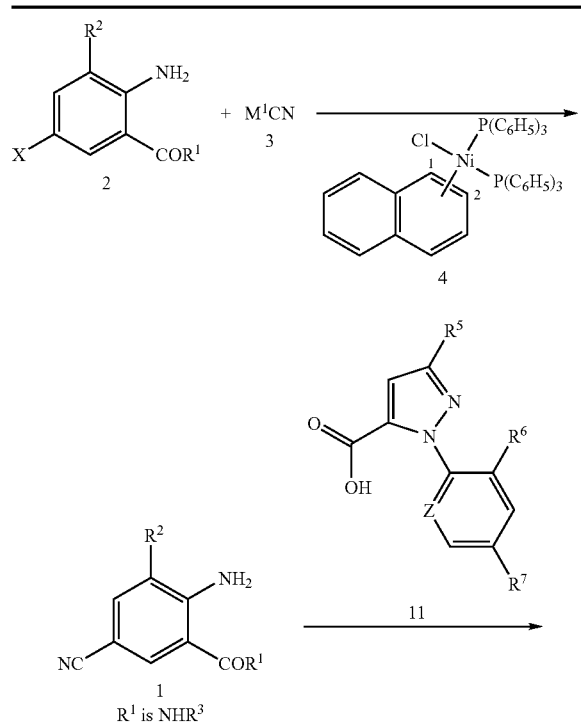

| R³ | R⁵ | R⁶ |
|---|---|---|
| c-Pr | Br | Cl |
| c-PrCH₂ | Br | Cl |
| 1-CH₃-c-Pr | Br | Cl |
| 2-CH₃-c-Pr | Br | Cl |
| 1-1'-bicyclopropyl-2-yl | Br | Cl |
| 1-1'-bicyclopropyl-1-yl | Br | Cl |
| H | Cl | Cl |
| Me | Cl | Cl |
| Et | Cl | Cl |
| n-Pr | Cl | Cl |
| i-Pr | Cl | Cl |
| n-Bu | Cl | Cl |
| i-Bu | Cl | Cl |
| s-Bu | Cl | Cl |
| t-Bu | Cl | Cl |
| c-Pr | Cl | Cl |
| c-PrCH₂ | Cl | Cl |
| 1-CH₃-c-Pr | Cl | Cl |
| 2-CH₃-c-Pr | Cl | Cl |
| 1-1'-bicyclopropyl-2-yl | Cl | Cl |
| 1-1'-bicyclopropyl-1-yl | Cl | Cl |
| H | OCF₂H | F |
| Me | OCF₂H | F |
| t-Bu | OCF₂H | F |
| 1-1'-bicyclopropyl-1-yl | OCF₂H | F |
| H | OCF₂H | Cl |
| Me | OCF₂H | Cl |
| t-Bu | OCF₂H | Cl |

TABLE 2-continued

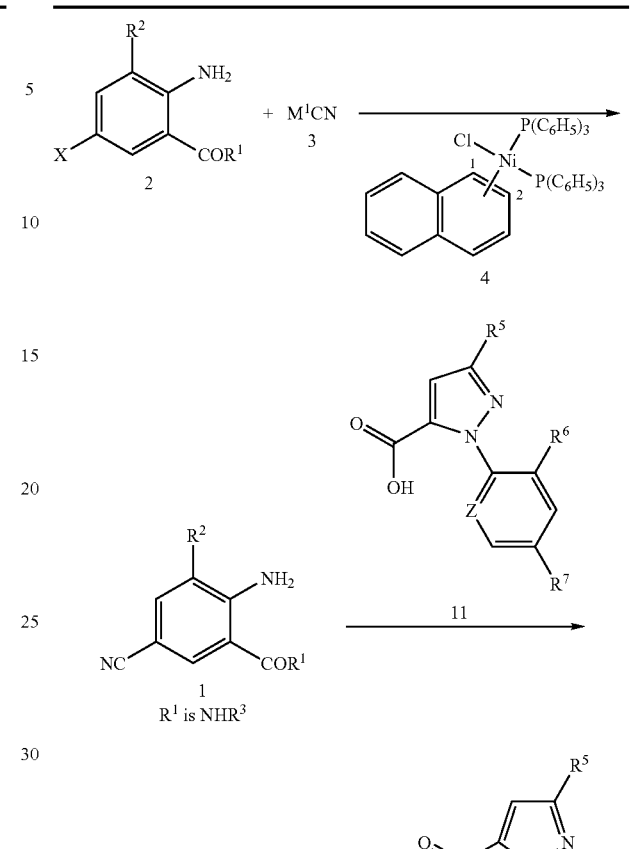

| R³ | R⁵ | R⁶ |
|---|---|---|
| 1-1'-bicyclopropyl-1-yl | OCF₂H | Cl |
| H | OCF₂H | Br |
| Me | OCF₂H | Br |
| t-Bu | OCF₂H | Br |
| 1-1'-bicyclopropyl-1-yl | OCF₂H | Br |
| 1-CH₃-c-Pr | CF₃ | F |
| 2-CH₃-c-Pr | CF₃ | F |
| 1,1'-bicyclopropyl-2-yl | CF₃ | F |
| H | Br | Br |
| Me | Br | Br |
| Et | Br | Br |
| n-Pr | Br | Br |
| i-Pr | Br | Br |
| n-Bu | Br | Br |
| i-Bu | Br | Br |
| s-Bu | Br | Br |
| t-Bu | Br | Br |
| c-Pr | Br | Br |
| c-PrCH₂ | Br | Br |
| 1-CH₃-c-Pr | Br | Br |
| 2-CH₃-c-Pr | Br | Br |
| 1-1'-bicyclopropyl-2-yl | Br | Br |
| 1-1'-bicyclopropyl-1-yl | Br | Br |
| H | Cl | Br |
| Me | Cl | Br |
| Et | Cl | Br |
| n-Pr | Cl | Br |
| i-Pr | Cl | Br |

TABLE 2-continued

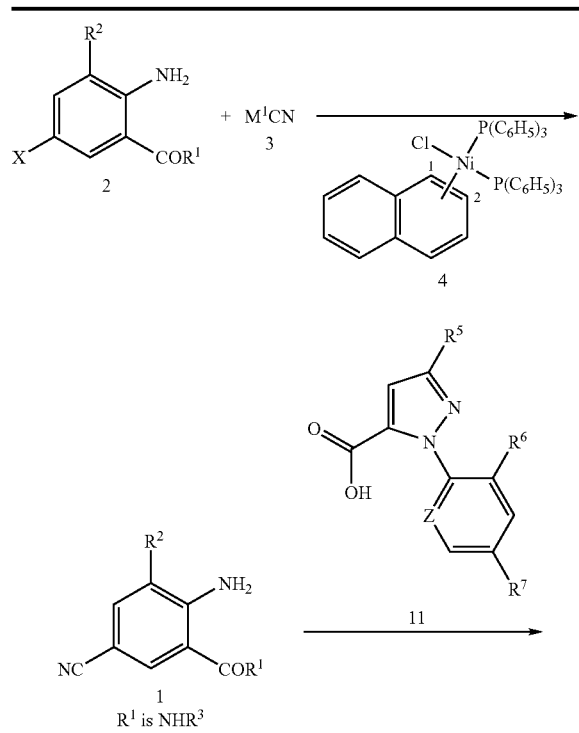

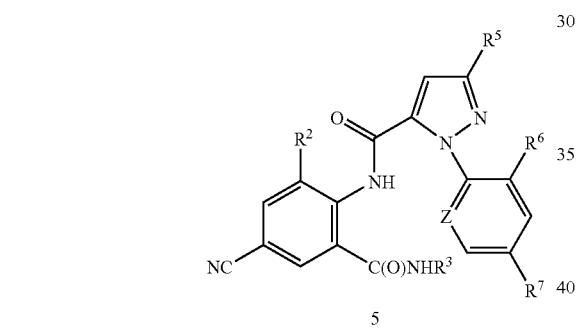

| R³ | R⁵ | R⁶ |
|---|---|---|
| n-Bu | Cl | Br |
| i-Bu | Cl | Br |
| s-Bu | Cl | Br |
| t-Bu | Cl | Br |
| c-Pr | Cl | Br |
| c-PrCH₂ | Cl | Br |
| 1-CH₃-c-Pr | Cl | Br |
| 2-CH₃-c-Pr | Cl | Br |
| 1-1'-bicyclopropyl-2-yl | Cl | Br |
| 1-1'-bicyclopropyl-1-yl | Cl | Br |
| H | CF₃ | Br |
| Me | CF₃ | Br |
| t-Bu | CF₃ | Br |
| 1-CH₃-c-Pr | CF₃ | Br |
| 2-CH₃-c-Pr | CF₃ | Br |
| 1-1'-bicyclopropyl-2-yl | CF₃ | Br |
| 1-1'-bicyclopropyl-1-yl | CF₃ | Br |
| H | CF₃ | Cl |
| Me | CF₃ | Cl |
| t-Bu | CF₃ | Cl |
| 1-CH₃-c-Pr | CF₃ | Cl |
| 2-CH₃-c-Pr | CF₃ | Cl |
| 1-1'-bicyclopropyl-2-yl | CF₃ | Cl |
| 1-1'-bicyclopropyl-1-yl | CF₃ | Cl |
| 1-1'-bicyclopropyl-1-yl | CF₃ | F |

TABLE 2-continued

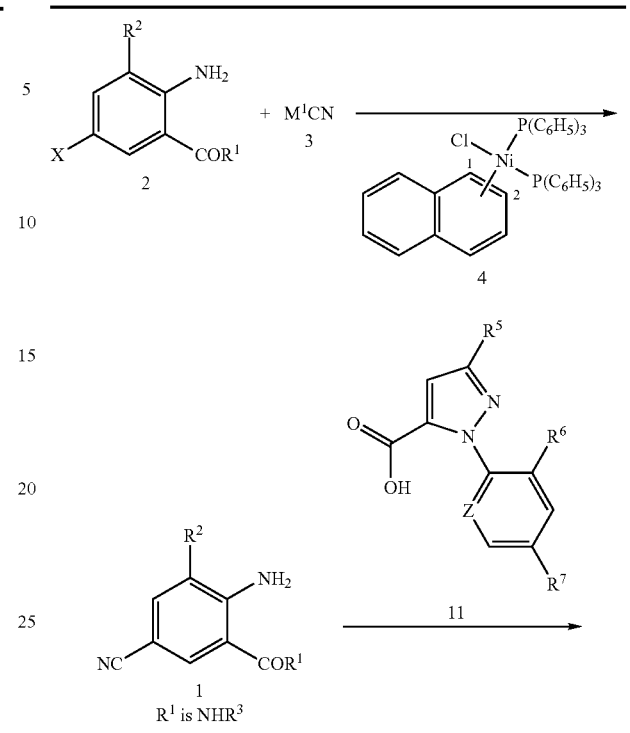

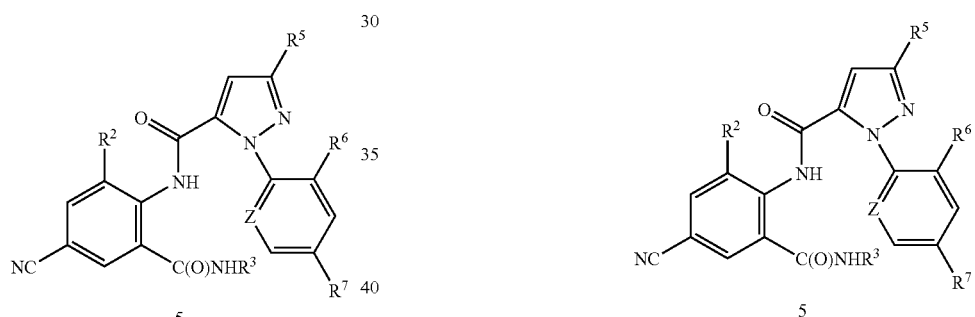

| R³ | R⁵ | R⁶ |
|---|---|---|
| R² is Me, X is Cl, R⁷ is H and Z is N. | | |
| H | Br | F |
| Me | Br | F |
| Et | Br | F |
| n-Pr | Br | F |
| i-Pr | Br | F |
| n-Bu | Br | F |
| i-Bu | Br | F |
| s-Bu | Br | F |
| t-Bu | Br | F |
| c-Pr | Br | F |
| c-PrCH₂ | Br | F |
| 1-CH₃-c-Pr | Br | F |
| 2-CH₃-c-Pr | Br | F |
| 1-1'-bicyclopropyl-2-yl | Br | F |
| 1-1'-bicyclopropyl-1-yl | Br | F |
| H | Cl | F |
| Me | Cl | F |
| Et | Cl | F |
| n-Pr | Cl | F |
| i-Pr | Cl | F |
| n-Bu | Cl | F |
| i-Bu | Cl | F |
| s-Bu | Cl | F |
| t-Bu | Cl | F |
| c-Pr | Cl | F |
| c-PrCH₂ | Cl | F |

TABLE 2-continued

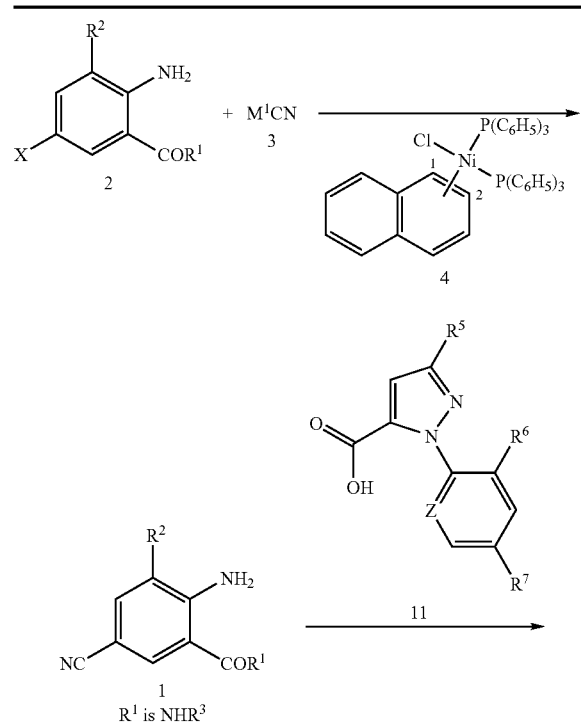

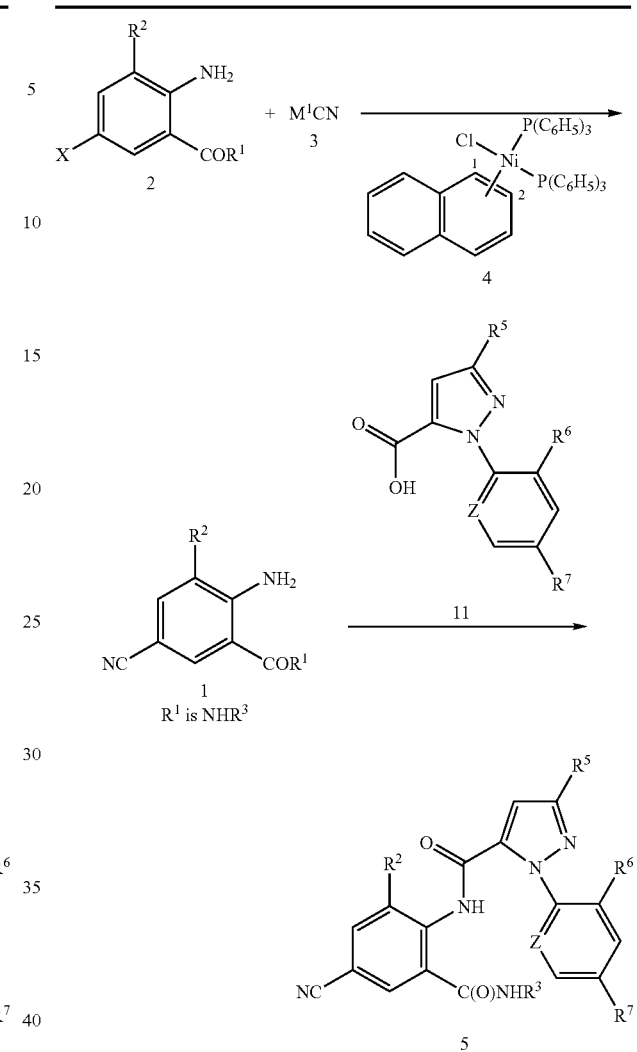

| R³ | R⁵ | R⁶ |
|---|---|---|
| 1-CH₃-c-Pr | Cl | F |
| 2-CH₃-c-Pr | Cl | F |
| 1-1'-bicyclopropyl-2-yl | Cl | F |
| 1-1'-bicyclopropyl-1-yl | Cl | F |
| H | OCH₂CF₃ | F |
| Me | OCH₂CF₃ | F |
| t-Bu | OCH₂CF₃ | F |
| 1-1'-bicyclopropyl-1-yl | OCH₂CF₃ | F |
| H | OCH₂CF₃ | Cl |
| Me | OCH₂CF₃ | Cl |
| t-Bu | OCH₂CF₃ | Cl |
| 1-1'-bicyclopropyl-1-yl | OCH₂CF₃ | Cl |
| H | OCH₂CF₃ | Br |
| Me | OCH₂CF₃ | Br |
| t-Bu | OCH₂CF₃ | Br |
| 1-1'-bicyclopropyl-1-yl | OCH₂CF₃ | Br |
| H | CF₃ | F |
| Me | CF₃ | F |
| t-Bu | CF₃ | F |
| H | Br | Cl |
| Me | Br | Cl |
| Et | Br | Cl |
| n-Pr | Br | Cl |
| i-Pr | Br | Cl |
| n-Bu | Br | Cl |
| i-Bu | Br | Cl |
| s-Bu | Br | Cl |
| t-Bu | Br | Cl |
| c-Pr | Br | Cl |
| c-PrCH₂ | Br | Cl |
| 1-CH₃-c-Pr | Br | Cl |
| 2-CH₃-c-Pr | Br | Cl |
| 1-1'-bicyclopropyl-2-yl | Br | Cl |
| 1-1'-bicyclopropyl-1-yl | Br | Cl |
| H | Cl | Cl |
| Me | Cl | Cl |
| Et | Cl | Cl |
| n-Pr | Cl | Cl |
| i-Pr | Cl | Cl |
| n-Bu | Cl | Cl |
| i-Bu | Cl | Cl |
| s-Bu | Cl | Cl |
| t-Bu | Cl | Cl |
| c-Pr | Cl | Cl |
| c-PrCH₂ | Cl | Cl |
| 1-CH₃-c-Pr | Cl | Cl |
| 2-CH₃-c-Pr | Cl | Cl |
| 1-1'-bicyclopropyl-2-yl | Cl | Cl |
| 1-1'-bicyclopropyl-1-yl | Cl | Cl |
| H | OCF₂H | F |
| Me | OCF₂H | F |
| t-Bu | OCF₂H | F |
| 1-1'-bicyclopropyl-2-yl | OCF₂H | F |
| H | OCF₂H | Cl |
| Me | OCF₂H | Cl |
| t-Bu | OCF₂H | Cl |

TABLE 2-continued

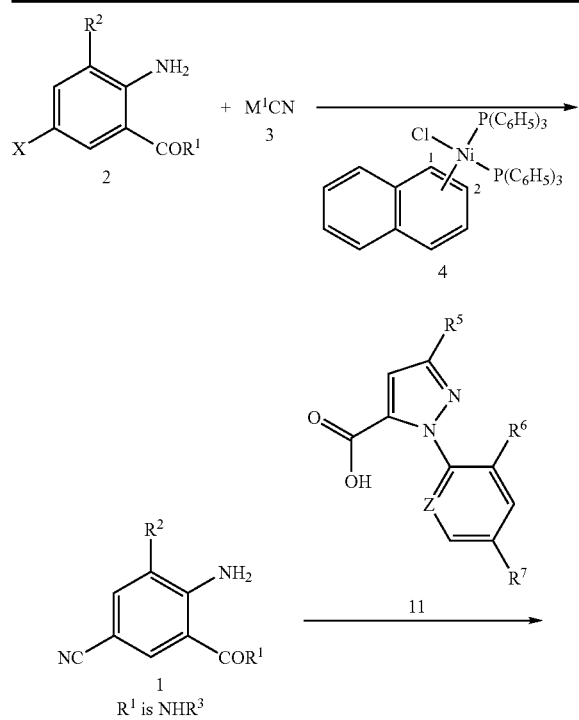
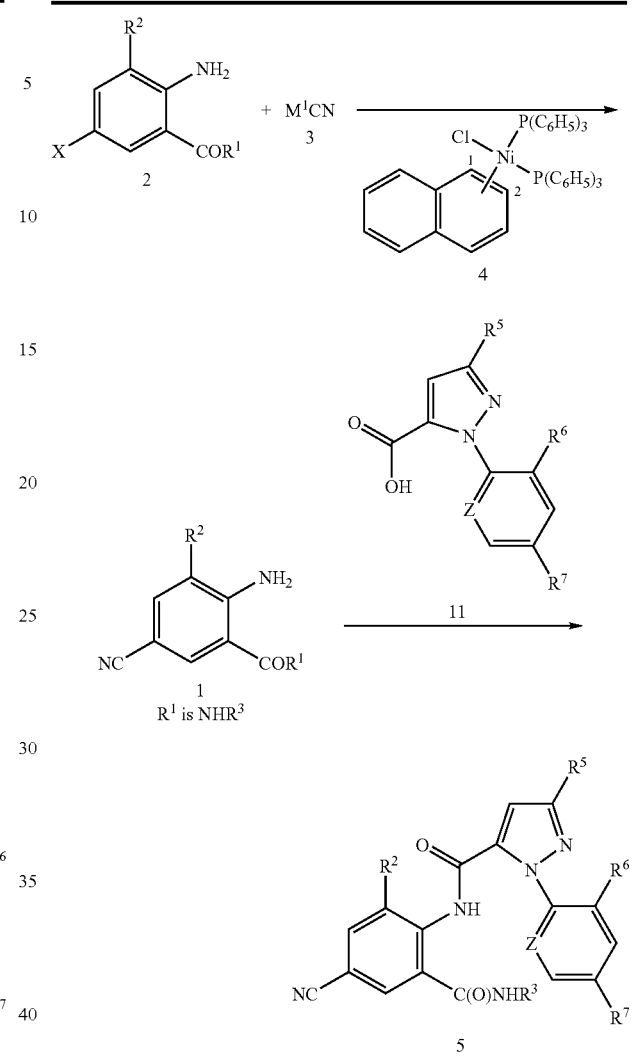

| R³ | R⁵ | R⁶ |
|---|---|---|
| 1-1'-bicyclopropyl-1-yl | OCF₂H | Cl |
| H | OCF₂H | Br |
| Me | OCF₂H | Br |
| t-Bu | OCF₂H | Br |
| 1-1'-bicyclopropyl-1-yl | OCF₂H | Br |
| 1-CH₃-c-Pr | CF₃ | F |
| 2-CH₃-c-Pr | CF₃ | F |
| 1,1'-bicyclopropyl-2-yl | CF₃ | F |
| H | Br | Br |
| Me | Br | Br |
| Et | Br | Br |
| n-Pr | Br | Br |
| i-Pr | Br | Br |
| n-Bu | Br | Br |
| i-Bu | Br | Br |
| s-Bu | Br | Br |
| t-Bu | Br | Br |
| c-Pr | Br | Br |
| c-PrCH₂ | Br | Br |
| 1-CH₃-c-Pr | Br | Br |
| 2-CH₃-c-Pr | Br | Br |
| 1-1'-bicyclopropyl-2-yl | Br | Br |
| 1-1'-bicyclopropyl-1-yl | Br | Br |
| H | Cl | Br |
| Me | Cl | Br |
| Et | Cl | Br |
| n-Pr | Cl | Br |
| i-Pr | Cl | Br |
| n-Bu | Cl | Br |
| i-Bu | Cl | Br |
| s-Bu | Cl | Br |
| t-Bu | Cl | Br |
| c-Pr | Cl | Br |
| c-PrCH₂ | Cl | Br |
| 1-CH₃-c-Pr | Cl | Br |
| 2-CH₃-c-Pr | Cl | Br |
| 1-1'-bicyclopropyl-2-yl | Cl | Br |
| 1-1'-bicyclopropyl-1-yl | Cl | Br |
| H | CF₃ | Br |
| Me | CF₃ | Br |
| t-Bu | CF₃ | Br |
| 1-CH₃-c-Pr | CF₃ | Br |
| 2-CH₃-c-Pr | CF₃ | Br |
| 1-1'-bicyclopropyl-2-yl | CF₃ | Br |
| 1-1'-bicyclopropyl-1-yl | CF₃ | Br |
| H | CF₃ | Cl |
| Me | CF₃ | Cl |
| t-Bu | CF₃ | Cl |
| 1-CH₃-c-Pr | CF₃ | Cl |
| 2-CH₃-c-Pr | CF₃ | Cl |
| 1-1'-bicyclopropyl-2-yl | CF₃ | Cl |
| 1-1'-bicyclopropyl-1-yl | CF₃ | Cl |
| 1-1'-bicyclopropyl-1-yl | CF₃ | F |

TABLE 2-continued

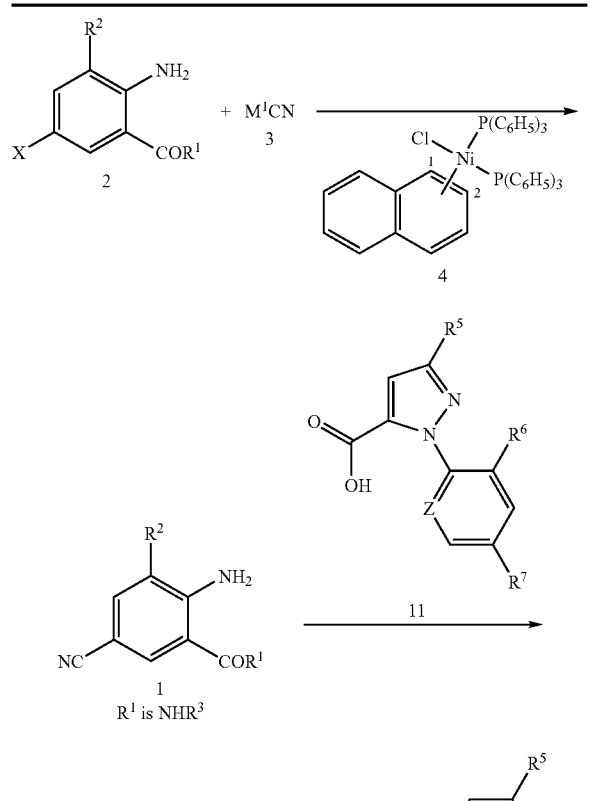
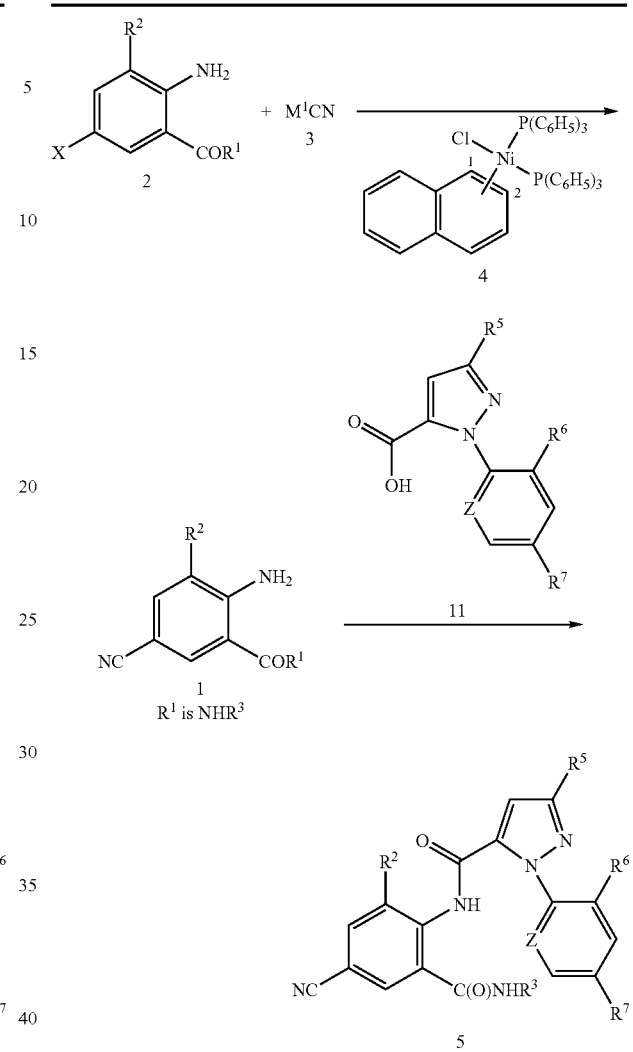

| R³ | R⁵ | R⁶ |
|---|---|---|
| R² is Me, X is I, R⁷ is H and Z is N. | | |
| H | Br | F |
| Me | Br | F |
| Et | Br | F |
| n-Pr | Br | F |
| i-Pr | Br | F |
| n-Bu | Br | F |
| i-Bu | Br | F |
| s-Bu | Br | F |
| t-Bu | Br | F |
| c-Pr | Br | F |
| c-PrCH₂ | Br | F |
| 1-CH₃-c-Pr | Br | F |
| 2-CH₃-c-Pr | Br | F |
| 1-1'-bicyclopropyl-2-yl | Br | F |
| 1-1'-bicyclopropyl-1-yl | Br | F |
| H | Cl | F |
| Me | Cl | F |
| Et | Cl | F |
| n-Pr | Cl | F |
| i-Pr | Cl | F |
| n-Bu | Cl | F |
| i-Bu | Cl | F |
| s-Bu | Cl | F |
| t-Bu | Cl | F |
| c-Pr | Cl | F |
| c-PrCH₂ | Cl | F |
| 1-CH₃-c-Pr | Cl | F |
| 2-CH₃-c-Pr | Cl | F |
| 1-1'-bicyclopropyl-2-yl | Cl | F |
| 1-1'-bicyclopropyl-1-yl | Cl | F |
| H | OCH₂CF₃ | F |
| Me | OCH₂CF₃ | F |
| t-Bu | OCH₂CF₃ | F |
| 1-1'-bicyclopropyl-1-yl | OCH₂CF₃ | F |
| H | OCH₂CF₃ | Cl |
| Me | OCH₂CF₃ | Cl |
| t-Bu | OCH₂CF₃ | Cl |
| 1-1'-bicyclopropyl-1-yl | OCH₂CF₃ | Cl |
| H | OCH₂CF₃ | Br |
| Me | OCH₂CF₃ | Br |
| t-Bu | OCH₂CF₃ | Br |
| 1-1'-bicyclopropyl-1-yl | OCH₂CF₃ | Br |
| H | CF₃ | F |
| Me | CF₃ | F |
| t-Bu | CF₃ | F |
| H | Br | Cl |
| Me | Br | Cl |
| Et | Br | Cl |
| n-Pr | Br | Cl |
| i-Pr | Br | Cl |
| n-Bu | Br | Cl |
| i-Bu | Br | Cl |
| s-Bu | Br | Cl |
| t-Bu | Br | Cl |

TABLE 2-continued

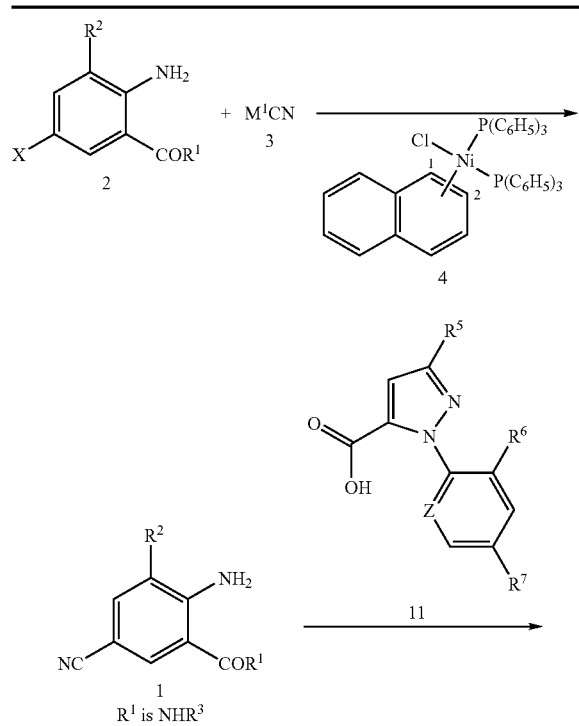

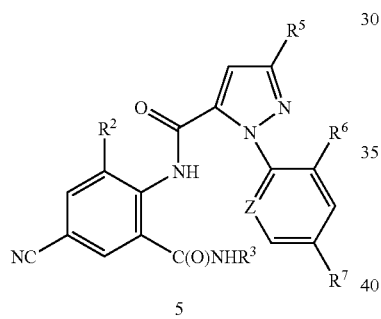

| R³ | R⁵ | R⁶ |
|---|---|---|
| c-Pr | Br | Cl |
| c-PrCH₂ | Br | Cl |
| 1-CH₃-c-Pr | Br | Cl |
| 2-CH₃-c-Pr | Br | Cl |
| 1-1'-bicyclopropyl-2-yl | Br | Cl |
| 1-1'-bicyclopropyl-1-yl | Br | Cl |
| H | Cl | Cl |
| Me | Cl | Cl |
| Et | Cl | Cl |
| n-Pr | Cl | Cl |
| i-Pr | Cl | Cl |
| n-Bu | Cl | Cl |
| i-Bu | Cl | Cl |
| s-Bu | Cl | Cl |
| t-Bu | Cl | Cl |
| c-Pr | Cl | Cl |
| c-PrCH₂ | Cl | Cl |
| 1-CH₃-c-Pr | Cl | Cl |
| 2-CH₃-c-Pr | Cl | Cl |
| 1-1'-bicyclopropyl-2-yl | Cl | Cl |
| 1-1'-bicyclopropyl-1-yl | Cl | Cl |
| H | OCF₂H | F |
| Me | OCF₂H | F |
| t-Bu | OCF₂H | F |
| 1-1'-bicyclopropyl-2-yl | OCF₂H | F |
| H | OCF₂H | Cl |
| Me | OCF₂H | Cl |
| t-Bu | OCF₂H | Cl |

TABLE 2-continued

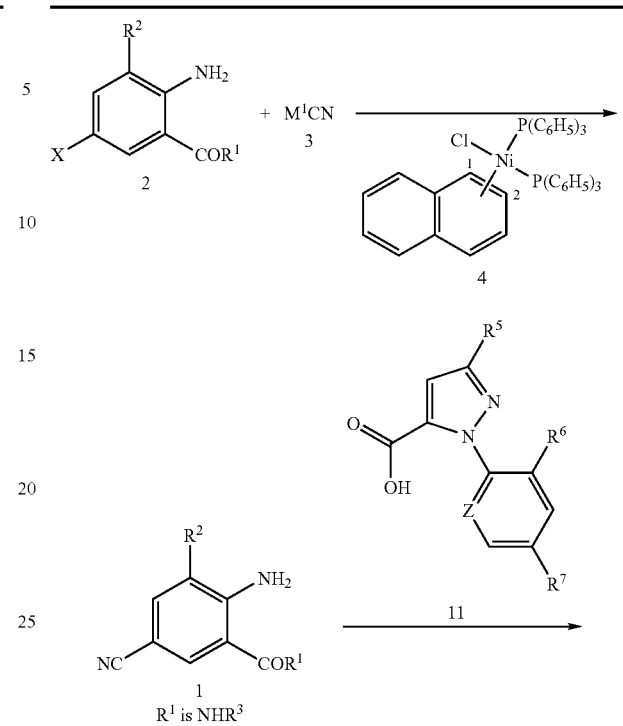

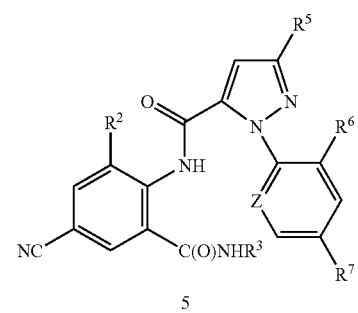

| R³ | R⁵ | R⁶ |
|---|---|---|
| 1-1'-bicyclopropyl-1-yl | OCF₂H | Cl |
| H | OCF₂H | Br |
| Me | OCF₂H | Br |
| t-Bu | OCF₂H | Br |
| 1-1'-bicyclopropyl-1-yl | OCF₂H | Br |
| 1-CH₃-c-Pr | CF₃ | F |
| 2-CH₃-c-Pr | CF₃ | F |
| 1,1'-bicyclopropyl-2-yl | CF₃ | F |
| H | Br | Br |
| Me | Br | Br |
| Et | Br | Br |
| n-Pr | Br | Br |
| i-Pr | Br | Br |
| n-Bu | Br | Br |
| i-Bu | Br | Br |
| s-Bu | Br | Br |
| t-Bu | Br | Br |
| c-Pr | Br | Br |
| c-PrCH₂ | Br | Br |
| 1-CH₃-c-Pr | Br | Br |
| 2-CH₃-c-Pr | Br | Br |
| 1-1'-bicyclopropyl-2-yl | Br | Br |
| 1-1'-bicyclopropyl-1-yl | Br | Br |
| H | Cl | Br |
| Me | Cl | Br |
| Et | Cl | Br |
| n-Pr | Cl | Br |
| i-Pr | Cl | Br |

TABLE 2-continued

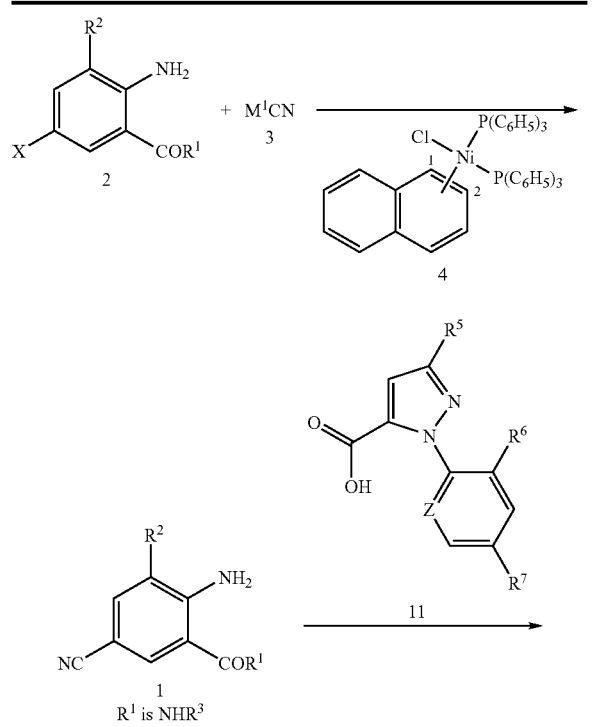

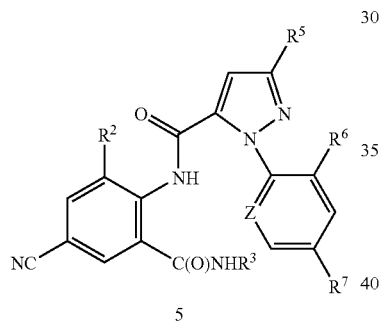

| R³ | R⁵ | R⁶ |
|---|---|---|
| n-Bu | Cl | Br |
| i-Bu | Cl | Br |
| s-Bu | Cl | Br |
| t-Bu | Cl | Br |
| c-Pr | Cl | Br |
| c-PrCH₂ | Cl | Br |
| 1-CH₃-c-Pr | Cl | Br |
| 2-CH₃-c-Pr | Cl | Br |
| 1-1'-bicyclopropyl-2-yl | Cl | Br |
| 1-1'-bicyclopropyl-1-yl | Cl | Br |
| H | CF₃ | Br |
| Me | CF₃ | Br |
| t-Bu | CF₃ | Br |
| 1-CH₃-c-Pr | CF₃ | Br |
| 2-CH₃-c-Pr | CF₃ | Br |
| 1-1'-bicyclopropyl-2-yl | CF₃ | Br |
| 1-1'-bicyclopropyl-1-yl | CF₃ | Br |
| H | CF₃ | Cl |
| Me | CF₃ | Cl |
| t-Bu | CF₃ | Cl |
| 1-CH₃-c-Pr | CF₃ | Cl |
| 2-CH₃-c-Pr | CF₃ | Cl |
| 1-1'-bicyclopropyl-2-yl | CF₃ | Cl |
| 1-1'-bicyclopropyl-1-yl | CF₃ | Cl |
| 1-1'-bicyclopropyl-1-yl | CF₃ | F |

TABLE 2-continued

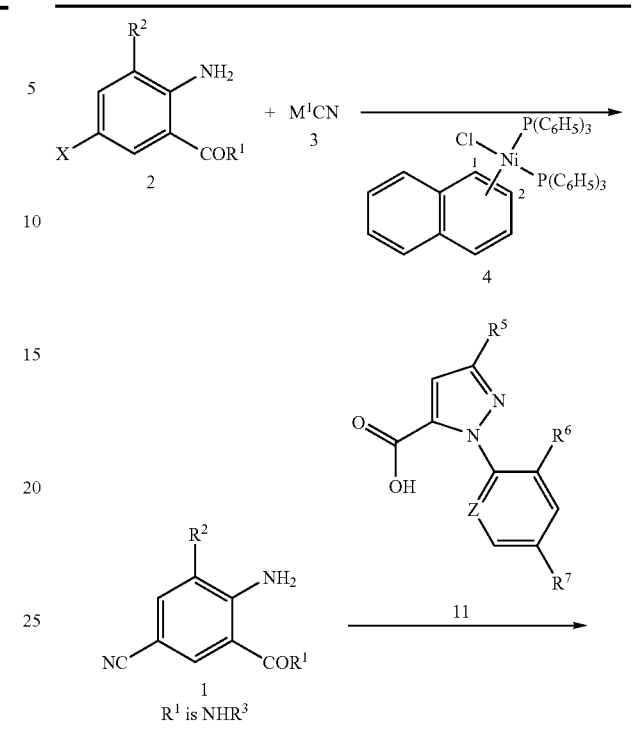

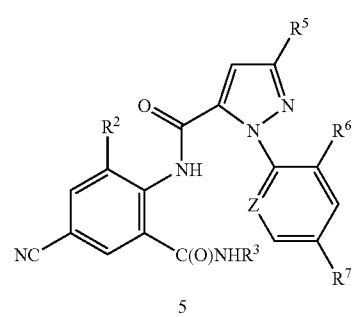

| R³ | R⁵ | R⁶ |
|---|---|---|
| R² is Cl, X is Br, R⁷ is H and Z is N. | | |
| H | Br | F |
| Me | Br | F |
| Et | Br | F |
| n-Pr | Br | F |
| i-Pr | Br | F |
| n-Bu | Br | F |
| i-Bu | Br | F |
| s-Bu | Br | F |
| t-Bu | Br | F |
| c-Pr | Br | F |
| c-PrCH₂ | Br | F |
| 1-CH₃-c-Pr | Br | F |
| 2-CH₃-c-Pr | Br | F |
| 1-1'-bicyclopropyl-2-yl | Br | F |
| 1-1'-bicyclopropyl-1-yl | Br | F |
| H | Cl | F |
| Me | Cl | F |
| Et | Cl | F |
| n-Pr | Cl | F |
| i-Pr | Cl | F |
| n-Bu | Cl | F |
| i-Bu | Cl | F |
| s-Bu | Cl | F |
| t-Bu | Cl | F |
| c-Pr | Cl | F |
| c-PrCH₂ | Cl | F |

TABLE 2-continued

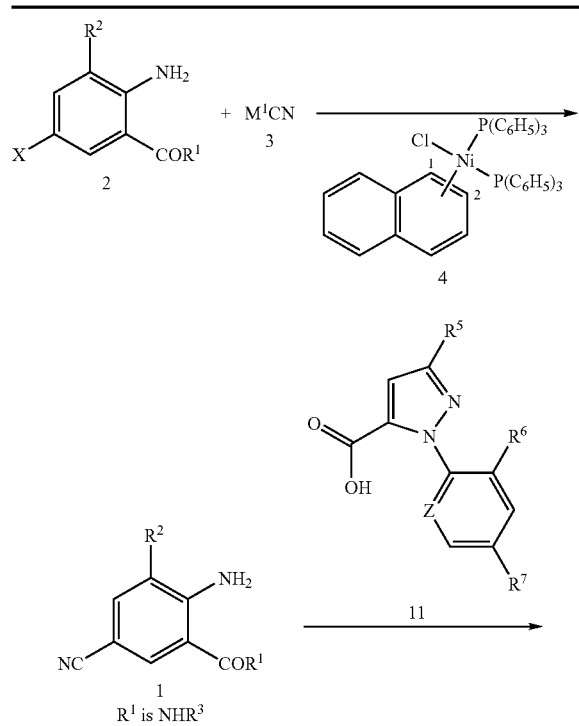

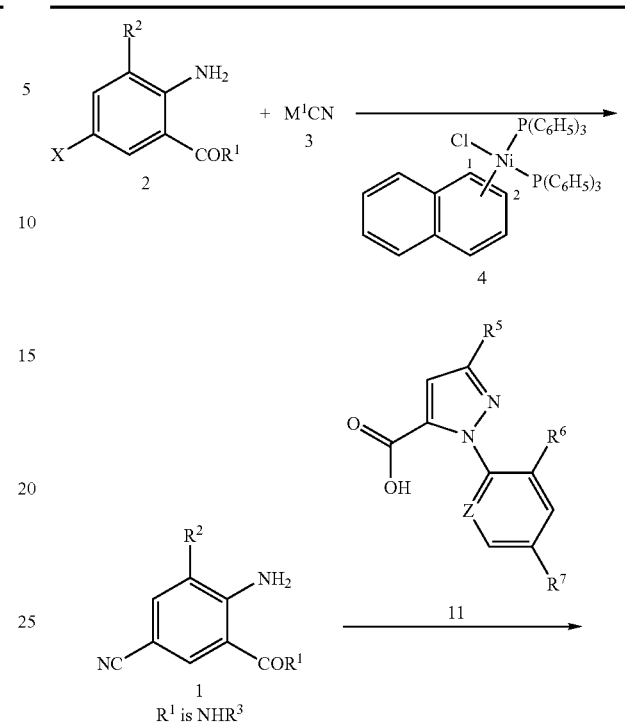

| R³ | R⁵ | R⁶ |
|---|---|---|
| 1-CH₃-c-Pr | Cl | F |
| 2-CH₃-c-Pr | Cl | F |
| 1-1'-bicyclopropyl-2-yl | Cl | F |
| 1-1'-bicyclopropyl-1-yl | Cl | F |
| H | OCH₂CF₃ | F |
| Me | OCH₂CF₃ | F |
| t-Bu | OCH₂CF₃ | F |
| 1-1'-bicyclopropyl-1-yl | OCH₂CF₃ | F |
| H | OCH₂CF₃ | Cl |
| Me | OCH₂CF₃ | Cl |
| t-Bu | OCH₂CF₃ | Cl |
| 1-1'-bicyclopropyl-1-yl | OCH₂CF₃ | Cl |
| H | OCH₂CF₃ | Br |
| Me | OCH₂CF₃ | Br |
| t-Bu | OCH₂CF₃ | Br |
| 1-1'-bicyclopropyl-1-yl | OCH₂CF₃ | Br |
| H | CF₃ | F |
| Me | CF₃ | F |
| t-Bu | CF₃ | F |
| H | Br | Cl |
| Me | Br | Cl |
| Et | Br | Cl |
| n-Pr | Br | Cl |
| i-Pr | Br | Cl |
| n-Bu | Br | Cl |
| i-Bu | Br | Cl |
| s-Bu | Br | Cl |
| t-Bu | Br | Cl |
| c-Pr | Br | Cl |
| c-PrCH₂ | Br | Cl |
| 1-CH₃-c-Pr | Br | Cl |
| 2-CH₃-c-Pr | Br | Cl |
| 1-1'-bicyclopropyl-2-yl | Br | Cl |
| 1-1'-bicyclopropyl-1-yl | Br | Cl |
| H | Cl | Cl |
| Me | Cl | Cl |
| Et | Cl | Cl |
| n-Pr | Cl | Cl |
| i-Pr | Cl | Cl |
| n-Bu | Cl | Cl |
| i-Bu | Cl | Cl |
| s-Bu | Cl | Cl |
| t-Bu | Cl | Cl |
| c-Pr | Cl | Cl |
| c-PrCH₂ | Cl | Cl |
| 1-CH₃-c-Pr | Cl | Cl |
| 2-CH₃-c-Pr | Cl | Cl |
| 1-1'-bicyclopropyl-2-yl | Cl | Cl |
| 1-1'-bicyclopropyl-1-yl | Cl | Cl |
| H | OCF₂H | F |
| Me | OCF₂H | F |
| t-Bu | OCF₂H | F |
| 1-1'-bicyclopropyl-1-yl | OCF₂H | F |
| H | OCF₂H | Cl |
| Me | OCF₂H | Cl |
| t-Bu | OCF₂H | Cl |

TABLE 2-continued

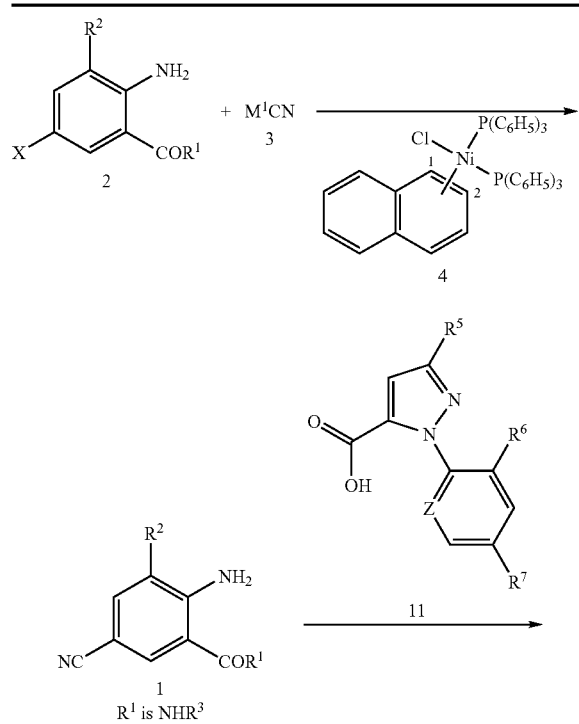
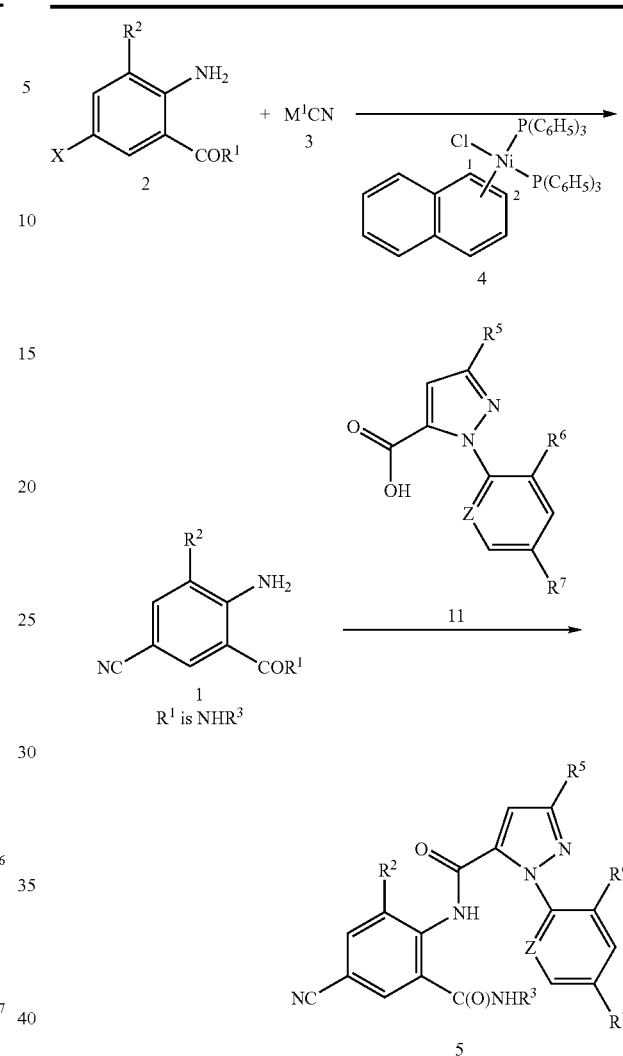

| R³ | R⁵ | R⁶ |
|---|---|---|
| 1-1'-bicyclopropyl-1-yl | OCF₂H | Cl |
| H | OCF₂H | Br |
| Me | OCF₂H | Br |
| t-Bu | OCF₂H | Br |
| 1-1'-bicyclopropyl-1-yl | OCF₂H | Br |
| 1-CH₃-c-Pr | CF₃ | F |
| 2-CH₃-c-Pr | CF₃ | F |
| 1,1'-bicyclopropyl-2-yl | CF₃ | F |
| H | Br | Br |
| Me | Br | Br |
| Et | Br | Br |
| n-Pr | Br | Br |
| i-Pr | Br | Br |
| n-Bu | Br | Br |
| i-Bu | Br | Br |
| s-Bu | Br | Br |
| t-Bu | Br | Br |
| c-Pr | Br | Br |
| c-PrCH₂ | Br | Br |
| 1-CH₃-c-Pr | Br | Br |
| 2-CH₃-c-Pr | Br | Br |
| 1-1'-bicyclopropyl-2-yl | Br | Br |
| 1-1'-bicyclopropyl-1-yl | Br | Br |
| H | Cl | Br |
| Me | Cl | Br |
| Et | Cl | Br |
| n-Pr | Cl | Br |
| i-Pr | Cl | Br |
| n-Bu | Cl | Br |
| i-Bu | Cl | Br |
| s-Bu | Cl | Br |
| t-Bu | Cl | Br |
| c-Pr | Cl | Br |
| c-PrCH₂ | Cl | Br |
| 1-CH₃-c-Pr | Cl | Br |
| 2-CH₃-c-Pr | Cl | Br |
| 1-1'-bicyclopropyl-2-yl | Cl | Br |
| 1-1'-bicyclopropyl-1-yl | Cl | Br |
| H | CF₃ | Br |
| Me | CF₃ | Br |
| t-Bu | CF₃ | Br |
| 1-CH₃-c-Pr | CF₃ | Br |
| 2-CH₃-c-Pr | CF₃ | Br |
| 1-1'-bicyclopropyl-2-yl | CF₃ | Br |
| 1-1'-bicyclopropyl-1-yl | CF₃ | Br |
| H | CF₃ | Cl |
| Me | CF₃ | Cl |
| t-Bu | CF₃ | Cl |
| 1-CH₃-c-Pr | CF₃ | Cl |
| 2-CH₃-c-Pr | CF₃ | Cl |
| 1-1'-bicyclopropyl-2-yl | CF₃ | Cl |
| 1-1'-bicyclopropyl-1-yl | CF₃ | Cl |
| 1-1'-bicyclopropyl-1-yl | CF₃ | F |

TABLE 2-continued

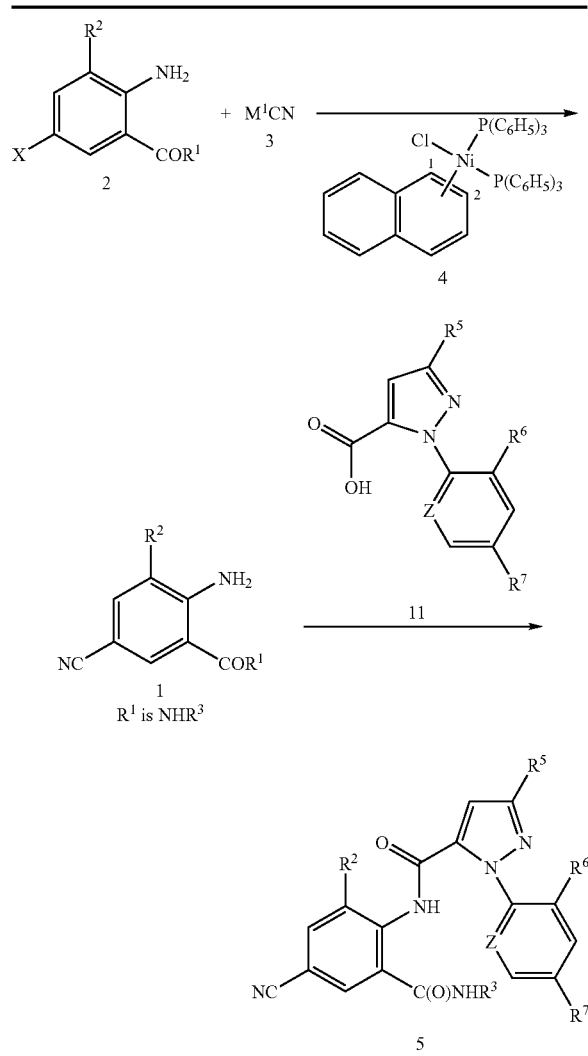

| R³ | R⁵ | R⁶ |
|---|---|---|
| R² is Cl, X is I, R⁷ is H and Z is N. | | |
| H | Br | F |
| Me | Br | F |
| Et | Br | F |
| n-Pr | Br | F |
| i-Pr | Br | F |
| n-Bu | Br | F |
| i-Bu | Br | F |
| s-Bu | Br | F |
| t-Bu | Br | F |
| c-Pr | Br | F |
| c-PrCH₂ | Br | F |
| 1-CH₃-c-Pr | Br | F |
| 2-CH₃-c-Pr | Br | F |
| 1-1'-bicyclopropyl-2-yl | Br | F |
| 1-1'-bicyclopropyl-1-yl | Br | F |
| H | Cl | F |
| Me | Cl | F |
| Et | Cl | F |
| n-Pr | Cl | F |
| i-Pr | Cl | F |
| n-Bu | Cl | F |
| i-Bu | Cl | F |
| s-Bu | Cl | F |
| t-Bu | Cl | F |
| c-Pr | Cl | F |
| c-PrCH₂ | Cl | F |

TABLE 2-continued

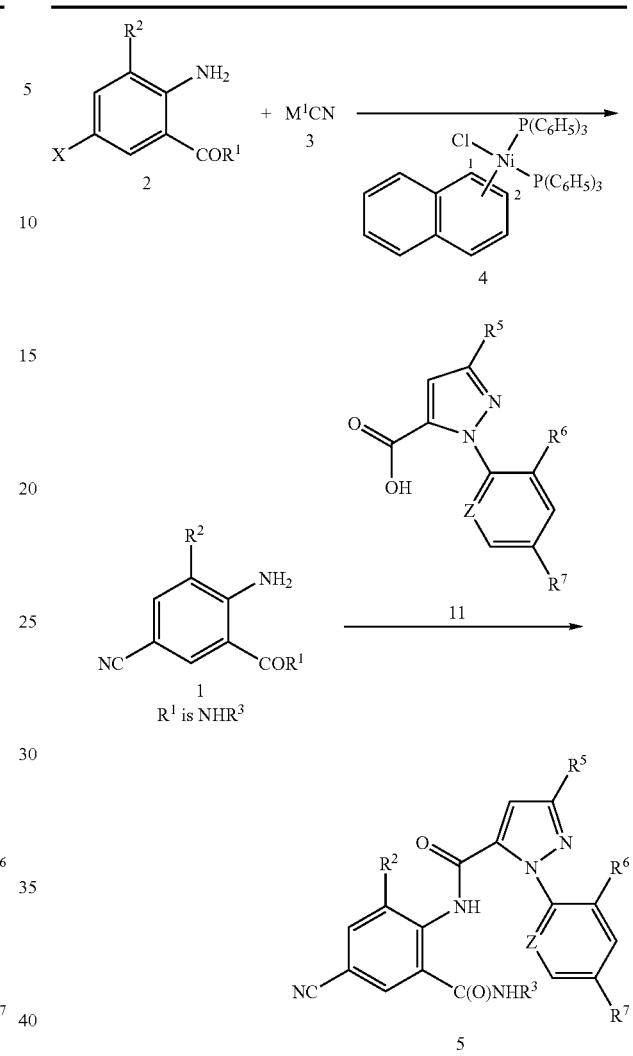

| R³ | R⁵ | R⁶ |
|---|---|---|
| 1-CH₃-c-Pr | Cl | F |
| 2-CH₃-c-Pr | Cl | F |
| 1-1'-bicyclopropyl-2-yl | Cl | F |
| 1-1'-bicyclopropyl-1-yl | Cl | F |
| H | OCH₂CF₃ | F |
| Me | OCH₂CF₃ | F |
| t-Bu | OCH₂CF₃ | F |
| 1-1'-bicyclopropyl-1-yl | OCH₂CF₃ | F |
| H | OCH₂CF₃ | Cl |
| Me | OCH₂CF₃ | Cl |
| t-Bu | OCH₂CF₃ | Cl |
| 1-1'-bicyclopropyl-1-yl | OCH₂CF₃ | Cl |
| H | OCH₂CF₃ | Br |
| Me | OCH₂CF₃ | Br |
| t-Bu | OCH₂CF₃ | Br |
| 1-1'-bicyclopropyl-1-yl | OCH₂CF₃ | Br |
| H | CF₃ | F |
| Me | CF₃ | F |
| t-Bu | CF₃ | F |
| H | Br | Cl |
| Me | Br | Cl |
| Et | Br | Cl |
| n-Pr | Br | Cl |
| i-Pr | Br | Cl |
| n-Bu | Br | Cl |
| i-Bu | Br | Cl |
| s-Bu | Br | Cl |
| t-Bu | Br | Cl |

TABLE 2-continued

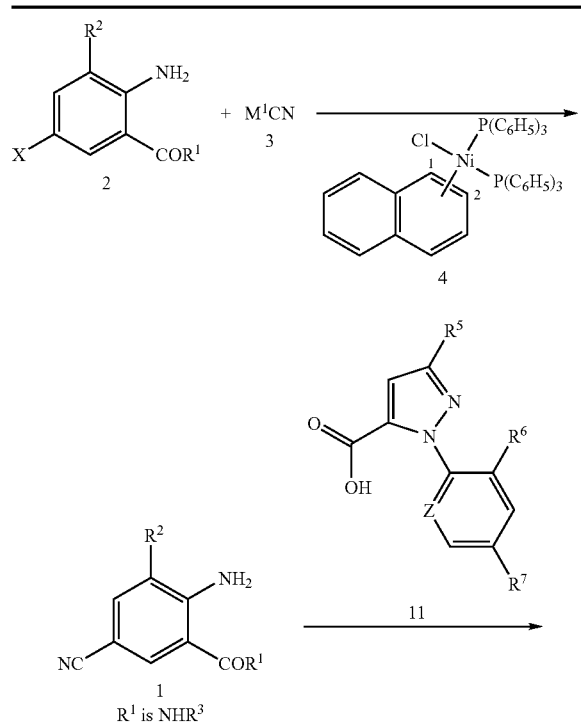

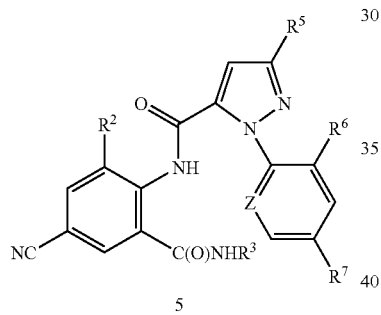

| R³ | R⁵ | R⁶ |
|---|---|---|
| c-Pr | Br | Cl |
| c-PrCH₂ | Br | Cl |
| 1-CH₃-c-Pr | Br | Cl |
| 2-CH₃-c-Pr | Br | Cl |
| 1-1'-bicyclopropyl-2-yl | Br | Cl |
| 1-1'-bicyclopropyl-1-yl | Br | Cl |
| H | Cl | Cl |
| Me | Cl | Cl |
| Et | Cl | Cl |
| n-Pr | Cl | Cl |
| i-Pr | Cl | Cl |
| n-Bu | Cl | Cl |
| i-Bu | Cl | Cl |
| s-Bu | Cl | Cl |
| t-Bu | Cl | Cl |
| c-Pr | Cl | Cl |
| c-PrCH₂ | Cl | Cl |
| 1-CH₃-c-Pr | Cl | Cl |
| 2-CH₃-c-Pr | Cl | Cl |
| 1-1'-bicyclopropyl-2-yl | Cl | Cl |
| 1-1'-bicyclopropyl-1-yl | Cl | Cl |
| H | OCF₂H | F |
| Me | OCF₂H | F |
| t-Bu | OCF₂H | F |
| 1-1'-bicyclopropyl-2-yl | OCF₂H | F |
| H | OCF₂H | Cl |
| Me | OCF₂H | Cl |
| t-Bu | OCF₂H | Cl |

TABLE 2-continued

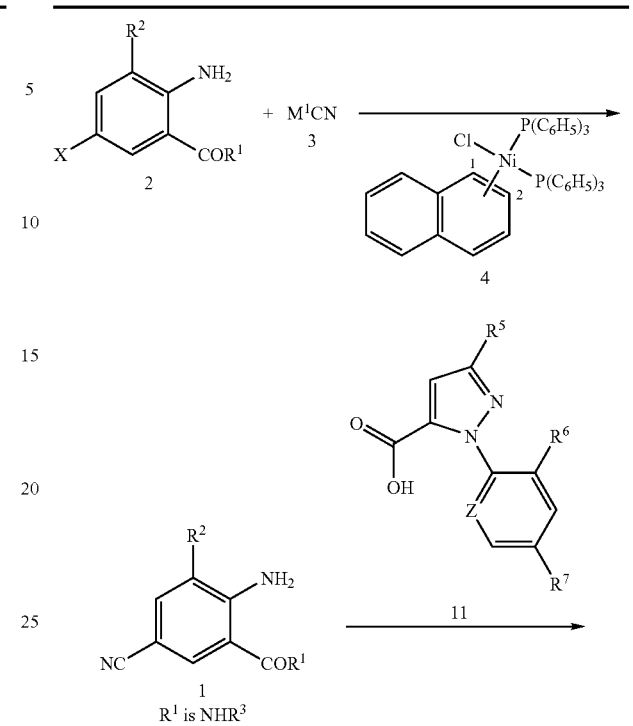

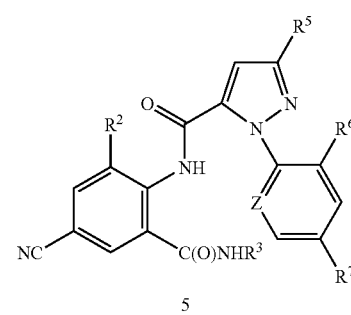

| R³ | R⁵ | R⁶ |
|---|---|---|
| 1-1'-bicyclopropyl-1-yl | OCF₂H | Cl |
| H | OCF₂H | Br |
| Me | OCF₂H | Br |
| t-Bu | OCF₂H | Br |
| 1-1'-bicyclopropyl-1-yl | OCF₂H | Br |
| 1-CH₃-c-Pr | CF₃ | F |
| 2-CH₃-c-Pr | CF₃ | F |
| 1,1'-bicyclopropyl-2-yl | CF₃ | F |
| H | Br | Br |
| Me | Br | Br |
| Et | Br | Br |
| n-Pr | Br | Br |
| i-Pr | Br | Br |
| n-Bu | Br | Br |
| i-Bu | Br | Br |
| s-Bu | Br | Br |
| t-Bu | Br | Br |
| c-Pr | Br | Br |
| c-PrCH₂ | Br | Br |
| 1-CH₃-c-Pr | Br | Br |
| 2-CH₃-c-Pr | Br | Br |
| 1-1'-bicyclopropyl-2-yl | Br | Br |
| 1-1'-bicyclopropyl-1-yl | Br | Br |
| H | Cl | Br |
| Me | Cl | Br |
| Et | Cl | Br |
| n-Pr | Cl | Br |
| i-Pr | Cl | Br |

TABLE 2-continued

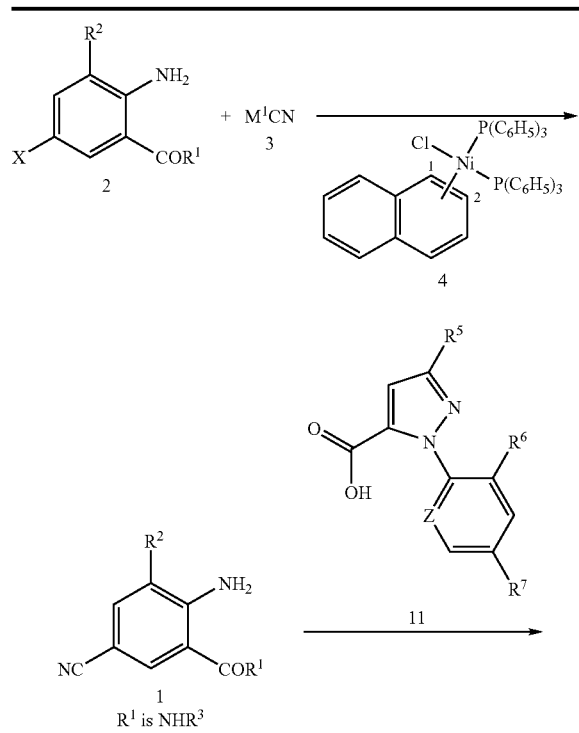

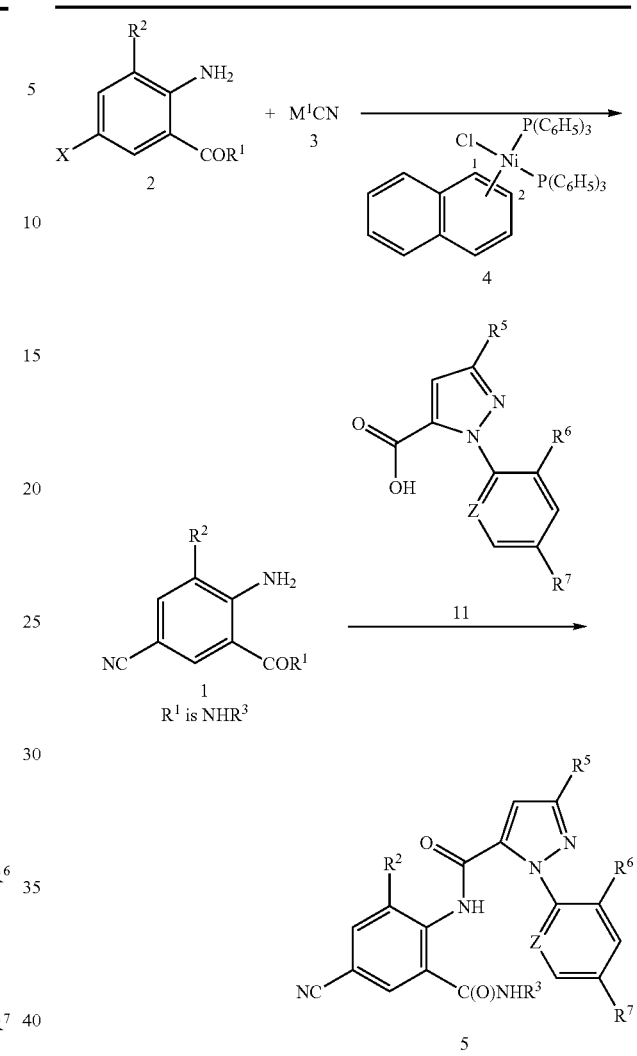

| R³ | R⁵ | R⁶ |
|---|---|---|
| n-Bu | Cl | Br |
| i-Bu | Cl | Br |
| s-Bu | Cl | Br |
| t-Bu | Cl | Br |
| c-Pr | Cl | Br |
| c-PrCH₂ | Cl | Br |
| 1-CH₃-c-Pr | Cl | Br |
| 2-CH₃-c-Pr | Cl | Br |
| 1-1'-bicyclopropyl-2-yl | Cl | Br |
| 1-1'-bicyclopropyl-1-yl | Cl | Br |
| H | CF₃ | Br |
| Me | CF₃ | Br |
| t-Bu | CF₃ | Br |
| 1-CH₃-c-Pr | CF₃ | Br |
| 2-CH₃-c-Pr | CF₃ | Br |
| 1-1'-bicyclopropyl-2-yl | CF₃ | Br |
| 1-1'-bicyclopropyl-1-yl | CF₃ | Br |
| H | CF₃ | Cl |
| Me | CF₃ | Cl |
| t-Bu | CF₃ | Cl |
| 1-CH₃-c-Pr | CF₃ | Cl |
| 2-CH₃-c-Pr | CF₃ | Cl |
| 1-1'-bicyclopropyl-2-yl | CF₃ | Cl |
| 1-1'-bicyclopropyl-1-yl | CF₃ | Cl |
| 1-1'-bicyclopropyl-1-yl | CF₃ | F |

| R³ | R⁵ | R⁶ |
|---|---|---|
| R² is Me, X is Br, R⁷ is H and Z is CH. | | |
| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| 1,1'-bicyclopropyl-1-yl | Cl | F |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | F |
| Me | CF₃ | F |
| Me | OCF₂H | F |
| Et | OCF₂H | F |
| c-PrCH₂ | OCF₂H | F |

TABLE 2-continued

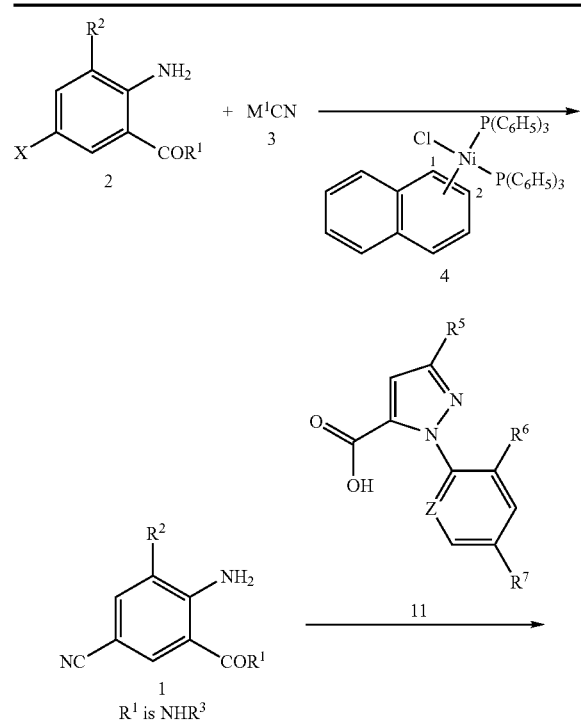

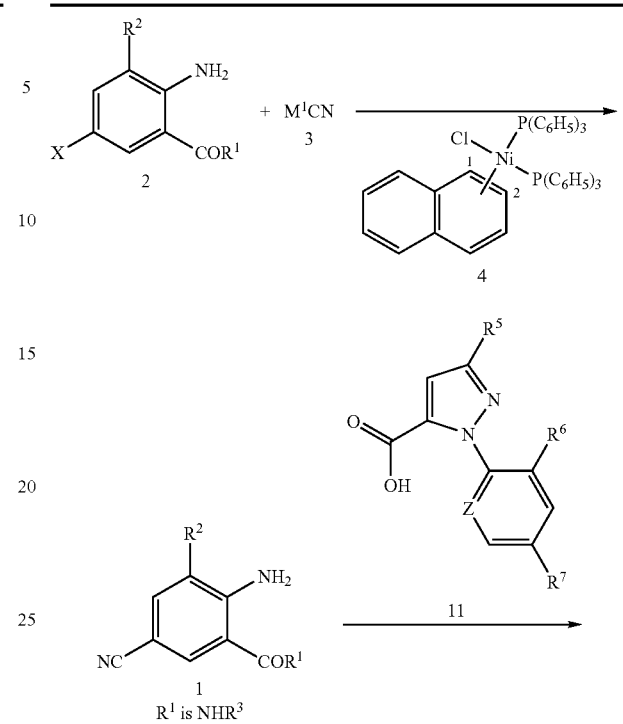

| R³ | R⁵ | R⁶ |
|---|---|---|
| c-Pr | OCF₂H | Cl |
| c-PrCH₂ | OCF₂H | Cl |
| 1,1'-bicyclopropyl-2-yl | OCF₂H | Cl |
| Me | OCF₂H | Br |
| Et | OCF₂H | Br |
| Me | OCH₂CF₃ | F |
| Et | OCH₂CF₃ | F |
| c-Pr | OCH₂CF₃ | F |
| c-PrCH₂ | OCH₂CF₃ | Cl |
| 1,1'-bicyclopropyl-2-yl | OCH₂CF₃ | Cl |
| Me | OCH₂CF₃ | Br |
| Et | OCH₂CF₃ | Br |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-2-yl | Br | Cl |
| 1,1'-bicyclopropyl-1-yl | Br | Cl |
| t-Bu | CF₃ | F |
| H | Br | Br |
| Me | Br | Br |
| t-Bu | Br | Br |
| c-Pr | Br | Br |
| c-PrCH₂ | Br | Br |
| 1,1'-bicyclopropyl-2-yl | Br | Br |
| 1,1'-bicyclopropyl-1-yl | Br | Br |
| H | Cl | Cl |

| R³ | R⁵ | R⁶ |
|---|---|---|
| Me | Cl | Cl |
| t-Bu | Cl | Cl |
| c-Pr | Cl | Cl |
| c-PrCH₂ | Cl | Cl |
| 1,1'-bicyclopropyl-2-yl | Cl | Cl |
| 1,1'-bicyclopropyl-1-yl | Cl | Cl |
| Et | CF₃ | Br |
| c-Pr | CF₃ | Br |
| c-PrCH₂ | CF₃ | Br |
| 1,1'-bicyclopropyl-2-yl | CF₃ | Br |
| H | CF₃ | Cl |
| Me | CF₃ | Cl |
| t-Bu | CF₃ | Cl |
| Me | CF₃ | Cl |
| 2-CH₃-c-Pr | CF₃ | F |

R² is Me, X is Cl, R⁷ is H and Z is CH.

| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH₂ | Cl | F |

TABLE 2-continued

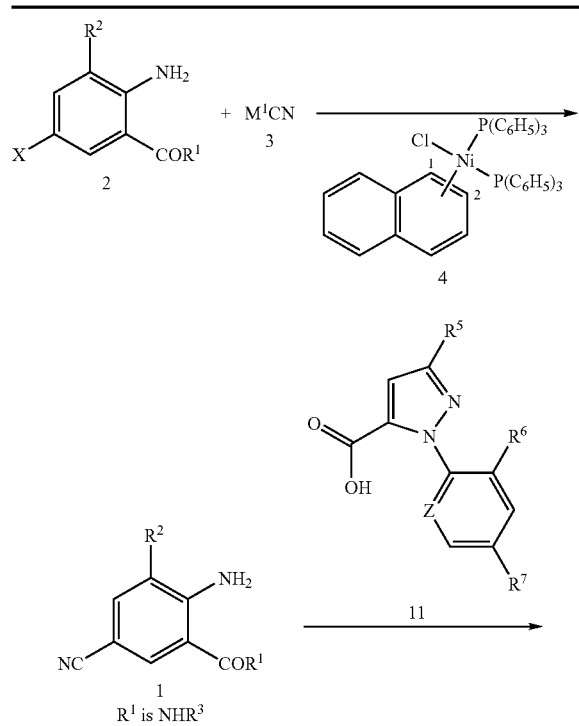

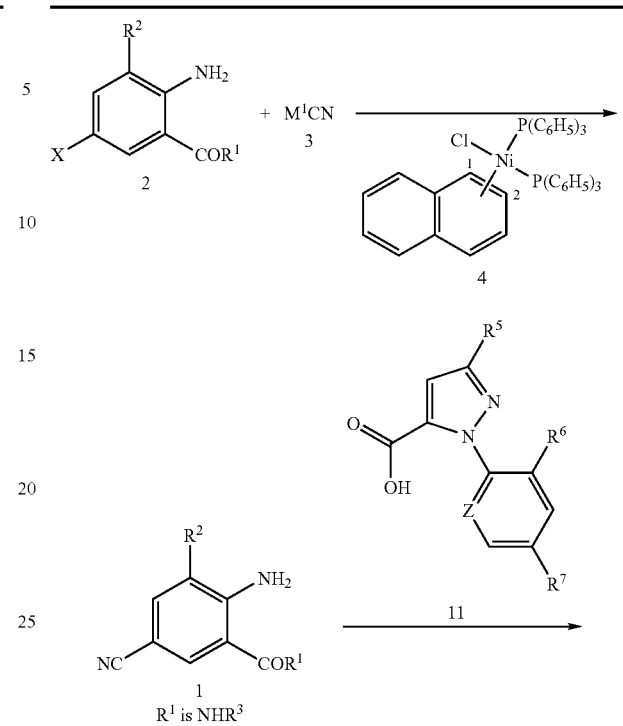

| R³ | R⁵ | R⁶ |
|---|---|---|
| 1,1'-bicyclopropyl-2-yl | Cl | F |
| 1,1'-bicyclopropyl-1-yl | Cl | F |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | F |
| Me | CF₃ | F |
| Me | OCF₂H | F |
| Et | OCF₂H | F |
| c-PrCH₂ | OCF₂H | F |
| c-Pr | OCF₂H | Cl |
| c-PrCH₂ | OCF₂H | Cl |
| 1,1'-bicyclopropyl-2-yl | OCF₂H | Cl |
| Me | OCF₂H | Br |
| Et | OCF₂H | Br |
| Me | OCH₂CF₃ | F |
| Et | OCH₂CF₃ | F |
| c-Pr | OCH₂CF₃ | F |
| c-PrCH₂ | OCH₂CF₃ | Cl |
| 1,1'-bicyclopropyl-2-yl | OCH₂CF₃ | Cl |
| Me | OCH₂CF₃ | Br |
| Et | OCH₂CF₃ | Br |
| H | Br | Cl |
| Me | Br | Cl |

| R³ | R⁵ | R⁶ |
|---|---|---|
| t-Bu | Br | Cl |
| c-Pr | Br | Cl |
| c-PrCH₂ | Br | Cl |
| 1,1'-bicyclopropyl-2-yl | Br | Cl |
| 1,1'-bicyclopropyl-1-yl | Br | Cl |
| t-Bu | CF₃ | F |
| H | Br | Br |
| Me | Br | Br |
| t-Bu | Br | Br |
| c-Pr | Br | Br |
| c-PrCH₂ | Br | Br |
| 1,1'-bicyclopropyl-2-yl | Br | Br |
| 1,1'-bicyclopropyl-1-yl | Br | Br |
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-2-yl | Cl | Cl |
| 1,1'-bicyclopropyl-1-yl | Cl | Cl |
| Et | CF₃ | Br |
| c-Pr | CF₃ | Br |
| c-PrCH₂ | CF₃ | Br |
| 1,1'-bicyclopropyl-2-yl | CF₃ | Br |
| H | CF₃ | Cl |
| Me | CF₃ | Cl |
| t-Bu | CF₃ | Cl |

TABLE 2-continued

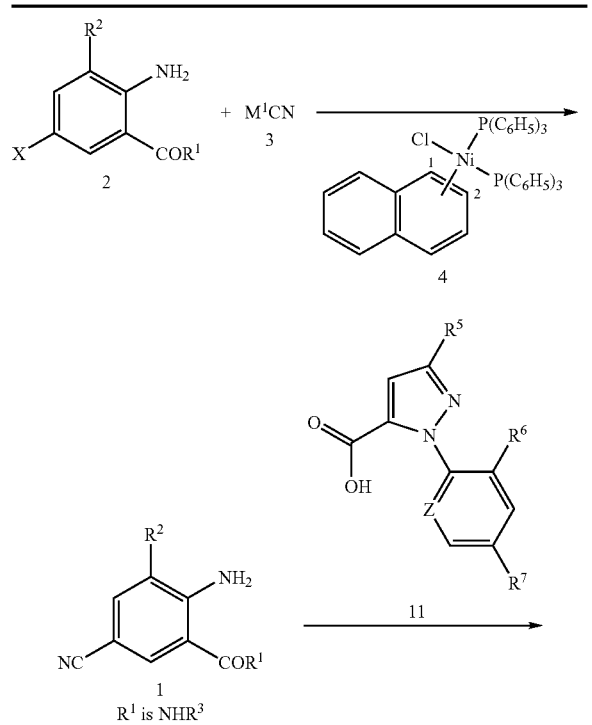

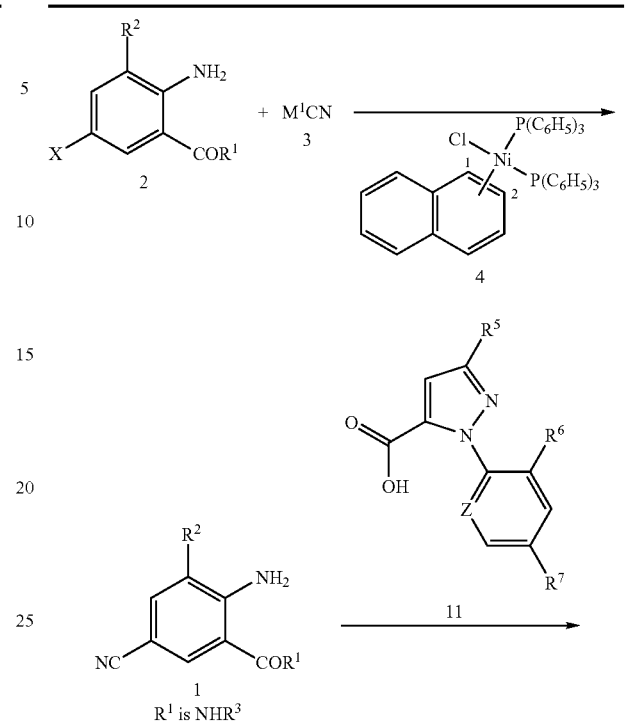

| R³ | R⁵ | R⁶ |
|---|---|---|
| Me | CF₃ | Cl |
| 2-CH₃-c-Pr | CF₃ | F |

R² is Me, X is I, R⁷ is H and Z is CH.

| R³ | R⁵ | R⁶ |
|---|---|---|
| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| 1,1'-bicyclopropyl-1-yl | Cl | F |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | F |
| Me | CF₃ | F |
| Me | OCF₂H | F |

| R³ | R⁵ | R⁶ |
|---|---|---|
| Et | OCF₂H | F |
| c-PrCH₂ | OCF₂H | F |
| c-Pr | OCF₂H | Cl |
| c-PrCH₂ | OCF₂H | Cl |
| 1,1'-bicyclopropyl-2-yl | OCF₂H | Cl |
| Me | OCF₂H | Br |
| Et | OCF₂H | Br |
| Me | OCH₂CF₃ | F |
| Et | OCH₂CF₃ | F |
| c-Pr | OCH₂CF₃ | F |
| c-PrCH₂ | OCH₂CF₃ | Cl |
| 1,1'-bicyclopropyl-2-yl | OCH₂CF₃ | Cl |
| Me | OCH₂CF₃ | Br |
| Et | OCH₂CF₃ | Br |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-2-yl | Br | Cl |
| 1,1'-bicyclopropyl-1-yl | Br | Cl |
| t-Bu | CF₃ | F |
| H | Br | Br |
| Me | Br | Br |
| t-Bu | Br | Br |
| c-Pr | Br | Br |
| c-PrCH₂ | Br | Br |
| 1,1'-bicyclopropyl-2-yl | Br | Br |

TABLE 2-continued

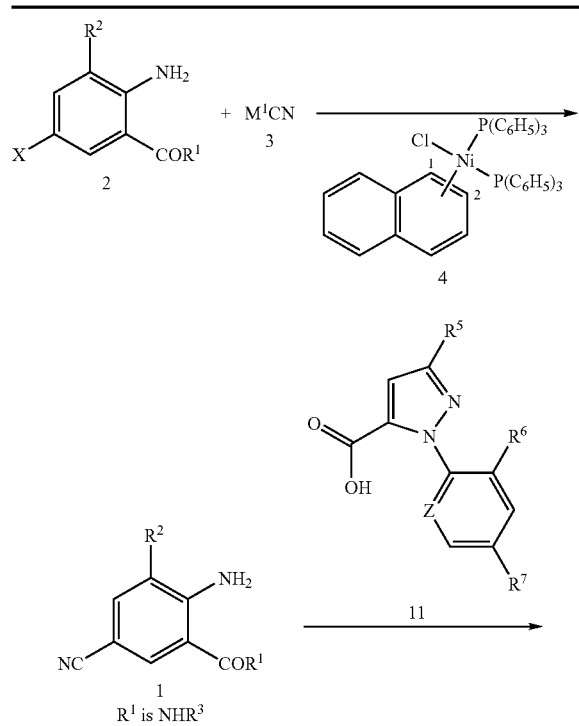

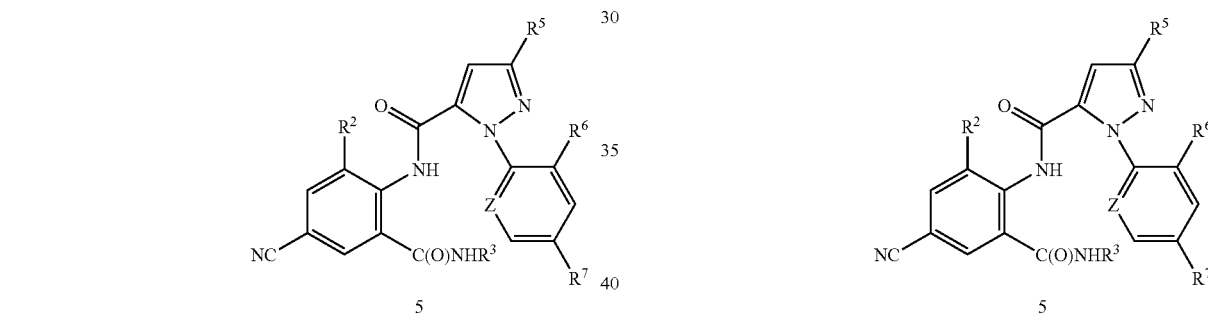

| $R^3$ | $R^5$ | $R^6$ |
|---|---|---|
| 1,1'-bicyclopropyl-1-yl | Br | Br |
| H | Cl | Cl |
| Me | Cl | Cl |
| t-Bu | Cl | Cl |
| c-Pr | Cl | Cl |
| c-PrCH$_2$ | Cl | Cl |
| 1,1'-bicyclopropyl-2-yl | Cl | Cl |
| 1,1'-bicyclopropyl-1-yl | Cl | Cl |
| Et | CF$_3$ | Br |
| c-Pr | CF$_3$ | Br |
| c-PrCH$_2$ | CF$_3$ | Br |
| 1,1'-bicyclopropyl-2-yl | CF$_3$ | Br |
| H | CF$_3$ | Cl |
| Me | CF$_3$ | Cl |
| t-Bu | CF$_3$ | Cl |
| Me | CF$_3$ | Cl |
| 2-CH$_3$-c-Pr | CF$_3$ | F |

$R^2$ is Cl, X is Br, $R^7$ is H and Z is CH.

| H | Br | F |
| Me | Br | F |
| t-Bu | Br | F |
| c-Pr | Br | F |
| c-PrCH$_2$ | Br | F |
| 1,1'-bicyclopropyl-2-yl | Br | F |
| 1,1'-bicyclopropyl-1-yl | Br | F |
| H | Cl | F |
| Me | Cl | F |

TABLE 2-continued

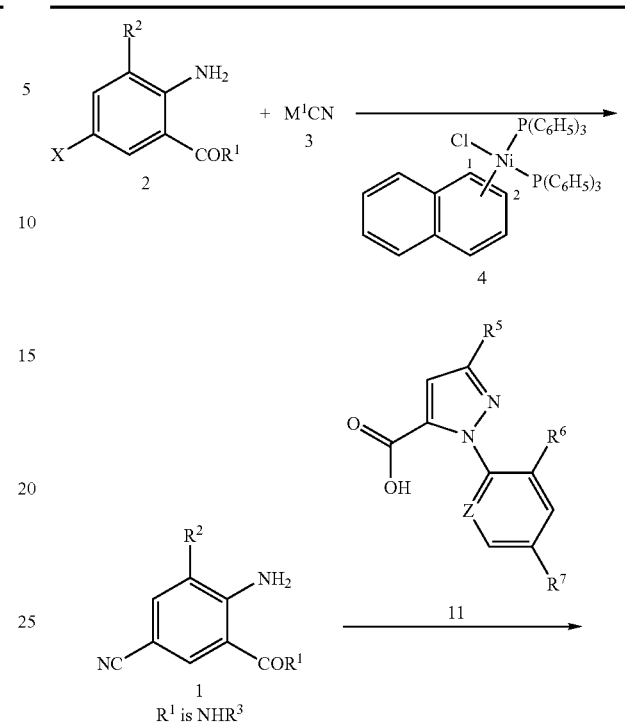

| $R^3$ | $R^5$ | $R^6$ |
|---|---|---|
| t-Bu | Cl | F |
| c-Pr | Cl | F |
| c-PrCH$_2$ | Cl | F |
| 1,1'-bicyclopropyl-2-yl | Cl | F |
| 1,1'-bicyclopropyl-1-yl | Cl | F |
| H | Cl | Br |
| Me | Cl | Br |
| t-Bu | Cl | Br |
| c-Pr | Cl | Br |
| c-PrCH$_2$ | Cl | Br |
| 1,1'-bicyclopropyl-2-yl | Cl | Br |
| 1,1'-bicyclopropyl-1-yl | Cl | Br |
| H | CF$_3$ | F |
| Me | CF$_3$ | F |
| Me | OCF$_2$H | F |
| Et | OCF$_2$H | F |
| c-PrCH$_2$ | OCF$_2$H | F |
| c-Pr | OCF$_2$H | Cl |
| c-PrCH$_2$ | OCF$_2$H | Cl |
| 1,1'-bicyclopropyl-2-yl | OCF$_2$H | Cl |
| Me | OCF$_2$H | Br |
| Et | OCF$_2$H | Br |
| Me | OCH$_2$CF$_3$ | F |
| Et | OCH$_2$CF$_3$ | F |
| c-Pr | OCH$_2$CF$_3$ | F |
| c-PrCH$_2$ | OCH$_2$CF$_3$ | Cl |
| 1,1'-bicyclopropyl-2-yl | OCH$_2$CF$_3$ | Cl |
| Me | OCH$_2$CF$_3$ | Br |

TABLE 2-continued

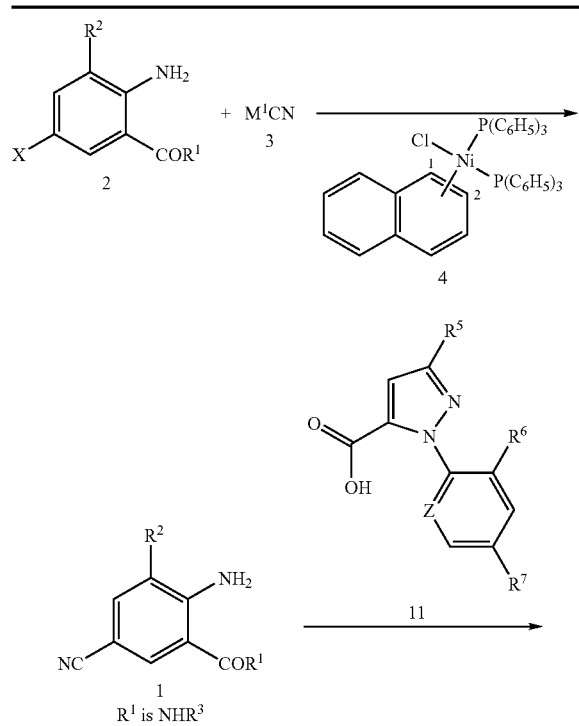

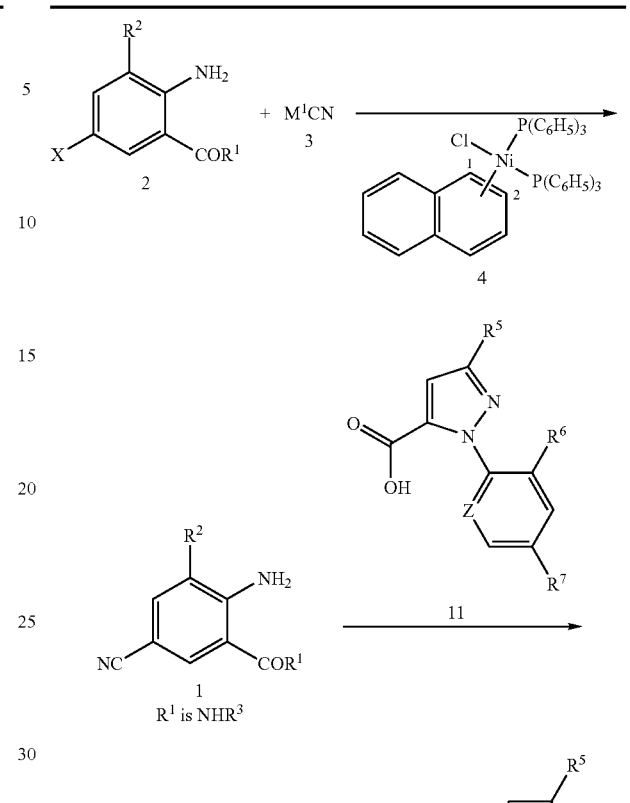

| R³ | R⁵ | R⁶ |
|---|---|---|
| Et | OCH₂CF₃ | Br |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-2-yl | Br | Cl |
| 1,1'-bicyclopropyl-1-yl | Br | Cl |
| t-Bu | CF₃ | F |
| H | Br | Br |
| Me | Br | Br |
| t-Bu | Br | Br |
| c-Pr | Br | Br |
| c-PrCH₂ | Br | Br |
| 1,1'-bicyclopropyl-2-yl | Br | Br |
| 1,1'-bicyclopropyl-1-yl | Br | Br |
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-2-yl | Cl | Cl |
| 1,1'-bicyclopropyl-1-yl | Cl | Cl |
| Et | CF₃ | Br |
| c-Pr | CF₃ | Br |
| c-PrCH₂ | CF₃ | Br |
| 1,1'-bicyclopropyl-2-yl | CF₃ | Br |
| H | CF₃ | Cl |
| Me | CF₃ | Cl |
| t-Bu | CF₃ | Cl |
| Me | CF₃ | Cl |
| 2-CH₃-c-Pr | CF₃ | F |

R² is Cl, X is I, R⁷ is H and Z is CH.

| R³ | R⁵ | R⁶ |
|---|---|---|
| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| 1,1'-bicyclopropyl-1-yl | Cl | F |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | F |

TABLE 2-continued

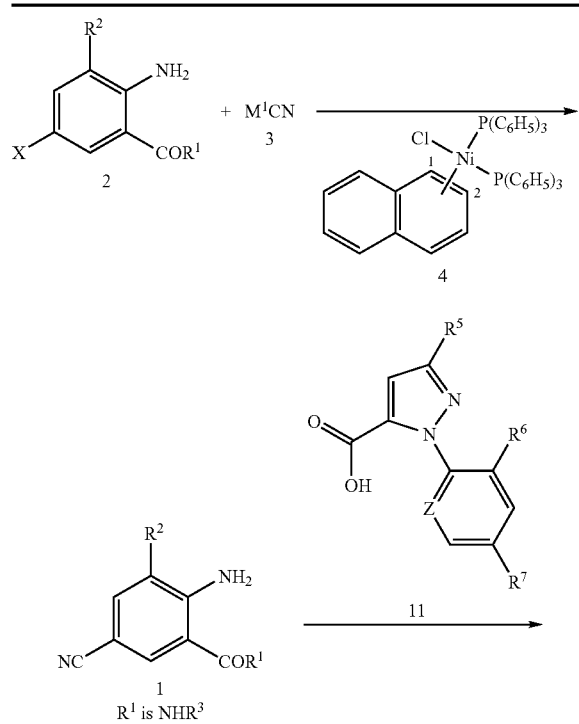

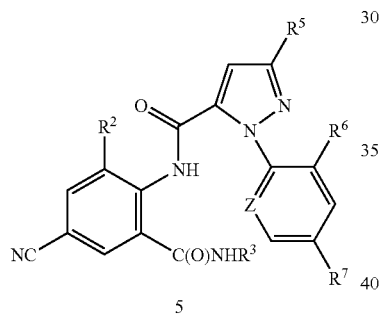

| R³ | R⁵ | R⁶ |
|---|---|---|
| Me | CF₃ | F |
| Me | OCF₂H | F |
| Et | OCF₂H | F |
| c-PrCH₂ | OCF₂H | F |
| c-Pr | OCF₂H | Cl |
| c-PrCH₂ | OCF₂H | Cl |
| 1,1'-bicyclopropyl-2-yl | OCF₂H | Cl |
| Me | OCF₂H | Br |
| Et | OCF₂H | Br |
| Me | OCH₂CF₃ | F |
| Et | OCH₂CF₃ | F |
| c-Pr | OCH₂CF₃ | F |
| c-PrCH₂ | OCH₂CF₃ | Cl |
| 1,1'-bicyclopropyl-2-yl | OCH₂CF₃ | Cl |
| Me | OCH₂CF₃ | Br |
| Et | OCH₂CF₃ | Br |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-2-yl | Br | Cl |
| 1,1'-bicyclopropyl-1-yl | Br | Cl |
| t-Bu | CF₃ | F |
| H | Br | Br |
| Me | Br | Br |
| t-Bu | Br | Br |
| c-Pr | Br | Br |

TABLE 2-continued

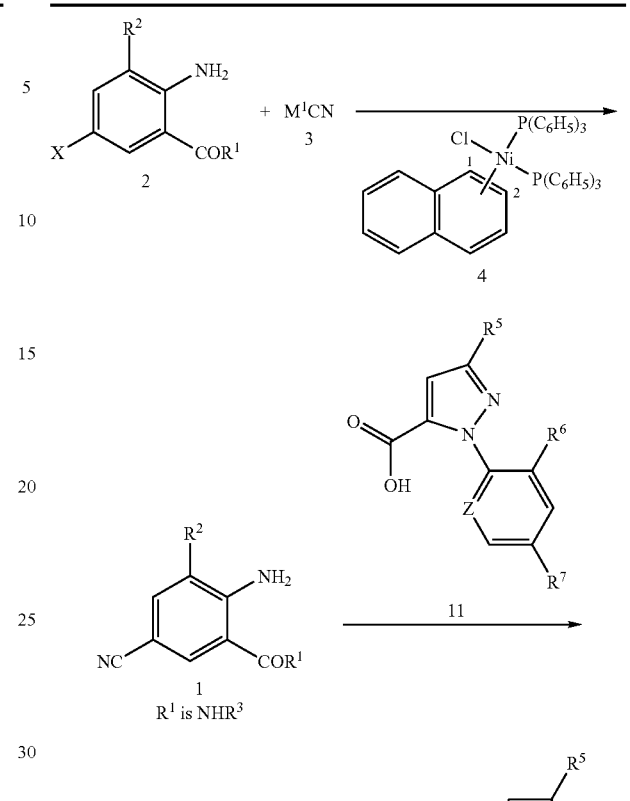

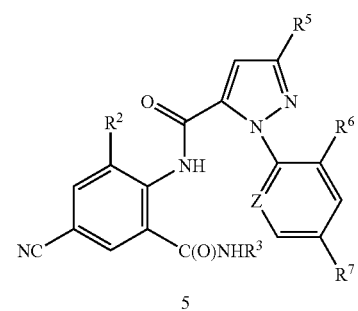

| R³ | R⁵ | R⁶ |
|---|---|---|
| c-PrCH₂ | Br | Br |
| 1,1'-bicyclopropyl-2-yl | Br | Br |
| 1,1'-bicyclopropyl-1-yl | Br | Br |
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-2-yl | Cl | Cl |
| 1,1'-bicyclopropyl-1-yl | Cl | Cl |
| Et | CF₃ | Br |
| c-Pr | CF₃ | Br |
| c-PrCH₂ | CF₃ | Br |
| 1,1'-bicyclopropyl-2-yl | CF₃ | Br |
| H | CF₃ | Cl |
| Me | CF₃ | Cl |
| t-Bu | CF₃ | Cl |
| Me | CF₃ | Cl |
| 2-CH₃-c-Pr | CF₃ | F |

R² is Me, X is Br, R⁷ is F and Z is N.

| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |

TABLE 2-continued

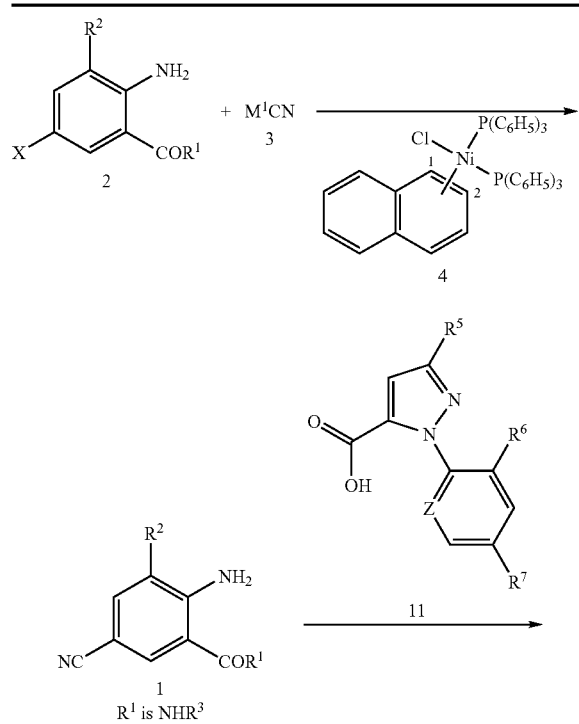

| R³ | R⁵ | R⁶ |
|---|---|---|
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-1-yl | Br | Cl |
| H | CF₃ | Cl |
| Me | CF₃ | Cl |
| t-Bu | CF₃ | Cl |
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-1-yl | Cl | Cl |
| Me | OCF₂H | F |
| Et | OCF₂H | F |
| c-Pr | OCF₂H | Cl |
| c-PrCH₂ | OCF₂H | Cl |
| 1,1'-bicyclopropyl-1-yl | OCF₂H | Cl |
| Me | OCF₂H | Br |
| Et | OCF₂H | Br |

TABLE 2-continued

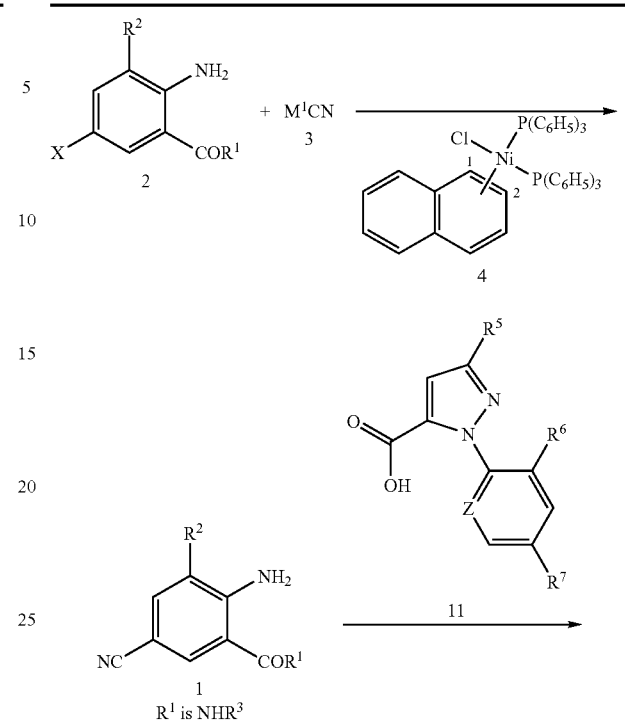

| R³ | R⁵ | R⁶ |
|---|---|---|
| Me | OCH₂CF₃ | F |
| Et | OCH₂CF₃ | F |
| c-Pr | OCH₂CF₃ | Cl |
| c-PrCH₂ | OCH₂CF₃ | Cl |
| 1,1'-bicyclopropyl-1-yl | OCH₂CF₃ | Cl |
| Me | OCH₂CF₃ | Br |
| Et | OCH₂CF₃ | Br |
| 1,1'-bicyclopropyl-2-yl | CF₃ | Cl |
| Me | CF₃ | Br |
| H | Br | Br |
| Me | Br | Br |
| t-Bu | Br | Br |
| c-Pr | Br | Br |
| c-PrCH₂ | Br | Br |
| 1,1'-bicyclopropyl-2-yl | Br | Br |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | F |
| Me | CF₃ | F |
| t-Bu | CF₃ | F |
| 2-CH₃-c-Pr | CF₃ | F |
| 1,1'-bicyclopropyl-2-yl | CF₃ | F |
| Et | CF₃ | Br |

TABLE 2-continued

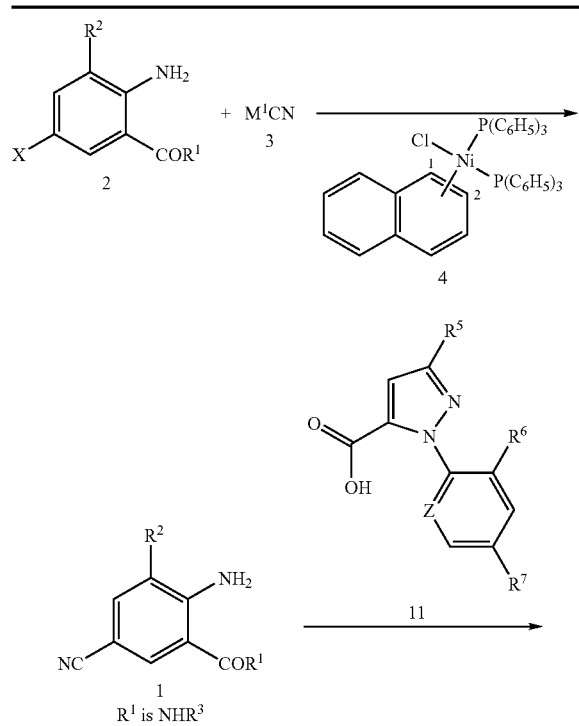
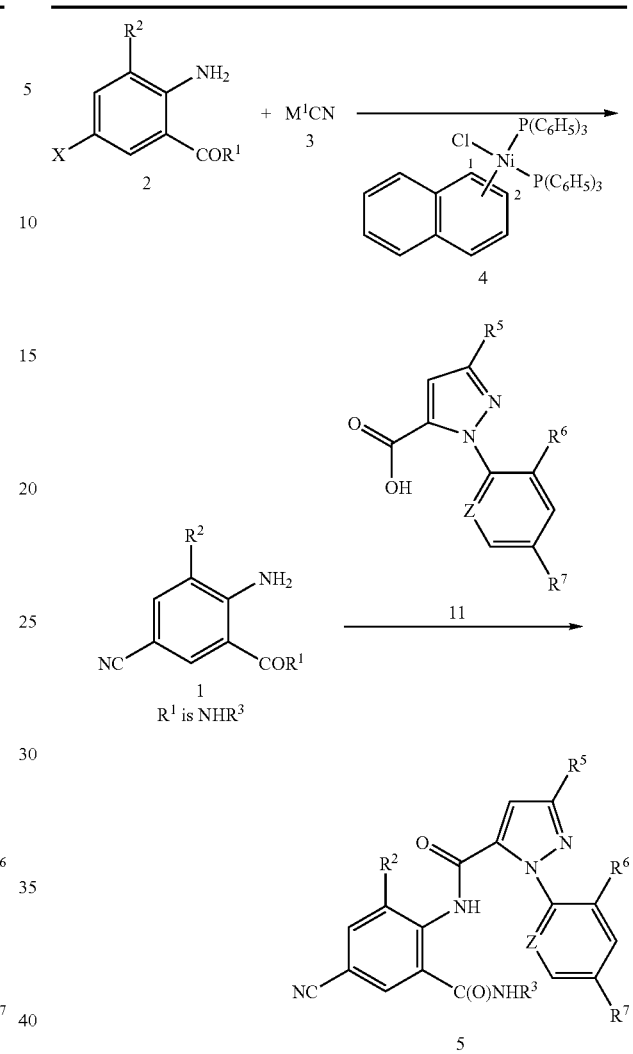

| $R^3$ | $R^5$ | $R^6$ |
|---|---|---|
| c-Pr | $CF_3$ | Br |
| c-PrCH$_2$ | $CF_3$ | Br |
| 1,1'-bicyclopropyl-2-yl | $CF_3$ | Br |

$R^2$ is Me, X is Cl, $R^7$ is F and Z is N.

| $R^3$ | $R^5$ | $R^6$ |
|---|---|---|
| H | Br | F |
| Me | Br | F |
| t-Bu | Br | F |
| c-Pr | Br | F |
| c-PrCH$_2$ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH$_2$ | Cl | F |
| 1,1'-bicyclopropyl-2-yl | Cl | F |
| H | Br | Cl |
| Me | Br | Cl |
| t-Bu | Br | Cl |
| c-Pr | Br | Cl |
| c-PrCH$_2$ | Br | Cl |
| 1,1'-bicyclopropyl-1-yl | Br | Cl |
| H | $CF_3$ | Cl |
| Me | $CF_3$ | Cl |
| t-Bu | $CF_3$ | Cl |
| H | Cl | Cl |
| Me | Cl | Cl |
| t-Bu | Cl | Cl |
| c-Pr | Cl | Cl |
| c-PrCH$_2$ | Cl | Cl |
| 1,1'-bicyclopropyl-1-yl | Cl | Cl |
| Me | OCF$_2$H | F |
| Et | OCF$_2$H | F |
| c-Pr | OCF$_2$H | Cl |
| c-PrCH$_2$ | OCF$_2$H | Cl |
| 1,1'-bicyclopropyl-1-yl | OCF$_2$H | Cl |
| Me | OCF$_2$H | Br |
| Et | OCF$_2$H | Br |
| Me | OCH$_2$CF$_3$ | F |
| Et | OCH$_2$CF$_3$ | F |
| c-Pr | OCH$_2$CF$_3$ | Cl |
| c-PrCH$_2$ | OCH$_2$CF$_3$ | Cl |
| 1,1'-bicyclopropyl-1-yl | OCH$_2$CF$_3$ | Cl |
| Me | OCH$_2$CF$_3$ | Br |
| Et | OCH$_2$CF$_3$ | Br |
| 1,1'-bicyclopropyl-2-yl | $CF_3$ | Cl |
| Me | $CF_3$ | Br |
| H | Br | Br |
| Me | Br | Br |
| t-Bu | Br | Br |
| c-Pr | Br | Br |
| c-PrCH$_2$ | Br | Br |
| 1,1'-bicyclopropyl-1-yl | Br | Br |
| H | Cl | Br |

TABLE 2-continued

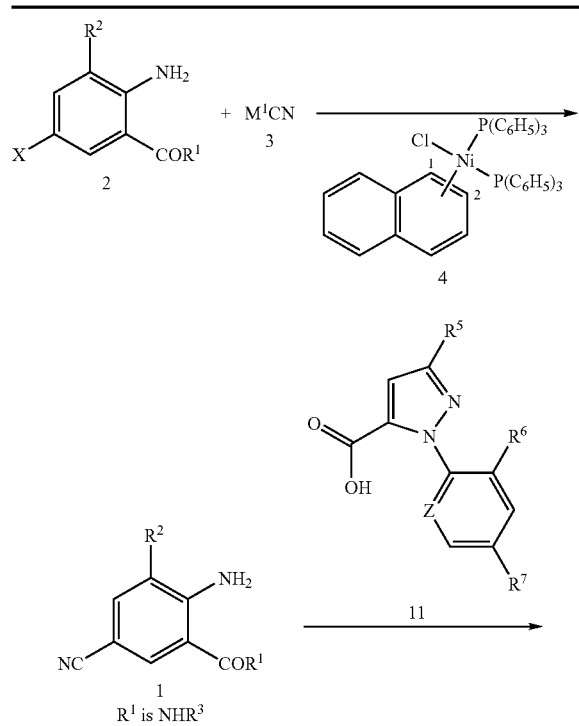

| R³ | R⁵ | R⁶ |
|---|---|---|
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | F |
| Me | CF₃ | F |
| t-Bu | CF₃ | F |
| 2-CH₃-c-Pr | CF₃ | F |
| 1,1'-bicyclopropyl-2-yl | CF₃ | F |
| Et | CF₃ | Br |
| c-Pr | CF₃ | Br |
| c-PrCH₂ | CF₃ | Br |
| 1,1'-bicyclopropyl-2-yl | CF₃ | Br |

R² is Me, X is I, R⁷ is F and Z is N.

| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |

TABLE 2-continued

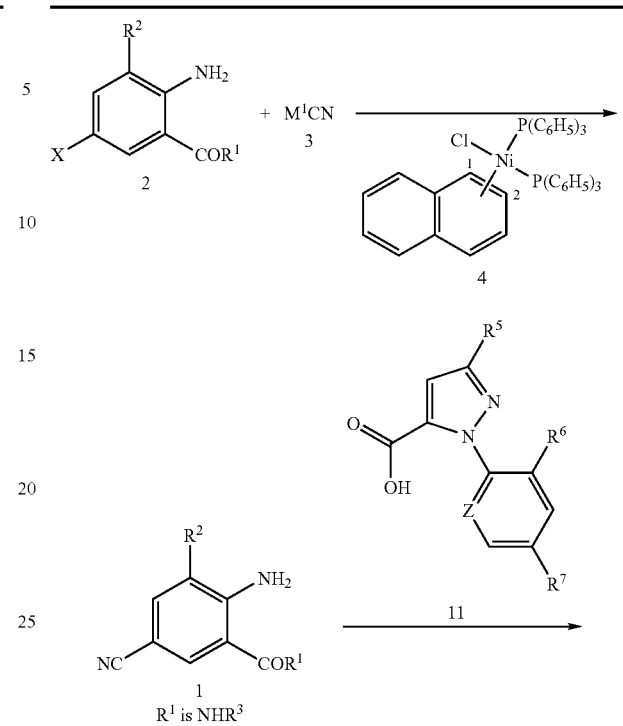

| R³ | R⁵ | R⁶ |
|---|---|---|
| c-PrCH₂ | Cl | F |
| 1,1'-bicyclopropyl-2-yl | Cl | F |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-1-yl | Br | Cl |
| H | CF₃ | Cl |
| Me | CF₃ | Cl |
| t-Bu | CF₃ | Cl |
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-1-yl | Cl | Cl |
| Me | OCF₂H | F |
| Et | OCF₂H | F |
| c-Pr | OCF₂H | Cl |
| c-PrCH₂ | OCF₂H | Cl |
| 1,1'-bicyclopropyl-1-yl | OCF₂H | Cl |
| Me | OCF₂H | Br |
| Et | OCF₂H | Br |
| Me | OCH₂CF₃ | F |
| Et | OCH₂CF₃ | F |
| c-Pr | OCH₂CF₃ | Cl |
| c-PrCH₂ | OCH₂CF₃ | Cl |

TABLE 2-continued

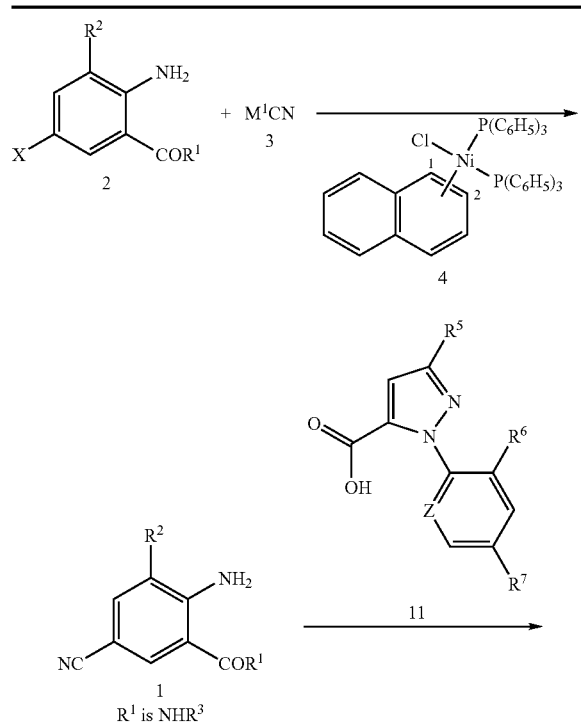
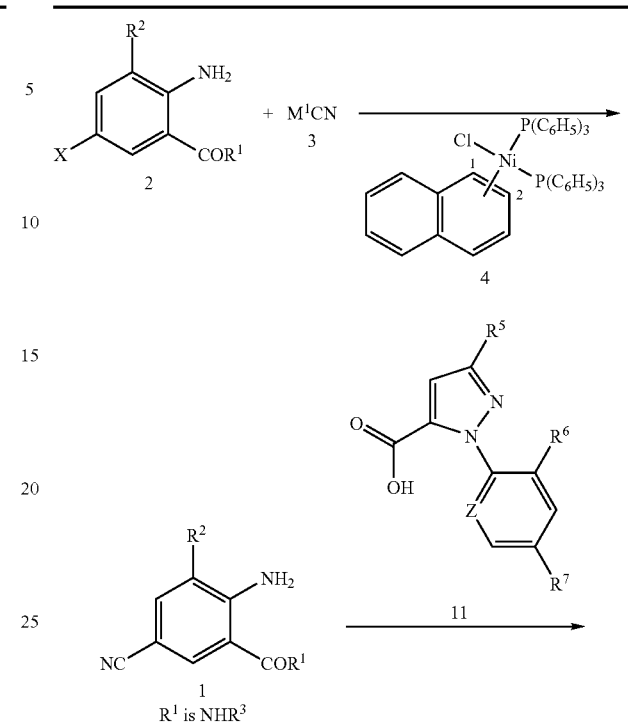

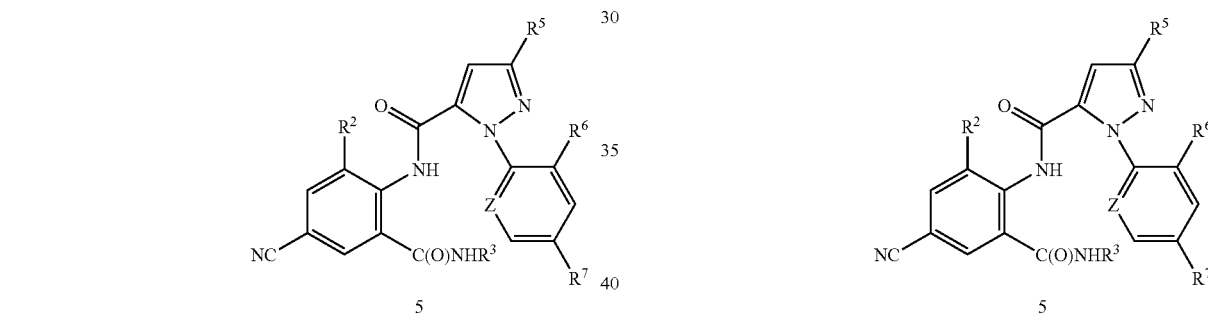

| R³ | R⁵ | R⁶ |
|---|---|---|
| 1,1'-bicyclopropyl-1-yl | OCH₂CF₃ | Cl |
| Me | OCH₂CF₃ | Br |
| Et | OCH₂CF₃ | Br |
| Me | CF₃ | Br |
| 1,1'-bicyclopropyl-2-yl | CF₃ | Cl |
| H | Br | Br |
| Me | Br | Br |
| t-Bu | Br | Br |
| c-Pr | Br | Br |
| c-PrCH₂ | Br | Br |
| 1,1'-bicyclopropyl-1-yl | Br | Br |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | F |
| Me | CF₃ | F |
| t-Bu | CF₃ | F |
| 2-CH₃-c-Pr | CF₃ | F |
| 1,1'-bicyclopropyl-2-yl | CF₃ | F |
| Et | CF₃ | Br |
| c-Pr | CF₃ | Br |
| c-PrCH₂ | CF₃ | Br |
| 1,1'-bicyclopropyl-2-yl | CF₃ | Br |

| R³ | R⁵ | R⁶ |
|---|---|---|
| R² is Cl, X is Br, R⁷ is F and Z is N. | | |
| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-1-yl | Br | Cl |
| H | CF₃ | Cl |
| Me | CF₃ | Cl |
| t-Bu | CF₃ | Cl |
| H | Cl | Cl |
| Me | Cl | Cl |
| t-Bu | Cl | Cl |
| c-Pr | Cl | Cl |

TABLE 2-continued

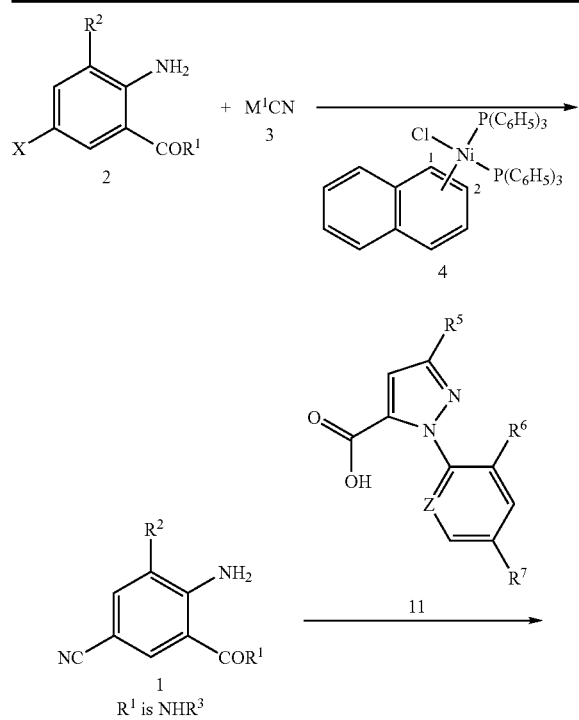
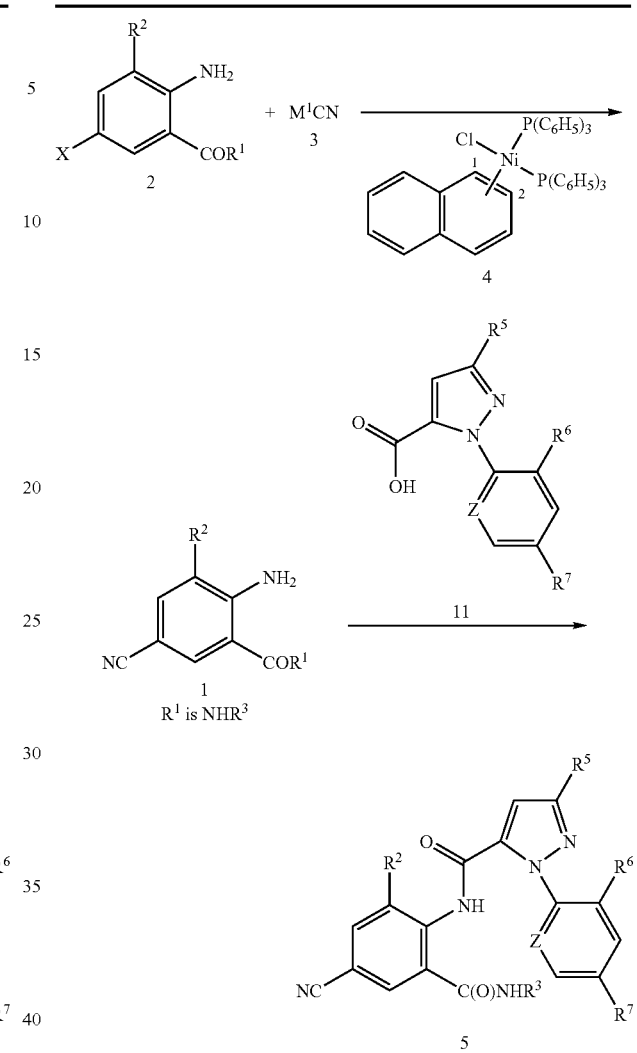

| R³ | R⁵ | R⁶ |
|---|---|---|
| c-PrCH₂ | Cl | Cl |
| 1,1'-bicyclopropyl-1-yl | Cl | Cl |
| Me | OCF₂H | F |
| Et | OCF₂H | F |
| c-Pr | OCF₂H | Cl |
| c-PrCH₂ | OCF₂H | Cl |
| 1,1'-bicyclopropyl-1-yl | OCF₂H | Cl |
| Me | OCF₂H | Br |
| Et | OCF₂H | Br |
| Me | OCH₂CF₃ | F |
| Et | OCH₂CF₃ | F |
| c-Pr | OCH₂CF₃ | Cl |
| c-PrCH₂ | OCH₂CF₃ | Cl |
| 1,1'-bicyclopropyl-1-yl | OCH₂CF₃ | Cl |
| Me | OCH₂CF₃ | Br |
| Et | OCH₂CF₃ | Br |
| 1,1'-bicyclopropyl-2-yl | CF₃ | Cl |
| Me | CF₃ | Br |
| H | Br | Br |
| Me | Br | Br |
| t-Bu | Br | Br |
| c-Pr | Br | Br |
| c-PrCH₂ | Br | Br |
| 1,1'-bicyclopropyl-1-yl | Br | Br |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | F |
| Me | CF₃ | F |
| t-Bu | CF₃ | F |
| 2-CH₃-c-Pr | CF₃ | F |
| 1,1'-bicyclopropyl-2-yl | CF₃ | F |
| Et | CF₃ | Br |
| c-Pr | CF₃ | Br |
| c-PrCH₂ | CF₃ | Br |
| 1,1'-bicyclopropyl-2-yl | CF₃ | Br |

R² is Cl, X is I, R⁷ is F and Z is N.

| R³ | R⁵ | R⁶ |
|---|---|---|
| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| H | Br | Cl |

TABLE 2-continued

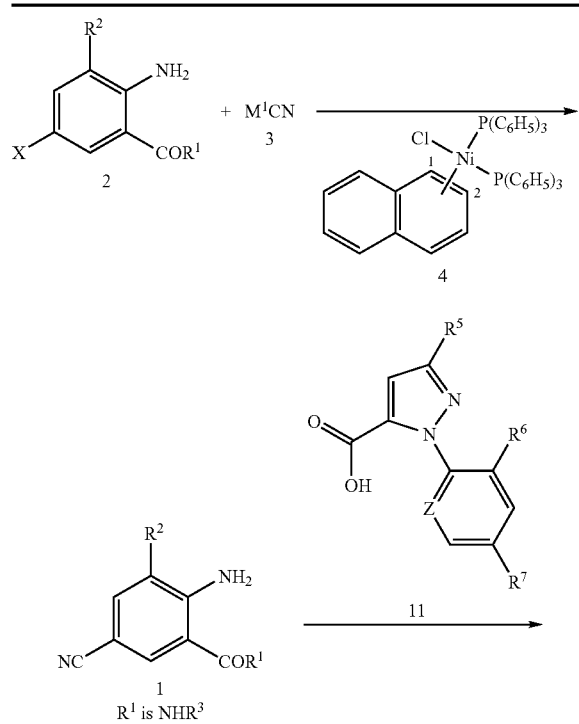

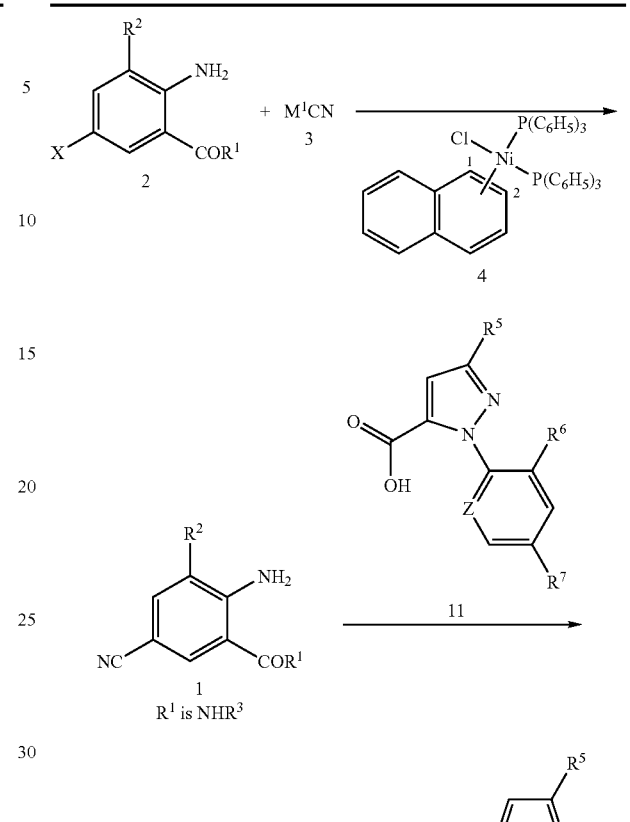

| R³ | R⁵ | R⁶ |
|---|---|---|
| Me | Br | Cl |
| t-Bu | Br | Cl |
| c-Pr | Br | Cl |
| c-PrCH₂ | Br | Cl |
| 1,1'-bicyclopropyl-1-yl | Br | Cl |
| H | CF₃ | Cl |
| Me | CF₃ | Cl |
| t-Bu | CF₃ | Cl |
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-1-yl | Cl | Cl |
| Me | OCF₂H | F |
| Et | OCF₂H | F |
| c-Pr | OCF₂H | Cl |
| c-PrCH₂ | OCF₂H | Cl |
| 1,1'-bicyclopropyl-1-yl | OCF₂H | Cl |
| Me | OCF₂H | Br |
| Et | OCF₂H | Br |
| Me | OCH₂CF₃ | F |
| Et | OCH₂CF₃ | F |
| c-Pr | OCH₂CF₃ | Cl |
| c-PrCH₂ | OCH₂CF₃ | Cl |
| 1,1'-bicyclopropyl-1-yl | OCH₂CF₃ | Cl |
| Me | OCH₂CF₃ | Br |
| Et | OCH₂CF₃ | Br |

| R³ | R⁵ | R⁶ |
|---|---|---|
| 1,1'-bicyclopropyl-2-yl | CF₃ | Cl |
| Me | CF₃ | Br |
| H | Br | Br |
| Me | Br | Br |
| t-Bu | Br | Br |
| c-Pr | Br | Br |
| c-PrCH₂ | Br | Br |
| 1,1'-bicyclopropyl-1-yl | Br | Br |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | F |
| Me | CF₃ | F |
| t-Bu | CF₃ | F |
| 2-CH₃-c-Pr | CF₃ | F |
| 1,1'-bicyclopropyl-2-yl | CF₃ | F |
| Et | CF₃ | Br |
| c-Pr | CF₃ | Br |
| c-PrCH₂ | CF₃ | Br |
| 1,1'-bicyclopropyl-2-yl | CF₃ | Br |

R² is Me, X is Br, R⁷ is Cl and Z is N.

| | | |
|---|---|---|
| H | Br | F |
| Me | Br | F |

TABLE 2-continued

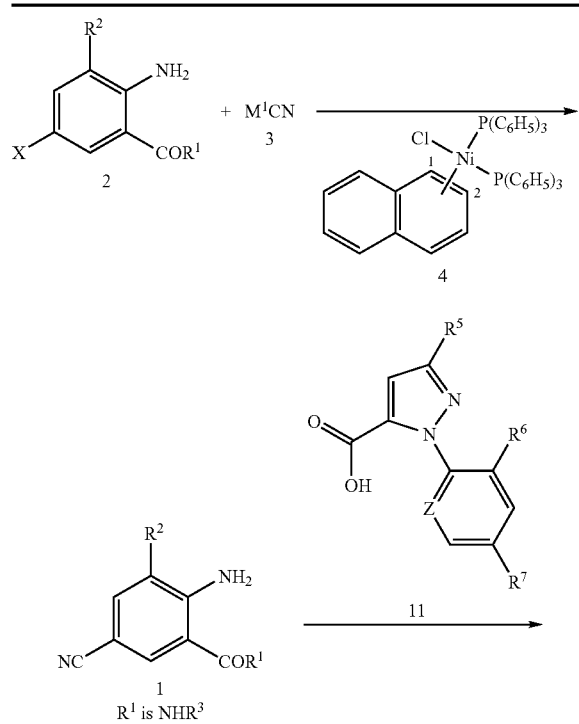

| $R^3$ | $R^5$ | $R^6$ |
|---|---|---|
| t-Bu | Br | F |
| c-Pr | Br | F |
| c-PrCH$_2$ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH$_2$ | Cl | F |
| 1,1'-bicyclopropyl-2-yl | Cl | F |
| H | Br | Cl |
| Me | Br | Cl |
| t-Bu | Br | Cl |
| c-Pr | Br | Cl |
| c-PrCH$_2$ | Br | Cl |
| 1,1'-bicyclopropyl-2-yl | Br | Cl |
| H | CF$_3$ | F |
| Me | CF$_3$ | F |
| t-Bu | CF$_3$ | F |
| H | Cl | Cl |
| Me | Cl | Cl |
| t-Bu | Cl | Cl |
| c-Pr | Cl | Cl |
| c-PrCH$_2$ | Cl | Cl |
| 1,1'-bicyclopropyl-2-yl | Cl | Cl |
| 1,1'-bicyclopropyl-1-yl | Cl | Cl |
| Me | OCH$_2$CF$_3$ | F |

TABLE 2-continued

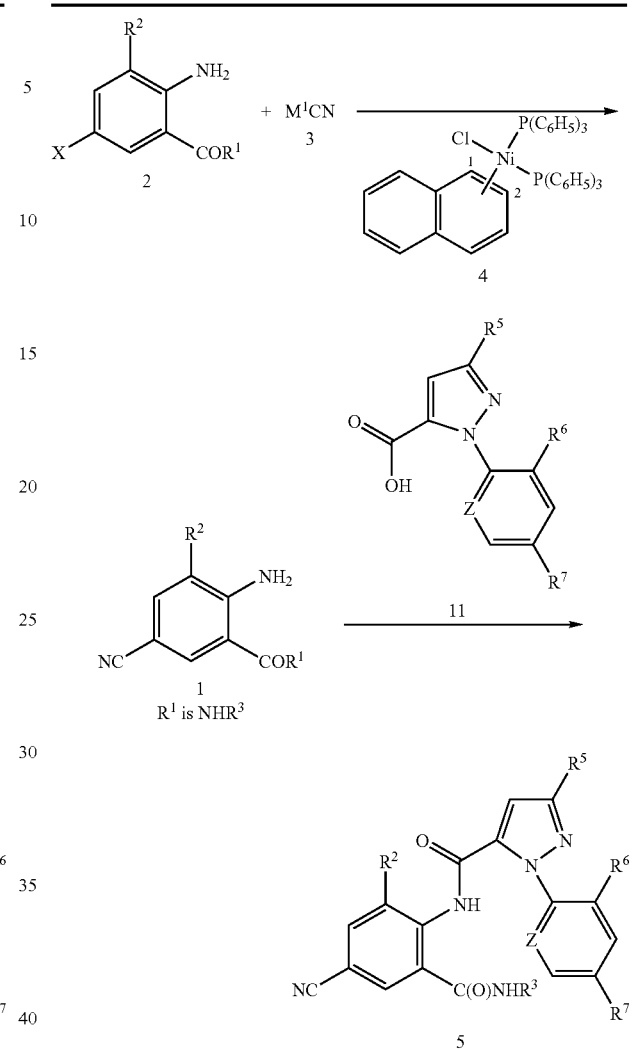

| $R^3$ | $R^5$ | $R^6$ |
|---|---|---|
| Et | OCH$_2$CF$_3$ | F |
| c-Pr | OCH$_2$CF$_3$ | Cl |
| c-PrCH$_2$ | OCH$_2$CF$_3$ | Cl |
| 1,1'-bicyclopropyl-1-yl | OCH$_2$CF$_3$ | Cl |
| Me | OCH$_2$CF$_3$ | Br |
| Et | OCH$_2$CF$_3$ | Br |
| Me | OCF$_2$H | F |
| Et | OCF$_2$H | F |
| c-Pr | OCF$_2$H | Cl |
| c-PrCH$_2$ | OCF$_2$H | Cl |
| 1,1'-bicyclopropyl-2-yl | OCF$_2$H | F |
| Me | OCF$_2$H | Br |
| Et | OCF$_2$H | Br |
| 2-CH$_3$-c-Pr | CF$_3$ | F |
| H | Br | Br |
| Me | Br | Br |
| t-Bu | Br | Br |
| c-Pr | Br | Br |
| c-PrCH$_2$ | Br | Br |
| 1,1'-bicyclopropyl-1-yl | Br | Br |
| H | Cl | Br |
| Me | Cl | Br |
| t-Bu | Cl | Br |
| c-Pr | Cl | Br |
| c-PrCH$_2$ | Cl | Br |
| 1,1'-bicyclopropyl-2-yl | Cl | Br |
| 1,1'-bicyclopropyl-1-yl | Cl | Br |
| H | CF$_3$ | Cl |

TABLE 2-continued

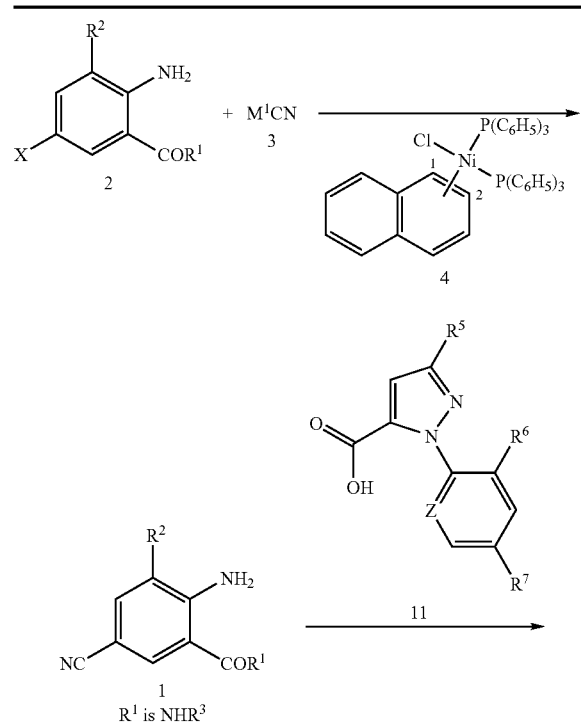

| R³ | R⁵ | R⁶ |
|---|---|---|
| Me | CF₃ | Cl |
| t-Bu | CF₃ | Cl |
| Me | CF₃ | Br |
| Et | CF₃ | Br |
| c-Pr | CF₃ | Br |
| c-PrCH₂ | CF₃ | Br |
| 1,1'-bicyclopropyl-2-yl | CF₃ | Br |
| 1,1'-bicyclopropyl-1-yl | CF₃ | F |

$R^2$ is Me, X is Cl, $R^7$ is Cl and Z is N.

| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| H | Br | Cl |
| Me | Br | Cl |
| t-Bu | Br | Cl |
| c-Pr | Br | Cl |
| c-PrCH₂ | Br | Cl |

TABLE 2-continued

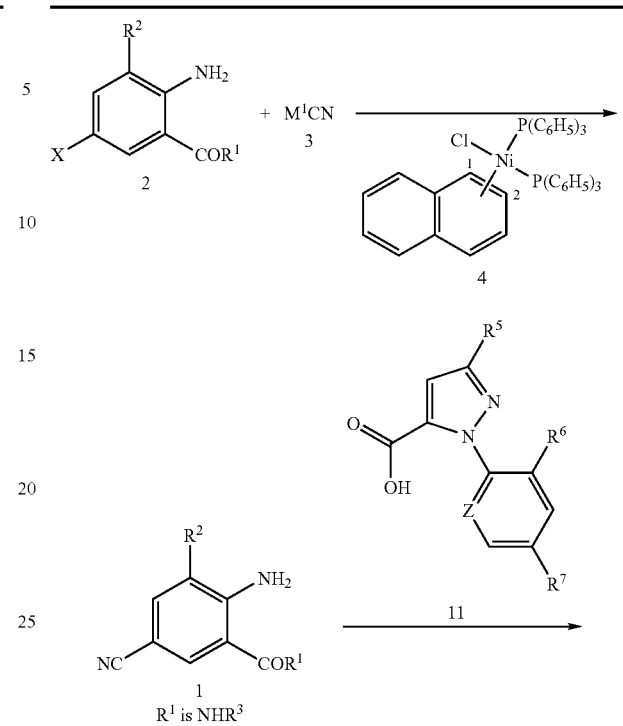

| R³ | R⁵ | R⁶ |
|---|---|---|
| 1,1'-bicyclopropyl-2-yl | Br | Cl |
| H | CF₃ | F |
| Me | CF₃ | F |
| t-Bu | CF₃ | F |
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-1-yl | Cl | Cl |
| 1,1'-bicyclopropyl-2-yl | Cl | Cl |
| Me | OCH₂CF₃ | F |
| Et | OCH₂CF₃ | F |
| c-Pr | OCH₂CF₃ | Cl |
| c-PrCH₂ | OCH₂CF₃ | Cl |
| 1,1'-bicyclopropyl-1-yl | OCH₂CF₃ | Cl |
| Me | OCH₂CF₃ | Br |
| Et | OCH₂CF₃ | Br |
| Me | OCF₂H | F |
| Et | OCF₂H | F |
| c-Pr | OCF₂H | Cl |
| c-PrCH₂ | OCF₂H | Cl |
| 1,1'-bicyclopropyl-2-yl | OCF₂H | F |
| Me | OCF₂H | Br |
| Et | OCF₂H | Br |
| 2-CH₃-c-Pr | CF₃ | F |
| H | Br | Br |
| Me | Br | Br |

TABLE 2-continued

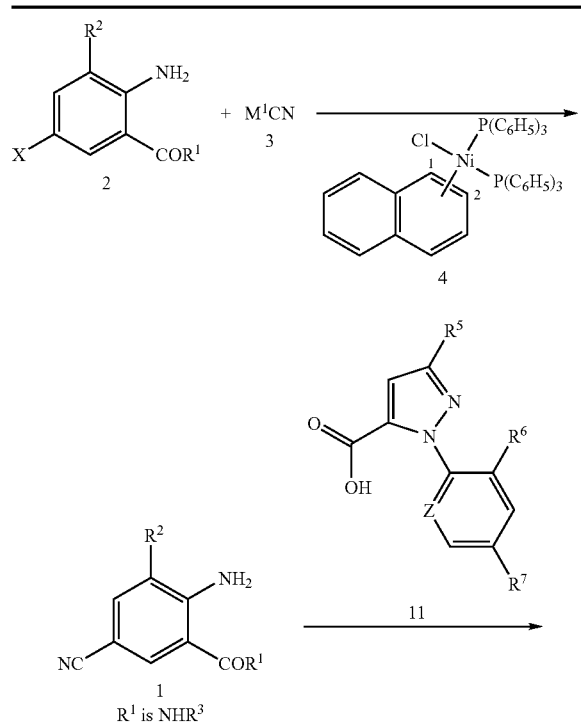

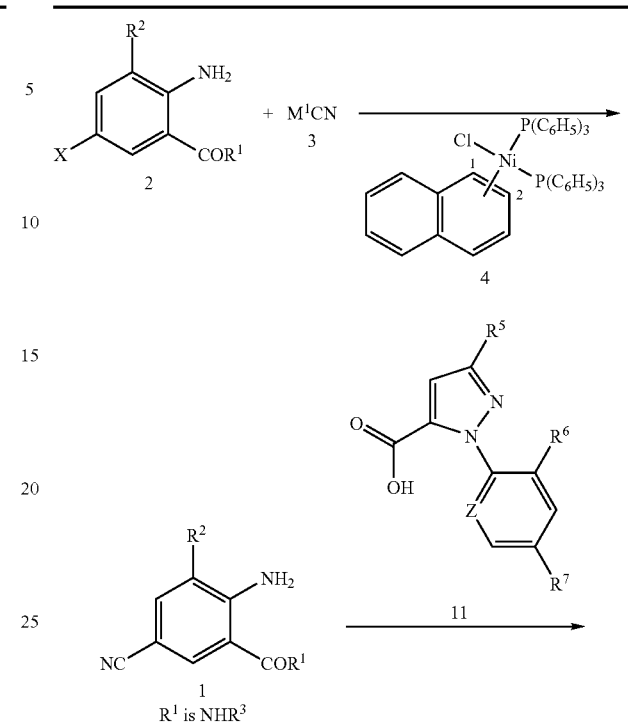

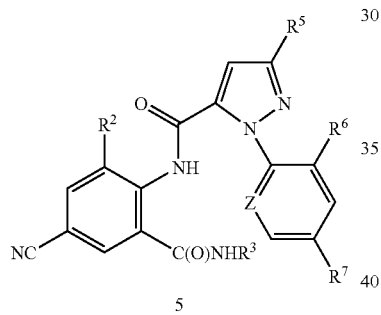

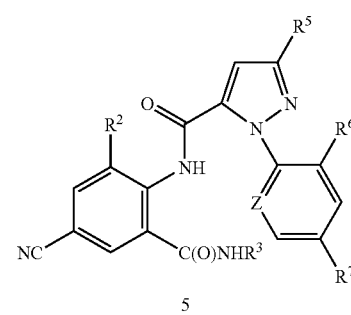

| R³ | R⁵ | R⁶ |
|---|---|---|
| t-Bu | Br | Br |
| c-Pr | Br | Br |
| c-PrCH₂ | Br | Br |
| 1,1'-bicyclopropyl-1-yl | Br | Br |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | Cl |
| Me | CF₃ | Cl |
| t-Bu | CF₃ | Cl |
| Me | CF₃ | Br |
| Et | CF₃ | Br |
| c-Pr | CF₃ | Br |
| c-PrCH₂ | CF₃ | Br |
| 1,1'-bicyclopropyl-2-yl | CF₃ | Br |
| 1,1'-bicyclopropyl-1-yl | CF₃ | F |

R² is Me, X is I, R⁷ is Cl and Z is N.

| R³ | R⁵ | R⁶ |
|---|---|---|
| H | Br | F |
| Me | Br | F |
| t-Bu | Br | F |
| c-Pr | Br | F |
| c-PrCH₂ | Br | F |
| 1,1'-bicyclopropyl-2-yl | Br | F |

| R³ | R⁵ | R⁶ |
|---|---|---|
| 1,1'-bicyclopropyl-1-yl | Br | F |
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-2-yl | Br | Cl |
| H | CF₃ | F |
| Me | CF₃ | F |
| t-Bu | CF₃ | F |
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-2-yl | Cl | Cl |
| 1,1'-bicyclopropyl-1-yl | Cl | Cl |
| Me | OCH₂CF₃ | F |
| Et | OCH₂CF₃ | F |
| c-Pr | OCH₂CF₃ | Cl |
| c-PrCH₂ | OCH₂CF₃ | Cl |
| 1,1'-bicyclopropyl-1-yl | OCH₂CF₃ | Cl |

TABLE 2-continued

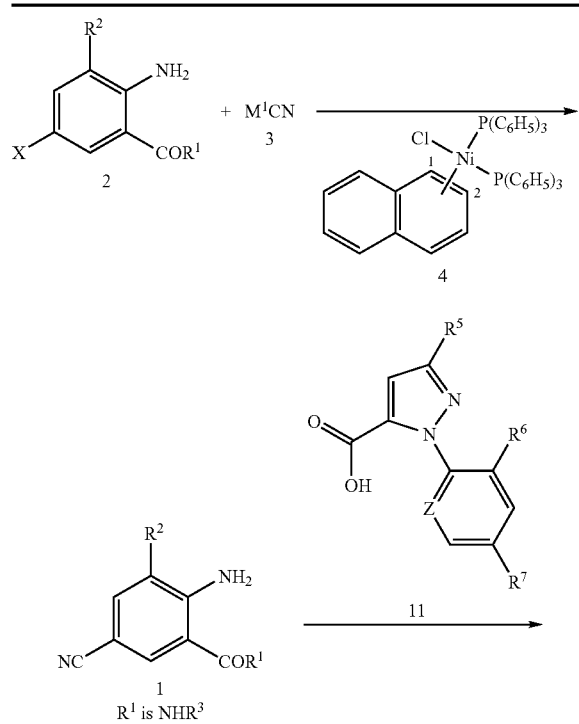

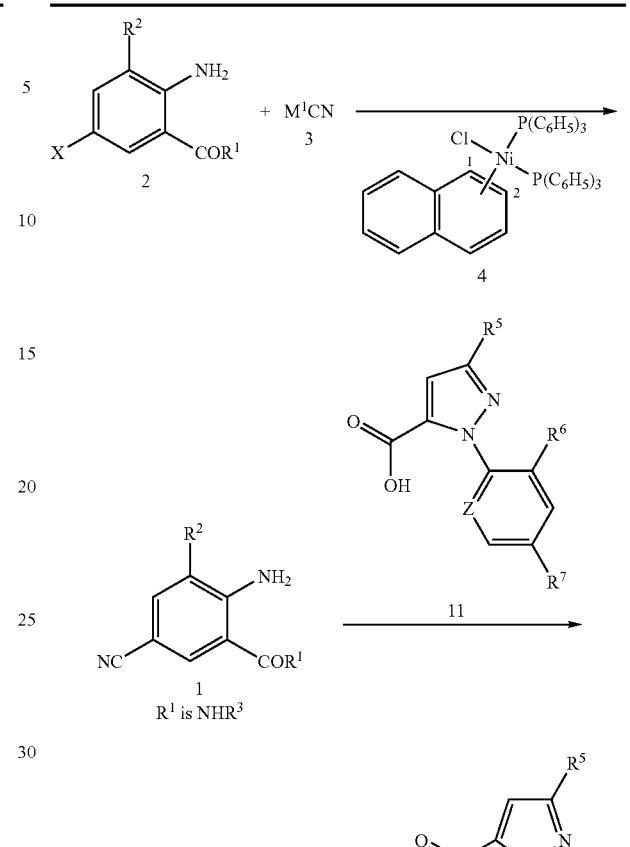

| R³ | R⁵ | R⁶ |
|---|---|---|
| Me | OCH₂CF₃ | Br |
| Et | OCH₂CF₃ | Br |
| Me | OCF₂H | F |
| Et | OCF₂H | F |
| c-Pr | OCF₂H | Cl |
| c-PrCH₂ | OCF₂H | Cl |
| 1,1'-bicyclopropyl-2-yl | OCF₂H | F |
| Me | OCF₂H | Br |
| Et | OCF₂H | Br |
| 2-CH₃-c-Pr | CF₃ | F |
| H | Br | Br |
| Me | Br | Br |
| t-Bu | Br | Br |
| c-Pr | Br | Br |
| c-PrCH₂ | Br | Br |
| 1,1'-bicyclopropyl-1-yl | Br | Br |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | Cl |
| Me | CF₃ | Cl |
| t-Bu | CF₃ | Cl |
| Me | CF₃ | Br |
| Et | CF₃ | Br |
| c-Pr | CF₃ | Br |
| c-PrCH₂ | CF₃ | Br |
| 1,1'-bicyclopropyl-2-yl | CF₃ | Br |
| 1,1'-bicyclopropyl-1-yl | CF₃ | F |

R² is Cl, X is Br, R⁷ is Cl and Z is N.

| R³ | R⁵ | R⁶ |
|---|---|---|
| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |
| c-Pr | Cl | F |
| c-PrCH₂ | Cl | F |
| 1,1'-bicyclopropyl-2-yl | Cl | F |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-2-yl | Br | Cl |
| H | CF₃ | F |
| Me | CF₃ | F |
| t-Bu | CF₃ | F |

TABLE 2-continued

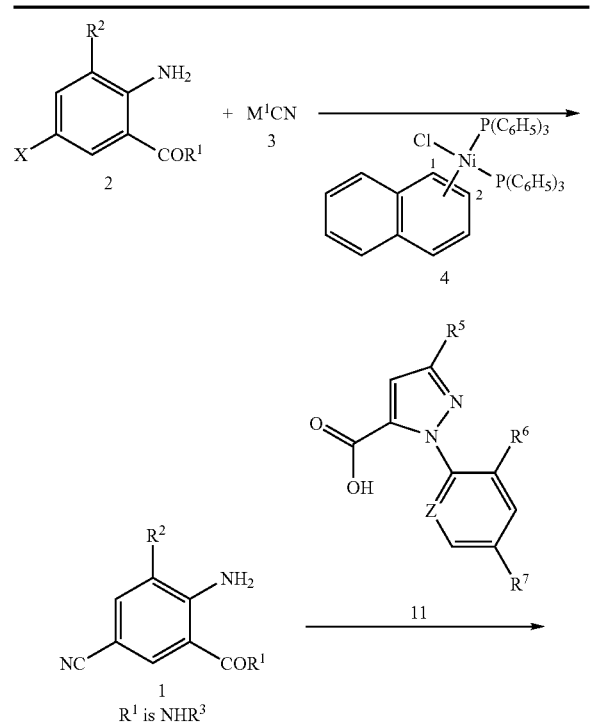

| R³ | R⁵ | R⁶ |
|---|---|---|
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-2-yl | Cl | Cl |
| 1,1'-bicyclopropyl-1-yl | Cl | Cl |
| Me | OCH₂CF₃ | F |
| Et | OCH₂CF₃ | F |
| c-Pr | OCH₂CF₃ | Cl |
| c-PrCH₂ | OCH₂CF₃ | Cl |
| 1,1'-bicyclopropyl-1-yl | OCH₂CF₃ | Cl |
| Me | OCH₂CF₃ | Br |
| Et | OCH₂CF₃ | Br |
| Me | OCF₂H | F |
| Et | OCF₂H | F |
| c-Pr | OCF₂H | Cl |
| c-PrCH₂ | OCF₂H | Cl |
| 1,1'-bicyclopropyl-2-yl | OCF₂H | F |
| Me | OCF₂H | Br |
| Et | OCF₂H | Br |
| 2-CH₃-c-Pr | CF₃ | F |
| H | Br | Br |
| Me | Br | Br |
| t-Bu | Br | Br |
| c-Pr | Br | Br |
| c-PrCH₂ | Br | Br |
| 1,1'-bicyclopropyl-1-yl | Br | Br |

TABLE 2-continued

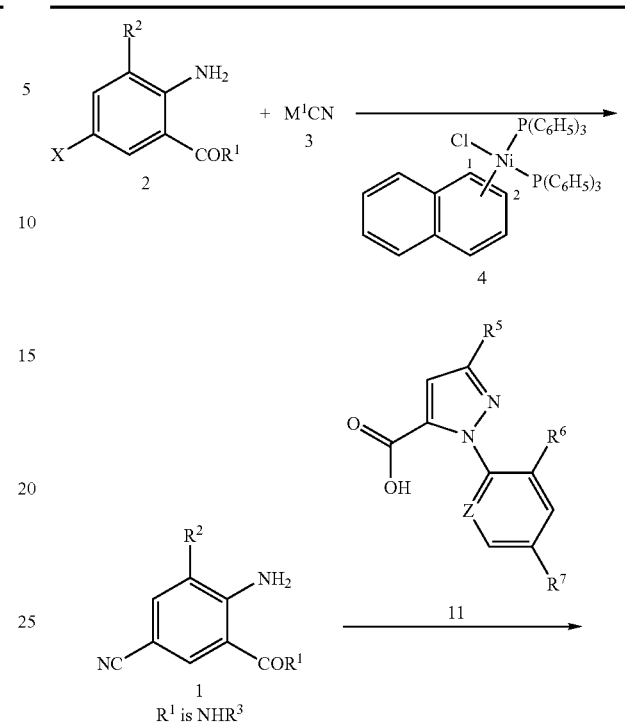

| R³ | R⁵ | R⁶ |
|---|---|---|
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | Cl |
| Me | CF₃ | Cl |
| t-Bu | CF₃ | Cl |
| Me | CF₃ | Br |
| Et | CF₃ | Br |
| c-Pr | CF₃ | Br |
| c-PrCH₂ | CF₃ | Br |
| 1,1'-bicyclopropyl-2-yl | CF₃ | Br |
| 1,1'-bicyclopropyl-1-yl | CF₃ | F |

R² is Cl, X is I, R⁷ is Cl and Z is N.

| R³ | R⁵ | R⁶ |
|---|---|---|
| H | Br | F |
| Me | Br | F |
| t-Bu | Br | F |
| c-Pr | Br | F |
| c-PrCH₂ | Br | F |
| 1,1'-bicyclopropyl-2-yl | Br | F |
| 1,1'-bicyclopropyl-1-yl | Br | F |
| H | Cl | F |
| Me | Cl | F |
| t-Bu | Cl | F |

TABLE 2-continued

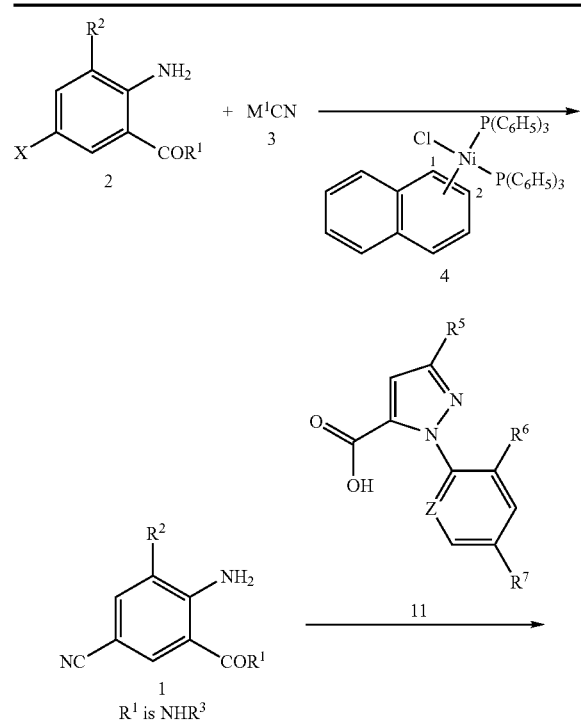

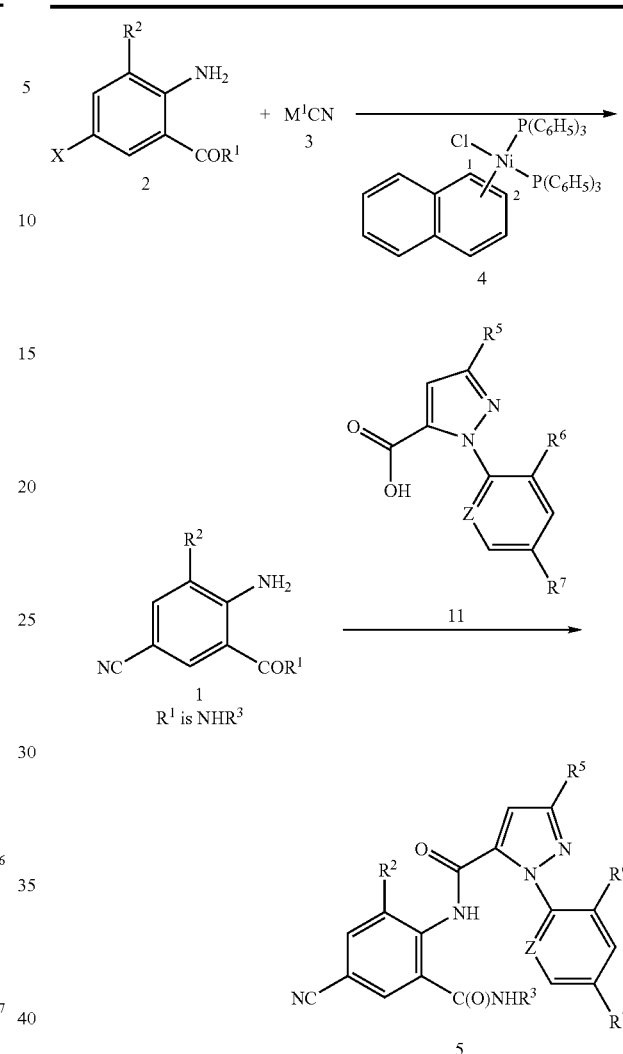

| R³ | R⁵ | R⁶ |
|---|---|---|
| c-Pr | Cl | F |
| c-PrCH₂ | Cl | F |
| 1,1'-bicyclopropyl-2-yl | Cl | F |
| H | Br | Cl |
| Me | Br | Cl |
| t-Bu | Br | Cl |
| c-Pr | Br | Cl |
| c-PrCH₂ | Br | Cl |
| 1,1'-bicyclopropyl-2-yl | Br | Cl |
| H | CF₃ | F |
| Me | CF₃ | F |
| t-Bu | CF₃ | F |
| H | Cl | Cl |
| Me | Cl | Cl |
| t-Bu | Cl | Cl |
| c-Pr | Cl | Cl |
| c-PrCH₂ | Cl | Cl |
| 1,1'-bicyclopropyl-2-yl | Cl | Cl |
| 1,1'-bicyclopropyl-1-yl | Cl | Cl |
| Me | OCH₂CF₃ | F |
| Et | OCH₂CF₃ | F |
| c-Pr | OCH₂CF₃ | Cl |
| c-PrCH₂ | OCH₂CF₃ | Cl |
| 1,1'-bicyclopropyl-1-yl | OCH₂CF₃ | Cl |
| Me | OCH₂CF₃ | Br |
| Et | OCH₂CF₃ | Br |
| Me | OCF₂H | F |
| Et | OCF₂H | F |

| R³ | R⁵ | R⁶ |
|---|---|---|
| c-Pr | OCF₂H | Cl |
| c-PrCH₂ | OCF₂H | Cl |
| 1,1'-bicyclopropyl-2-yl | OCF₂H | F |
| Me | OCF₂H | Br |
| Et | OCF₂H | Br |
| 2-CH₃-c-Pr | CF₃ | F |
| H | Br | Br |
| Me | Br | Br |
| t-Bu | Br | Br |
| c-Pr | Br | Br |
| c-PrCH₂ | Br | Br |
| 1,1'-bicyclopropyl-1-yl | Br | Br |
| H | Cl | Br |
| Me | Cl | Br |
| t-Bu | Cl | Br |
| c-Pr | Cl | Br |
| c-PrCH₂ | Cl | Br |
| 1,1'-bicyclopropyl-2-yl | Cl | Br |
| 1,1'-bicyclopropyl-1-yl | Cl | Br |
| H | CF₃ | Cl |
| Me | CF₃ | Cl |
| t-Bu | CF₃ | Cl |
| Me | CF₃ | Br |
| Et | CF₃ | Br |
| c-Pr | CF₃ | Br |

TABLE 2-continued

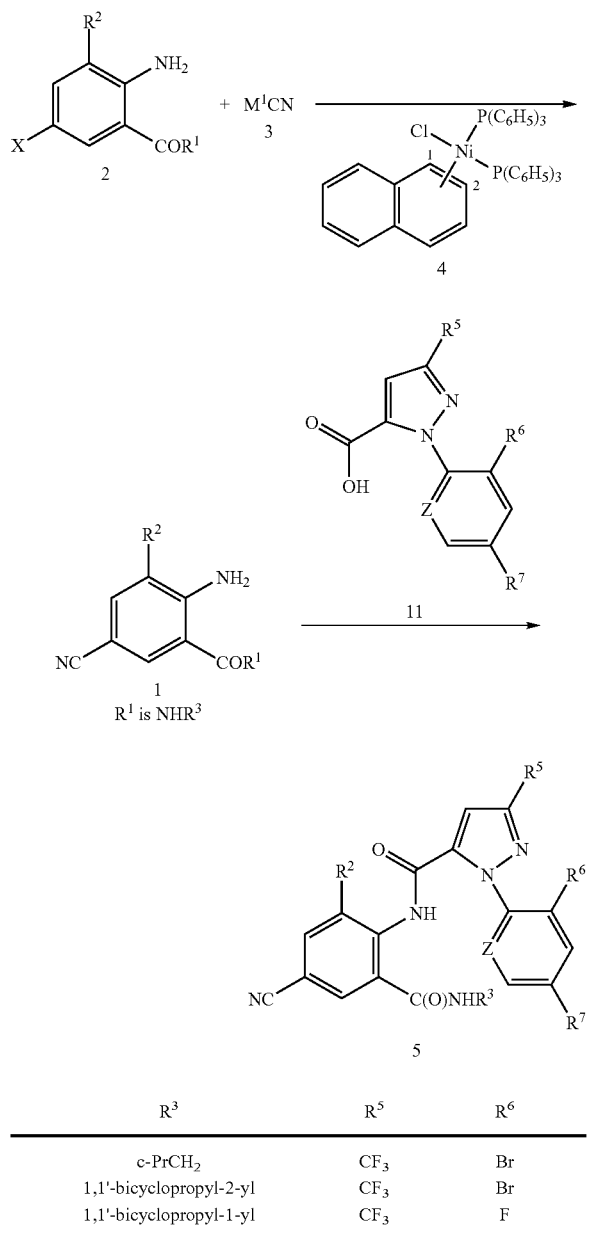

| $R^3$ | $R^5$ | $R^6$ |
|---|---|---|
| c-PrCH$_2$ | CF$_3$ | Br |
| 1,1'-bicyclopropyl-2-yl | CF$_3$ | Br |
| 1,1'-bicyclopropyl-1-yl | CF$_3$ | F |

What is claimed is:

1. A method for preparing a compound of Formula 1

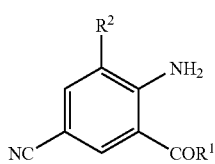

wherein $R^1$ is NHR$^3$ or OR$^4$;

$R^2$ is CH$_3$ or Cl;

$R^3$ is H, C$_1$-C$_4$ alkyl, cyclopropyl, cyclopropylcyclopropyl, cyclopropylmethyl or methylcyclopropyl; and $R^4$ is H or C$_1$-C$_4$ alkyl;

comprising contacting (1) a compound of Formula 2

2

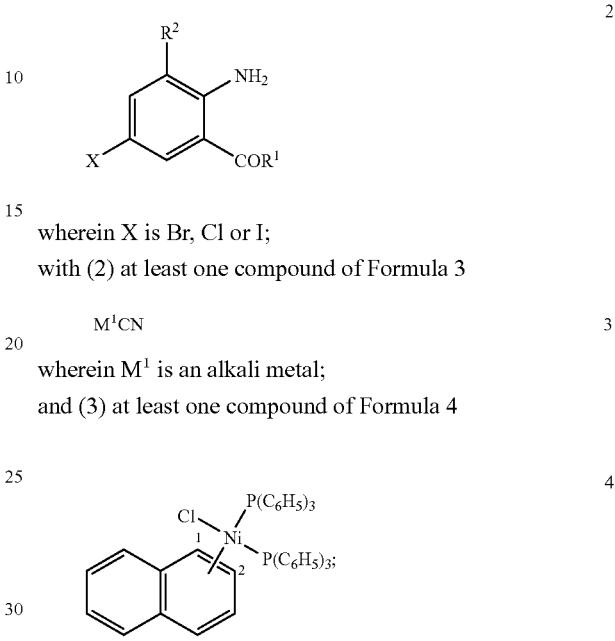

wherein X is Br, Cl or I;

with (2) at least one compound of Formula 3

M$^1$CN      3 wherein M$^1$ is an alkali metal;

and (3) at least one compound of Formula 4

4 provided that when X is Cl, then $R^2$ is methyl.

2. The method of claim 1 wherein $R^1$ is NHR$^3$.

3. The method of claim 2 wherein $R^3$ is CH$_3$, $R^2$ is CH$_3$, and X is Br or Cl.

4. The method of claim 1 wherein M$^1$ is selected from the group consisting of sodium and potassium.

5. The method of claim 1 wherein the at least one compound of Formula 4 contains at least about 80 percent chloro-1-naphthalenylbis(triphenylphosphine)-nickel.

6. The method of claim 5 wherein the at least one compound Formula 4 contains at least about 90 percent chloro-1-naphthalenylbis(triphenylphosphine)nickel.

7. The method of claim 1 wherein the compound of Formula 2, the compound or compounds of Formula 3 and the compound or compounds of Formula 4 are contacted in the presence of a suitable organic solvent.

8. The method of claim 7 wherein the compound of Formula 2 and the compound or compounds of Formula 3 are contacted with the suitable organic solvent to form a mixture, and then a slurry of the compound or compounds of Formula 4 in the suitable organic solvent is added to the mixture.

9. The method of claim 7 wherein the suitable organic solvent comprises one or more solvents selected from ethanol, xylenes, toluene and N,N'-dimethylformamide.

10. The method of claim 7 wherein the suitable organic solvent contains at least 50% by weight ethanol, and M$^1$ is potassium.

11. The method of claim 1 further comprising preparing the at least one compound of Formula 4 by contacting a mixture of (i) at least one compound of Formula 9

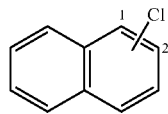

and (ii) at least one metal reducing agent with (iii) dichlorobis(triphenylphosphine)nickel.

12. The method of claim 1 further comprising a method for removing nickel impurities from a mixture thereof with compounds of Formula 1 comprising contacting the mixture with oxygen in the presence of an aqueous cyanide solution.

13. The method of claim 12 wherein the aqueous cyanide solution comprises sodium cyanide, potassium cyanide, or mixtures thereof.

* * * * *